(12) United States Patent
Pulido et al.

(10) Patent No.: US 10,441,643 B2
(45) Date of Patent: Oct. 15, 2019

(54) METHODS AND MATERIALS FOR TREATING CANCER

(71) Applicants: Mayo Foundation for Medical Education and Research, Rochester, MN (US); University of Leeds, Leeds (GB)

(72) Inventors: Jose S. Pulido, Rochester, MN (US); Richard G. Vile, Rochester, MN (US); Timothy J. Kottke, Oronoco, MN (US); Jill M. Thompson, Stewartville, MN (US); Rosa Maria Diaz, Rochester, MN (US); Christine Marie Pulido, Rochester, MN (US); Alan A. Melcher, Leeds (GB); Peter Selby, Leeds (GB)

(73) Assignees: Mayo Foundation for Medical Education and Research, Rochester, MN (US); University of Leeds, Leeds (GB)

(*) Notice: Subject to any disclaimer, the term of this patent is extended or adjusted under 35 U.S.C. 154(b) by 0 days.

(21) Appl. No.: 15/126,333

(22) PCT Filed: Mar. 19, 2015

(86) PCT No.: PCT/US2015/021574
§ 371 (c)(1),
(2) Date: Sep. 15, 2016

(87) PCT Pub. No.: WO2015/143221
PCT Pub. Date: Sep. 24, 2015

(65) Prior Publication Data
US 2017/0080065 A1 Mar. 23, 2017

Related U.S. Application Data

(60) Provisional application No. 61/955,648, filed on Mar. 19, 2014.

(51) Int. Cl.
A61K 39/00 (2006.01)
A61K 35/766 (2015.01)
C07K 14/82 (2006.01)
C07K 16/28 (2006.01)

(52) U.S. Cl.
CPC ........ *A61K 39/0011* (2013.01); *A61K 35/766* (2013.01); *A61K 39/00* (2013.01); *C07K 14/82* (2013.01); *C07K 16/28* (2013.01); *C07K 16/2818* (2013.01); *A61K 2039/505* (2013.01); *A61K 2039/507* (2013.01); *A61K 2039/53* (2013.01); *A61K 2039/70* (2013.01); *C12N 2760/20243* (2013.01)

(58) Field of Classification Search
None
See application file for complete search history.

(56) References Cited

U.S. PATENT DOCUMENTS

| | | | |
|---|---|---|---|
| 5,695,963 | A | 12/1997 | McKnight et al. |
| 6,140,053 | A | 10/2000 | Koster |
| 2010/0121033 | A1 | 5/2010 | Camphausen et al. |
| 2010/0129389 | A1 | 5/2010 | Ware et al. |
| 2010/0168206 | A1 | 7/2010 | Gollob et al. |
| 2010/0221349 | A1 | 9/2010 | Fuller |
| 2012/0258046 | A1 | 10/2012 | Mutzke |
| 2012/0308484 | A1 | 12/2012 | Szalay et al. |
| 2012/0308601 | A1* | 12/2012 | Vile ............... A61K 39/0011 424/199.1 |
| 2013/0287772 | A1 | 10/2013 | Halbert et al. |
| 2015/0064218 | A1 | 3/2015 | Pulido et al. |
| 2017/0080066 | A1 | 3/2017 | Vile et al. |
| 2017/0143813 | A1* | 5/2017 | Pulido ............. A61K 39/0011 |

FOREIGN PATENT DOCUMENTS

| | | | |
|---|---|---|---|
| WO | WO 2008/109825 | 9/2008 | |
| WO | WO 2011/100468 | 8/2011 | |
| WO | WO-2013036201 A1 * | 3/2013 | ........... A61K 39/12 |
| WO | WO 2013/138697 | 9/2013 | |
| WO | WO 2013/173223 | 11/2013 | |
| WO | WO 2013/178344 | 12/2013 | |

OTHER PUBLICATIONS

GenBank® Accession No. AAB29640, GI: 544859, "N-ras [*Homo sapiens*]," Sep. 23, 1994, 1 page.
GenBank® Accession No. AC_000025.1, GI: 83280973, "Mus musculus strain mixed chromosome 3, alternate assembly Mm_Celera, whole genome shotgun sequence," Oct. 19, 2010, 2 pages.
GenBank® Accession No. AF047043.1, "Mus musculus Sox-10 protein (Sox10) mRNA, complete cds," Jun. 27, 1998, 2 pages.
GenBank® Accession No. AF063658 GI: 3132832, "*Homo sapiens* vascular endothelial growth factor receptor 2 (KDR) mRNA, complete cds," May 16, 1998, 2 pages.
GenBank® Accession No. AF399931.1 GI: 33307711, "*Homo sapiens* P-glycoprotein (ABCB1) mRNA, complete cds," Jun. 10, 2004, 2 pages.
GenBank® Accession No. AF493896.1 GI: 20147684, "*Homo sapiens* guanine nucleotide binding protein alpha q (GNAQ) mRNA, complete cds," Apr. 14, 2002, 1 pages.

(Continued)

*Primary Examiner* — Peter J Reddig
(74) *Attorney, Agent, or Firm* — Fish & Richardson P.C.

(57) ABSTRACT

This document provides methods and materials for treating cancer. For example, methods and materials for treating cancer using combinations of antigens are provided. For example, VSV vectors designed to express a GNAQ antigen, a TYRP1 antigen, and an N-RAS antigen can be used to reduce the number of cancer cells (e.g., uveal melanoma cells) within a mammal (e.g., a human). In some cases, VSV vectors designed to express a BRAF antigen, a TOPO-11a antigen, and a YB-I antigen can be used to reduce the number of cancer cells (e.g., skin melanoma cells) within a mammal (e.g., a human). The composition can comprise less than 50 separate nucleic acid molecules.

6 Claims, 25 Drawing Sheets

Specification includes a Sequence Listing.

(56) References Cited

OTHER PUBLICATIONS

GenBank® Accession No. AF493919.1 GI: 20147730, "*Homo sapiens* Ras family small GTP binding protein N-Ras (NRAS) mRNA, complete cds," Apr. 14, 2002, 1 page.
GenBank® Accession No. AY101192.1 GI: 21429238, "*Homo sapiens* CD44 antigen (CD44) mRNA, complete cds," Jun. 15, 2002, 2 pages.
GenBank® Accession No. AY101193.1 GI: 21429240, "*Homo sapiens* CD44 antigen (CD44) mRNA, complete cds," Jun. 15, 2002, 2 pages.
GenBank® Accession No. AY234788.1 GI: 34539754, "*Homo sapiens* P-glycoprotein ABCB5 mRNA, complete cds," Nov. 17, 2003, 2 pages.
GenBank® Accession No. AY425006.1 GI: 40795902, "*Homo sapiens* P-glycoprotein 1 (ABCB1) mRNA, partial cds, alternatively spliced," Apr. 27, 2004, 1 page.
GenBank® Accession No. AY864315.1 GI: 57791235, "Mus musculus strain BALB/c multidrug resistance protein 1a (Abcb1a) mRNA, complete cds," Jan. 19, 2005, 2 pages.
GenBank® Accession No. BC057583.1 GI: 34785834, "Mus musculus guanine nucleotide binding protein, alpha q polypeptide, mRNA (cDNA clone MGC:67083 Image:6408959), complete cds," Aug. 11, 2006, 3 pages.
GenBank® Accession No. BC061634.1 GI: 38197294, "Mus musculus Y box protein 1, mRNA (cDNA clone MGC:68144 Image:6530605), complete cds," Sep. 1, 2006, 3 pages.
GenBank® Accession No. BC071708.1 GI: 47940505, "*Homo sapiens* Y box binding protein 1, mRNA (cDNA clone MGC:87995 Image:4361396), complete cds," Jun. 23, 2006, 3 pages.
GenBank® Accession No. BC076598.1 GI: 49903295, "Mus musculus tyrosinase-related protein 1, mRNA (cDNA clone MGC:96635 Image:30613975), complete cds," Jul. 15, 2006, 3 pages.
GenBank® Accession No. BT020029 GI: 54696919, "*Homo sapiens* SRY (sex determining region Y)-box 10 mRNA, complete cds," Oct. 28, 2004, 2 pages.
GenBank® Accession No. CAG28611, GI: 47115303, "TYRP1 [*Homo sapiens*]," Oct. 16, 2008, 2 pages.
GenBank® Accession No. CR407683.1 Gi: 47115302, "*Homo sapiens* full open reading frame cDNA clone RZPDo834D033D for gene TYRP1, tyrosinase-related protein 1 complete cds, without stopcodon," Oct. 16, 2008, 2 pages.
GenBank® Accession No. EU854148.1 GI: 194740429, "*Homo sapiens* multidrug resistance protein 1 mRNA, complete cds, alternatively spliced," Aug. 5, 2008, 2 pages.
GenBank® Accession No. EU884114.1 GI: 215400615, "Mus musculus strain C57BL/6 soluble vascular endothelial growth factor receptor 2 mRNA, complete cds," Nov. 15, 2010, 2 pages.
GenBank® Accession No. J04444, GI: 181239, "Human cytochrome c-1 gene, complete cds," Nov. 2, 1994, 3 pages.
GenBank® Accession No. J05114 GI: 37092, "Human mRNA for transforming growth factor-beta (TGF-beta)," Mar. 27, 1995, 2 pages.
GenBank® Accession No. JQ655148.1 GI: 406817019, "Mus musculus P-glycoprotein (Abcb5) mRNA, complete cds," Feb. 9, 2014, 2 pages.
GenBank® Accession No. M13177.1 GI: 201952, "Mouse transforming growth factor beta mRNA (TGF-beta), complete cds," Apr. 27, 1993, 2 pages.
GenBank® Accession No. M23234.1 GI: 187501, "Human membrane glycoprotein P (mdr3) mRNA, complete cds," Jun. 11, 1993, 2 pages.
GenBank® Accession No. M24417.1 GI: 2000329, "Mouse phosphoglycoprotein mdr1a mRNA, 3' end," Nov. 18, 1993, 2 pages.
GenBank® Accession No. M33581.1 GI: 199104, "Mouse P-glycoprotein (mdr1a) mRNA, complete cds," Apr. 27, 1993, 3 pages.
GenBank® Accession No. M62867 GI: 199820, "Mouse Y box transcription factor (MSY-1) mRNA, complete cds," Mar. 7, 1995, 2 pages.
GenBank® Accession No. NC_000069.6 GI: 372099107, "Mus musculus strain C57BL/6J chromosome 3, MGSCv37 C57BL/6J," Oct. 19, 2010, 1 page.
GenBank® Accession No. NM_009863 GI: 409168309, "Mus musculus cell division cycle 7 (S. cerevisiae) (Cdc7), transcript variant 2, mRNA," Oct. 18, 2012, 4 pages.
GenBank® Accession No. NM_000550, GI: 169881242, "*Homo sapiens* tyrosinase-related protein 1 (TYRP1), mRNA," Mar. 12, 2011, 4 pages.
GenBank® Accession No. NM_001067.3 GI: 300193028, "*Homo sapiens* topoisomerase (DNA) II alpha 170kDa (TOP2A), mRNA," Mar. 11, 2011, 9 pages.
GenBank® Accession No. NM_001134419.1 GI: 197313664, "*Homo sapiens* cell division cycle 7 (CDC7), transcript variant 2, mRNA," Mar. 10, 2011, 5 pages.
GenBank® Accession No. NM_001134420.1 GI: 197313666, "*Homo sapiens* cell division cycle 7 homolog (S. cerevisiae) (CDC7), transcript variant 3, mRNA," Mar. 11, 2011, 5 pages.
GenBank® Accession No. NM_001163941.1 GI: 255708476, "*Homo sapiens* ATP-binding cassette, sub-family B (MDR/TAP), member 5 (ABCB5), transcript variant 1, mRNA," Mar. 11, 2011, 6 pages.
GenBank® Accession No. NM_001163942.1 GI: 255708370, "*Homo sapiens* ATP-binding cassette, sub-family B (MDR/TAP), member 5 (ABCB5), transcript variant 3, mRNA," Mar. 11, 2011, 4 pages.
GenBank® Accession No. NM_001163993.2 GI: 574957217, "*Homo sapiens* ATP-binding cassette, sub-family B (MDR/TAP), member 5 (ABCB5), transcript variant 4, mRNA," Mar. 12, 2011, 4 pages.
GenBank® Accession No. NM_001177352.1 GI: 293629263, "Mus musculus myelocytomatosis oncogene (Myc), transcript variant 1, mRNA," Mar. 11, 2011, 5 pages.
GenBank® Accession No. NM_001177353.1 GI: 293629266, "Mus musculus myelocytomatosis oncogene (Myc), transcript variant 2, mRNA," Mar. 13, 2011, 5 pages.
GenBank® Accession No. NM_001177354.1 GI: 293629269, "Mus musculus myelocytomatosis oncogene (Myc), transcript variant 2, mRNA," Mar. 11, 2011, 5 pages.
GenBank® Accession No. NM 001177787 GI: 295293147, "Mus musculus CD44 antigen (Cd44), transcript variant 6, mRNA," Mar. 12, 2011, 5 pages.
GenBank® Accession No. NM_001282014.1 GI: 530537243, "Mus musculus tyrosinase-related protein 1 (Tyrp1), transcript variant 2, mRNA," Aug. 14, 2013, 4 pages.
GenBank® Accession No. NM_001282015.1 GI: 530537245, "Mus musculus tyrosinase-related protein 1 (Tyrp1), transcript variant 3, mRNA," Aug. 14, 2013, 4 pages.
GenBank® Accession No. NM_001430 GI: 262527236, "*Homo sapiens* endothelial PAS domain protein 1 (EPAS1), mRNA," Mar. 13, 2011, 6 pages.
GenBank® Accession No. NM_002154, GI: 38327038, "*Homo sapiens* heat shock 70kDa protein 4 (HSPA4), mRNA," Feb. 15, 2009, 5 pages.
GenBank® Accession No. NM_002524, GI: 185134767, "*Homo sapiens* neuroblastoma RAS viral (v-ras) oncogene homolog (NRAS), mRNA," Mar. 13, 2011, 5 pages.
GenBank® Accession No. NM_002524.4 GI: 334688826, "*Homo sapiens* neuroblastoma RAS viral (v-ras) oncogene homolog (NRAS), mRNA," Jun. 2, 2011, 5 pages.
GenBank® Accession No. NM_003503.3 GI: 197313663, "*Homo sapiens* cell division cycle 7 homolog (S. cerevisiae) (CDC7), transcript variant 1, mRNA," Mar. 13, 2011, 5 pages.
GenBank® Accession No. NM_004333.4 GI: 187608632, "*Homo sapiens* v-raf murine sarcoma viral oncogene homolog B1 (BRAF), mRNA," Mar. 13, 2011, 7 pages.
GenBank® Accession No. NM_004559.3 GI: 109134359, "*Homo sapiens* Y box binding protein 1 (YBX1), mRNA," Mar. 13, 2011, 5 pages.
GenBank® Accession No. NM_008139.5 Gi: 145966786, "Mus musculus guanine nucleotide binding protein, alpha q polypeptide (Gnaq), mRNA," Mar. 12, 2011, 5 pages.

(56) References Cited

OTHER PUBLICATIONS

GenBank® Accession No. NM_009863 GI: 409168309, "Mus musculus cell division cycle 7 (S. cerevisiae) (Cdc7), mRNA," Mar. 10, 2012, 4 pages.
GenBank® Accession No. NM_010849.4 GI: 100913213, "Mus musculus myelocytomatosis oncogene (Myc), transcript variant 1, mRNA," Mar. 11, 2011, 5 pages.
GenBank® Accession No. NM_010937.2 GI: 372099107, "Mus musculus neuroblastoma ras oncogene (Nras), mRNA," Mar. 13, 2011, 4 pages.
GenBank® Accession No. NM_011075 GI: 161169006, "Mus musculus ATP-binding cassette, subfamily B (MDR/TAP), member 1B (Abcb1b), mRNA," Mar. 10, 2011, 7 pages.
GenBank® Accession No. NM_011623, "Mus musculus topoisomerase (DNA) II alpha (Top2a), mRNA," Mar. 11, 2012, 7 pages.
GenBank® Accession No. NM_011732.2 GI: 113205058, "Mus musculus Y box protein 1 (Ybx1), mRNA," Mar. 13, 2011, 5 pages.
GenBank® Accession No. NM_029961 XM_906632 GI: 255708374, "Mus musculus ATP-binding cassette, sub-family B (MDR/TAP), member 5 (Abcb5), mRNA," Mar. 11, 2011, 4 pages.
GenBank® Accession No. NM_031202.3 GI: 530537240, "Mus musculus tyrosinase-related protein 1 (Tyrp1), mRNA," Mar. 11, 2011, 4 pages.
GenBank® Accession No. NM_139294.5 GI: 153791903, "Mus musculus Braf transforming gene (Braf), mRNA," Feb. 27, 2011, 7 pages.
GenBank® Accession No. NM_178559.5 GI: 255708475, "*Homo sapiens* ATP-binding cassette, sub-family B (MDR/TAP), member 5 (ABCB5), transcript variant 2, mRNA," Mar. 13, 2011, 6 pages.
GenBank® Accession No. NP_002145, GI: 38327039, "Heat shock 70kDa protein 4 [*Homo sapiens*]," Feb. 15, 2009, 2 pages.
GenBank® Accession No. NP_061820, GI: 11128019, "Cytochrome c [*Homo sapiens*]," Mar. 11, 2011, 2 pages.
GenBank® Accession No. NW_004078038.1, "*Homo sapiens* chromosome 9 genomic scaffold, alternate assembly CHM1_1.0, whole genome shotgun sequence," Nov. 2, 2012, 4 pages.
GenBank® Accession No. U40038.1 GI: 1181670, "Human GTP-binding protein alpha q subunit (GNAQ) mRNA, complete cds," Feb. 7, 1996, 2 pages.
GenBank® Accession No. V00568 GI: 34815, "Human mRNA encoding the c-myc oncogene," Oct. 7, 2008, 2 pages.
GenBank® Accession No. X02812 GI: 37092, "Human mRNA for transforming growth factor-beta (TGF-beta)," Mar. 27, 1995, 2 pages.
GenBank® Accession No. X51420.1 GI: 37512, "*Homo sapiens* mRNA for tyrosinase-related protein precursor (TYRP1)," Oct. 7, 2008, 2 pages.
GenBank® Accession No. X57621.1 GI: 55450, "M.musculus YB-1 mRNA," Apr. 18, 2005, 2 pages.
GenBank® Accession No. X58723 GI: 34522, "Human MDR1 (multidrug resistance) gene for P-glycoprotein," Nov. 14, 2006, 2 pages.
GenBank® Accession No. XM_001002680 GI: 255708374, "Predicted: Mus musculus ATP-binding cassette, sub-family B (MDR/TAP), member 5 (ABCB5), mRNA," Jun. 20, 2007, 2 pages.
GenBank® Accession No. XM_005250045.1 GI: 530387105, "Predicted: *Homo sapiens* v-raf murine sarcoma viral oncogene homolog B (BRAF), transcript variant X1, mRNA," Aug. 13, 2013, 4 pages.
GenBank® Accession No. XM_005250046.1 GI: 530387107, "Predicted: *Homo sapiens* v-raf murine sarcoma viral oncogene homolog B (BRAF), transcript variant X2, mRNA," Aug. 13, 2013, 4 pages.
GenBank® Accession No. XM_005250047.1 GI: 530387109, "Predicted: *Homo sapiens* v-raf murine sarcoma viral oncogene homolog B (BRAF), transcript variant X3, mRNA," 2 pages.
GenBank® Accession No. XM_005251574.1 GI: 530390132, "Predicted: *Homo sapiens* tyrosinase-related protein 1 (TYRP1), transcript variant X1, mRNA," Feb. 3, 2014, 3 pages.
GenBank® Accession No. XM_005270904.1 GI: 530362706, "Predicted: *Homo sapiens* Y box binding protein 1 (YBX1), transcript variant X1, mRNA," Aug. 13, 2013, 2 pages.

"A Randomized Study of Nivolumab Versus Bevacizumab and a Safety Study of Nivolumab in Adult Subjects With Recurrent Glioblastoma (GBM) (CheckMate 143)," Clinical Trials.gov [online] Dec. 2014, [retrieved on Mar. 18, 2015]. Retrieved from the Internet: <URL:https://clinicaltrials.gov/ct2/show/NCT02017717>, 3 pages.
"UniProt entry P08183—MDR1_HUMAN: Multidrug resistance protein 1," Aug. 1, 1988, pp. 112. Retrieved from the Internet: <http://www.uniprot.org/uniprot/P08183#pathology_and_biotech> on Jun. 3, 2015.
"UniProt entry P35968—VGFR2_HUMAN: Vascular endothelial growth factor receptor 2," Jun. 1, 1994, pp. 1-8. Retrieved from the Internet: <http://www.uniprot.org/uniprot/P35968> on Jun. 3, 2015.
"Using Viro/Immunotherapy to Target Stem-Like Cells of Tumor Recurrence," Oncolytic Viruses and Stem Cell Workshop, National Cancer Institute (NCI), Washington D.C., Sep. 6, 2013, [slideshow] 51 pages.
Ahmad et al., "Optimised electroporation mediated DNA vaccination for treatment of prostate cancer," *Genetics Vaccines and Therapy*, 8:1, pp. 1-13, Feb. 5, 2010.
Alonso-Camino et al., "The profile of tumor antigens which can be targeted by immunotherapy depends upon the tumor's anatomical site," *Mol. Ther.*, 22(11):1936-1948, Nov. 2014.
Avogadri and Wolchok, "Selecting antigens for cancer vaccines," Nat. Biotechnol. 30(4):328-329, Apr. 10, 2012.
Barry et al., "Expression library immunization to discover and improve vaccine antigens," *Immunol Rev.*, 199:68-83, Jun. 2004.
Baxevanis et al., "Cancer immunotherapy," *Crit Rev Clin Lab Sci.*, 46(4): 167-189, 2009.
Boisgerault et al., "Functional cloning of recurrence-specific antigens identifies molecular targets to treat tumor relapse," Mol. Ther., 21(8):1507-1516, Epub Jun. 11, 2013.
Bridle et al., "Vesicular stomatitis virus as a novel cancer vaccine vector to prime antitumor immunity amenable to rapid boosting with adenovirus," Mol. Ther., 17(10):1814-1821, Oct. 2009.
Chen et al., "Principal expression of two mRNA isoforms (ABCB 5alpha and ABCB 5beta ) of the ATP-binding cassette transporter gene ABCB 5 in melanoma cells and melanocytes," *Pigment Cell Res.*, 18(2):102-112, Apr. 2005 [author manuscript].
Cho et al., "A potent vaccination strategy that circumvents lymphodepletion for effective antitumor adoptive T-cell therapy," *Cancer Res.*, 72:1986-1995, Apr. 15, 2012.
Chong et al., "Expression of co-stimulatory molecules by tumor cells decreases tumorigenicity but may also reduce systemic antitumor immunity," *Hum Gene Ther.*, 7(14):1771-1779, Sep. 10, 1996.
Cluff, "Monophosphoryl Lipid A (MPL) as an Adjuvant for Anit-Cancer Vaccines: Clinical Results," *Lipid A in Cancer Therapy*, Landes Bioscience and Springer Science and Business Media, Chpt. 10, pp. 111-123, 2009.
Daniels et al., "A simple method to cure established tumors by inflammatory killing of normal cells," Nature Biol., 22(9):1125-1132, Epub Aug. 2004.
Diaz et al., "Oncolytic immunovirotherapy for melanoma using vesicular stomatitis virus," Cancer Res., 67(6):2840-2848 Mar. 2007.
Ebert et al., "Systemic therapy of experimental breast cancer metastases by mutant vesicular stomatitis virus in immune-competent mice," Cancer Gene Ther., 12(4):350-358, Apr. 2005.
Fernandez et al., "Genetically engineered vesicular stomatitis virus in gene therapy: application for treatment of malignant disease," J. Virol., 76(2):895-904, Jan. 2002.
Ferrone, "Immunotherapy dispenses with tumor antigens," Nature Biotech., 2004, 22(9):1096-1098.
Francisco et al., "Chapter 4: Melanoma Genetics: From Susceptibility to Progression," Melanoma—From Early Detection to Treatment, Dr. Ht Duc (Ed.), pp. 83-136. Retrieved from the Internet: <http://www.intechopen.com/books/melanoma-from-early-detection-to-treatment/melanoma-genetics-from-susceptibility-to-progression> Jan. 2013.
Galivo et al., "Interference of CD40L-mediated tumor immunotherapy by oncolytic vesicular stomatitis virus," Human Gene Ther., 21(4):439-450, Apr. 2010.

(56) References Cited

OTHER PUBLICATIONS

Galivo et al., "Single-cycle viral gene expression, rather than progressive replication and oncolysis, is required for VSV therapy of B16 melanoma," Gene Ther., 17(2):158-170, print Feb. 2010, Epub Dec. 2009.
Hall and Brown, "Human N-ras: cDNA cloning and gene structure," Nucleic Acids Res., 13(14):5255-5268, Jul. 1985.
Heim, "Normal high resolution karyotypes in patients with adenomatosis of the colon and rectum," *Hereditas.*, 102(2):171-175, 1985.
Hogquist et al., "T cell receptor antagonist peptides induce positive selection," Cell, 76(1):17-27, Jan. 1994.
Jenks et al., "Safety studies on intrahepatic or intratumoral injection of oncolytic vesicular stomatitis virus expressing interferon-beta in rodents and nonhuman primates," *Hum. Gene Ther.*, 21(4):451-462, Apr. 2010.
Joseph et al., "Association of the autoimmune disease scleroderma with an immunologic response to cancer," *Science*, 343(6167):152-157, Epub Dec. 5, 2013.
Kaluza et al., "Adoptive transfer of cytotoxic T lymphocytes targeting two different antigens limits antigen loss and tumor escape," *Hum Gene Ther.*, 23(10):1054-1064, Epub Aug. 13, 2012.
Kottke et al., "Broad antigenic coverage induced by vaccination with virus-based cDNA libraries cures established tumors," Nat Med., 17(7):854-859, Jun. 2011.
Kottke et al., "Antitumor immunity can be uncoupled from autoimmunity following heat shock protein 70-mediated inflammatory killing of normal pancreas," Cancer Res., 69(19):7767-1774, Oct. 2009.
Kottke et al., "Induction of hsp70-mediated Th17 autoimmunity can be exploited as immunotherapy for metastatic prostate cancer," Cancer Res., 67(24):11970-11979, Dec. 2007.
Lawson et al., "Recombinant vesicular stomatitis viruses from DNA," *PNAS*, 92(10):4477-4481, May 9, 1995.
Linardakis et al., "Enhancing the efficacy of a weak allogeneic melanoma vaccine by viral fusogenic membrane glycoprotein-mediated tumor cell-tumor cell fusion," Cancer Res., 62(19): 5495-5504, Oct. 2002.
Obuchi et al., "Development of recombinant vesicular stomatitis viruses that exploit defects in host defense to augment specific oncolytic activity," *J. Virol.*, 77(16):8843-8856, Aug. 2003.
Overwijk et al., "Tumor regression and autoimmunity after reversal of a functionally tolerant state of self-reactive CD8+ T cells," J. Exp. Med., 198(4):569-580, Aug. 2003.
Pulido et al., "Using virally expressed melanoma cDNA libraries to identify tumor-associated antigens that cure melanoma," *Nat Biotechnol.*, 30(4):337-343, Mar. 18, 2012.
Radvanyi, "Immunotherapy Exposes Cancer Stem Cell Resistance and a New Synthetic Lethality," Mol. Ther. 21:1472-1474, Aug. 2013.
Ramsburg et al., "A vesicular stomatitis virus recombinant expressing granulocyte-macrophage colony-stimulating factor induces enhanced T-cell responses and is highly attenuated for replication in animals," *J. Virol.*, 79(24):15043-15053, Dec. 2005.
Roda et al., "Stabilization of HIF-2α induces sVEGFR-1 production from tumor-associated macrophages and decreases tumor growth in a murine melanoma model," *J. Immunol.*, 189(6):3168-3177, Sep. 15, 2012.
Rommelfanger et al., "Systemic combination virotherapy for melanoma with tumor antigen-expressing vesicular stomatitis virus and adoptive T-cell transfer," *Cancer Res.*, 72(18):4753-4764, Sep. 15, 2012.
Sausville and Burger, "Contributions of human tumor xenografts to anticancer drug development," *Cancer Res*, 66(7): 3351-3354, Apr. 2006.
Shakhova et al., "Sox10 promotes the formation and maintenance of giant congenital naevi and melanoma," *Nat. Cell Biol.*, 14(8):882-890, Aug. 2012.
Shibata et al., "Downstream region of the human tyrosinase-related protein gene enhances its promoter activity," Biochem. Biophys. Res. Commun., 184(2):568-575, Apr. 1992.
Srivastava, "Immunotherapy of human cancer: lessons from mice," *Nat Immunol.*, 1(5):363-366, Nov. 2000.
Suzuki et al., "Structural organization of the human mitochondrial cytochrome c1 gene," J. Biol. Chem., 264(3):1368-1374, Jan. 1989.
Thomas and Massagué, "TGF-beta directly targets cytotoxic T cell functions during tumor evasion of immune surveillance.," Cancer Cell, 8(5):369-380, Nov. 2005.
Van Belle et al., "Melanoma-associated expression of transforming growth factor-beta isoforms," *Am J Pathol.*, 148(6):1887-1894, Jun. 1996.
Vinals et al., "Using in silico transcriptomics to search for tumor-associated antigens for immunotherapy," *Vaccine*, 19(17-19):2607-2614, Mar. 21, 2001.
Wagner et al., "Targeted nucleic acid delivery into tumors: new avenues for cancer therapy," *Biomed Pharmacother.*, 58(3):152-161, Apr. 2004.
Willmon et al., "Vesicular stomatitis virus-induced immune suppressor cells generate antagonism between intratumoral oncolytic virus and cyclophosphamide," Mol. Ther., 19(1):140-149, Jan. 2010.
Wongthida et al., "VSV oncolytic virotherapy in the B16 model depends upon intact MyD88 signaling,"Mol. Ther., 19(1):150-158, Jan. 2011.
Yoshida et al., "Development of gene therapy to target pancreatic cancer," *Cancer Sci.*, 95(4): 283-289, Apr. 2002.
Zhuang et al., "C-MYC overexpression is required for continuous suppression of oncogene-induced senescence in melanoma cells," *Oncogene*, 27(52):6623-6634, Nov. 6, 2008.
European Search Report for Application No. 11742816.9 dated Jul. 10, 2013, 8 pages.
European Search Report for Application No. 13760532.5, dated Oct. 20, 2015, 14 pages.
Office Action for European Application No. 11742816.9, dated Apr. 14, 2016, 5 pages.
Office Action for U.S. Appl. No. 13/578,224 dated May 8, 2013, 14 pages.
Office Action for U.S. Appl. No. 13/578,224 dated Dec. 27, 2013, 17 pages.
Office Action for U.S. Appl. No. 13/578,224 dated Dec. 4, 2014, 14 pages.
Office Action for U.S. Appl. No. 13/578,224 dated Jun. 5, 2015, 14 pages.
Office Action for U.S. Appl. No. 13/578,224 dated Sep. 24, 2015, 16 pages.
Office Action for U.S. Appl. No. 14/385,240, dated Mar. 18, 2016, 14 pages.
Office Action for U.S. Appl. No. 13/578,224, dated Jun. 3, 2016, 14 pages.
International Search Report and Written Opinion in Application No. PCT/US2011/024397, dated Oct. 25, 2011, 10 pages.
International Preliminary Report on Patentability in Application No. PCT/US2011/024397, dated Aug 23, 2012, 6 pages.
International Search Report and Written Opinion for Application No. PCT/US2013/031953, dated Jul. 4, 2013, 8 pages.
International Preliminary Report on Patentability for PCT/US2013/031953 dated Sep. 25, 2014, 6 pages.
International Search Report and Written Opinion in Application No. PCT/US2015/021574, dated Jul. 8, 2015, 23 pages.
International Search Report and Written Opinion in Application No. PCT/US2015/021576, dated Jul. 10, 2015, 13 pages.
International Preliminary Report on Patentability for PCT/US2015/021574, dated Sep. 29, 2016, 14 pages.
International Preliminary Report on Patentability for PCT/US2015/021576, dated Sep. 29, 2016, 10 pages.
De Gruijl et al., "Whole-cell cancer vaccination: from autologous to allogeneic tumor- and dendritic cell-based vaccines," Cancer Immunology Immunotherapy., 57:1569-1577, 2008.
U.S. Appl. No. 13/578,224, filed Aug. 9, 2012, Vile et al.
U.S. Appl. No. 14/385,240, filed Sep. 15, 2014, Pulido et al.
U.S. Appl. No. 15/126,338, filed Sep. 15, 2016, Vile et al.
Drape et al., "Epidermal DNA vaccine for influenza is immunogenic in humans," *Vaccine.*, 24:4475-4481, 2006.

(56) References Cited

OTHER PUBLICATIONS

Kottke et al., "Broad antigenic coverage induced by vaccination with virus-based cDNA libraries cures established tumors," *Nature Medicine.*, 17(7):854-860, Jul. 2011.

"Nucleic Acids and Protein Calculations: DNA Molar Conversions," printed from http://www.genscript.com/converstion.html, as p. 1/1 on Apr. 24, 2017.

Rochard et al., "Genetic immunization with plasmid DNA mediated by electrotransfer," *Human Gene Therapy.*, 22:789-798, Jul. 2011.

Steitz et al., "Genetic immunization of mice with human tyrosinase-related protein 2: Implications for the immunotherapy of melanoma," *International Journal of Cancer.*, 86:89-94, 2000.

Yang et al., "Dendritic cell-directed lentivector vaccine induces antigen-specific immune responses against murine melanoma," *Cancer Gene Therapy.*, 18:370-380, 2011.

Lee et al., "A comprehensive guide to the MAGE family of ubiquitin ligases," J Mol Biol., 429:1114-1142, Apr. 2017.

Lucas et al., "A new MAGE gene with ubiquitous expression does not code for known MAGE antigens recognized by T cells," Cancer Research., 59:4100-4103, Aug. 15, 1999.

Sang et al. Melanoma-associated antigen genes—an update. Cancer Letters, vol. 302, pp. 85-90, 2011. (Year: 2011).

Tseng et al., "Letter to the Editor: Long-term survivors after immunotherapy for metastatic melanoma," Immunology Letters., vol. 139:117-118, Feb. 2011.

Extended European Search Report in International Application No. EP15765220.7, dated Jan. 29, 2018, 22 pages.

U.S. Appl. No. 15/359,333, filed Nov. 22, 2016, 2017-0143813, May 25, 2017, Pulido et al.

Anonymous: "Programme replicating oncolytic virus therapeutics 2013," Jun. 1, 2013, pp. 1-5, Retrieved from the Internet: URL: http://www.iovmc.org/2013/programme/ Retrieved on Sep. 14, 2017.

Extended European Search report for International Application No. EP15765847.7, dated Oct. 13, 2017, 7 pages.

Gessi et al., "GNA11 and N-RAS mutations: alternatives for MAPK pathway activating GNAQ mutations in primary melanocytic tumors of the central nervous system," *Neurobiology Applied Neurobiology.*, 39(4):417-425, Apr. 25, 2013.

Partial Supplementary European Search Report for International Application No. 15765220.7, dated Oct. 23, 2017, 26 pages.

Woodman., "Metastatic uveal melanoma: biology and emerging treatments," *Cancer J.*, 18(2):148-152, Feb. 26, 2014.

\* cited by examiner

FIG. 5

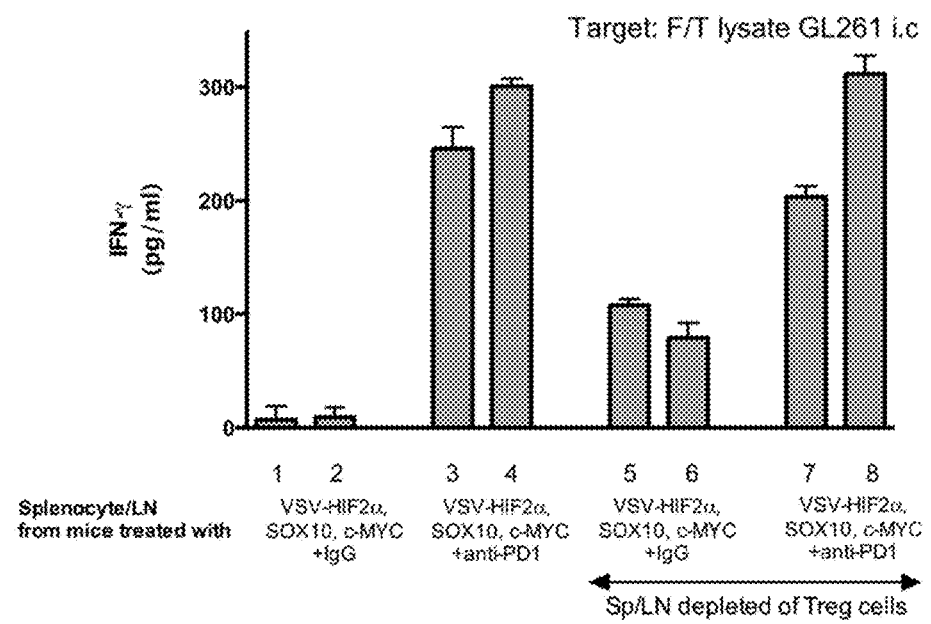
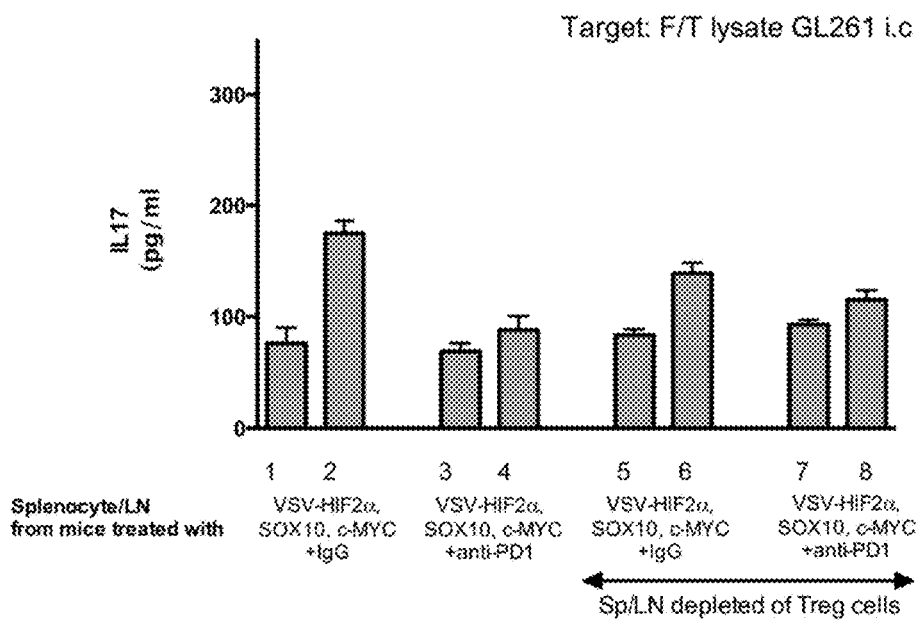
FIG. 7

VSV-N-RAS Virus Recovered from the ASMEL Is Truncated at the 3' End
in the N-RAS Sequences 3'-N-RAS
cDNA
GACCAGACAGGGTGTTGAAGATGCTTTTTACACACTGGTAAGAGAAATA
CGCCAG- (SEQ ID NO:15)

Nhe1 INTERGENIC VSV SEQUENCE

TG- AGCTAGCCAGATTCTTCATGTTTGGACCAAATCAACTTGTGATACCATGCTCAAAGA-
Y- STOP (SEQ ID NO:16)
DEL

Intergenic Dinucleotide L Gene

-
GGCCTCAATTATATTTGAGTTTTTAATTTTTATGAAAAAAACTAACAGC
AATCATG (SEQ ID NO:17)

INTERGENIC VSV Poly A SEQUENCE INTERGENIC VSV Transcription START SEQUENCE

DEL = DELETED:
3'coding end of cDNA:
(c)YRMKKLNSSDDGTQGCMGLPCVVM; (SEQ ID NO:1)
3'untranslated region;
Cellular poly A;
3' primer from pSPORT used to amplify cDNA and linked to Nhe1 site.

FIG. 14

VSV-CYT-C Virus Recovered from the ASMEL Is Truncated at the 3' End in the CYT-C Sequences 3'—CYT-C cDNA ACCATCGAAAACGCATGGGGCTCAAGATGTTGATGATGATGGCTCTGCTGGT
GCCCCTGGTC- (SEQ ID NO:18)
          Nhe1          INTERGENIC VSV SEQUENCE

TGA- GCTAGCCAGATTCTTCATGTTTGGACCAAATCAACTTGTGATACCATGCTCAAAGA-
   Y-STOP                                    (SEQ ID NO:19)
DEL

Intergenic
                                    Dinucleotide          L Gene

GGCCTCAATTATATTGAGTTTTTAATTTTTATGAAAAAACTAACAGC
AATCATG (SEQ ID NO:17)

DEL = DELETED:
3' coding end of cDNA:
(c)YTIKRHKWSVLKSRKLAYRPPK;        INTERGENIC VSV    INTERGENIC VSV
(SEQ ID NO:2)                         Poly A           Transcription
3' untranslated region;              SEQUENCE            START
Cellular poly A;                                            SEQUENCE
3' primer from pSPORT used to
amplify cDNA and linked to Nhe1 site.            FIG. 15

FIG. 17

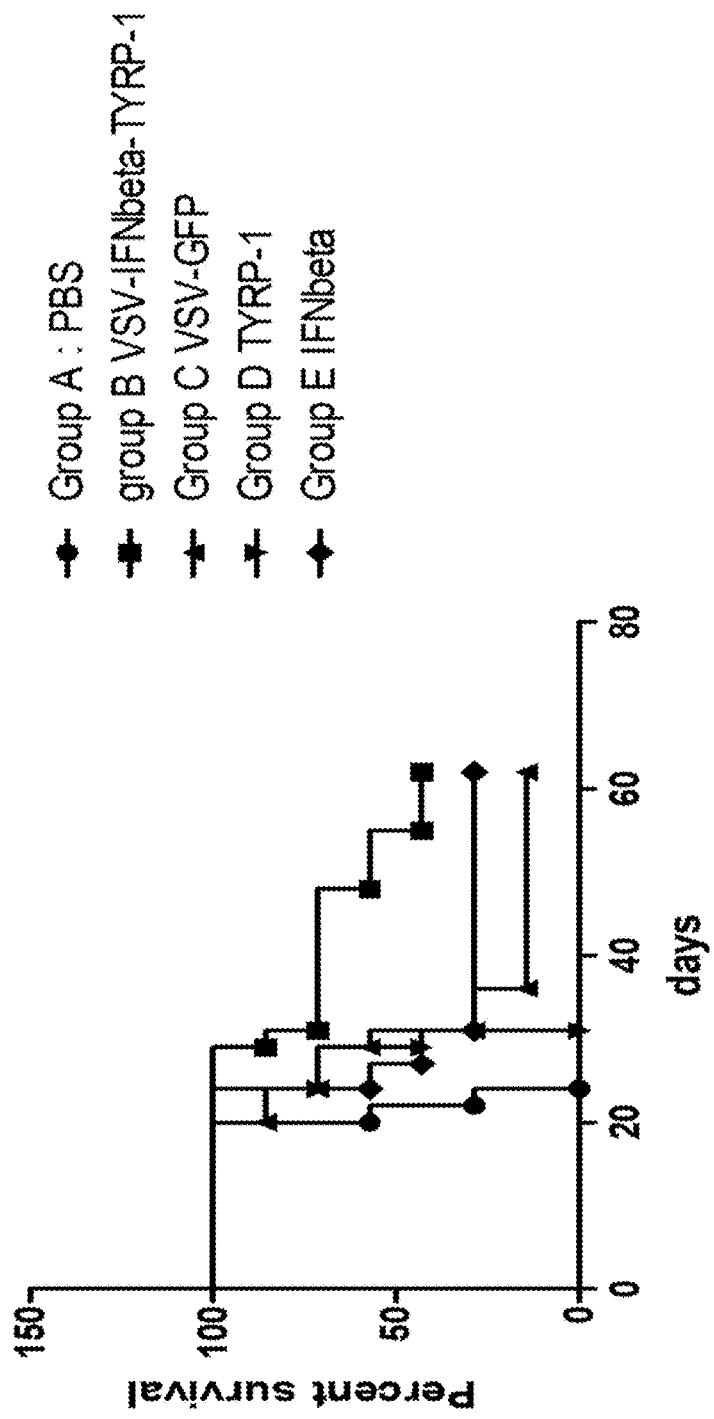

METHODS AND MATERIALS FOR TREATING CANCER

CROSS REFERENCE TO RELATED APPLICATIONS

This application is a National Stage application under 35 U.S.C. § 371 of International Application No. PCT/US2015/021574, having an International Filing Date of Mar. 19, 2015, which claims the benefit of U.S. Provisional Ser. No. 61/955,648 filed Mar. 19, 2014. This disclosure of the prior application is considered part of (and is incorporated by reference in) the disclosure of this application.

SEQUENCE LISTING

The instant application contains a Sequence Listing which has been submitted electronically in ASCII format and is hereby incorporated by reference in its entirety. Said ASCII copy, created on Apr. 19, 2019, is named 1292US1_ST25.txt and is 4,493 bytes in size.

BACKGROUND

1. Technical Field

This document relates to methods and materials for treating cancer. For example, this document relates to methods and materials for using combinations of antigens to treat cancer (e.g., melanoma such as skin melanoma or uveal melanoma, non-Hodgkin lymphoma, colorectal cancer, brain tumors, papillary thyroid carcinoma, non-small-cell lung carcinoma, or adenocarcinoma of the lung).

2. Background Information

Cancer is a serious illness that affects many people every year. In general, there are several common methods for treating cancer: surgery, chemotherapy, radiation therapy, immunotherapy, and biologic therapy. When initially diagnosed with cancer, a cancer specialist such as an oncologist can provide a patient with various cancer treatment options. Typically, an oncologist will recommend the best treatment plan based on the type of cancer, how far it has spread, and other important factors like the age and general health of the patient.

SUMMARY

This document provides methods and materials for treating cancer. For example, this document provides combinations of antigens having the ability to reduce the presence of cancer (e.g., reduce established tumors) within a mammal (e.g., a human). As described herein, combinations of antigens (e.g., a combination of a GNAQ antigen, a TYRP1 antigen, and an N-RAS antigen, a combination of a BRAF antigen, a TOPO-IIα antigen, and a YB-1 antigen, a combination of a TGF-β antigen, a MDR1 antigen, a TYRP-1 antigen, and a KDR2 antigen, a combination of a TOPOIIα antigen, a YB-1 antigen, a CDC7 kinase antigen, and a BRAF antigen, a combination of a TOPOIIα antigen, a YB-1 antigen, a CDC7 kinase antigen, and a CD44 antigen, a combination of a TOPOIIα antigen and an ABCB5α antigen, or a combination of an ABCB5α antigen, a CYT-C antigen, a N-RAS antigen, and a TYRP-1 antigen) can be used to treat cancer (e.g., melanoma such as skin melanoma or uveal melanoma, non-Hodgkin lymphoma, colorectal cancer, brain tumors, papillary thyroid carcinoma, non-small-cell lung carcinoma, or adenocarcinoma of the lung). For example, VSV vectors designed to express a GNAQ antigen, a TYRP1 antigen, and an N-RAS antigen can be used to reduce the number of cancer cells (e.g., uveal melanoma cells) within a mammal (e.g., a human). In some cases, VSV vectors designed to express a BRAF antigen, a TOPO-IIα antigen, and a YB-1 antigen can be used to reduce the number of cancer cells (e.g., skin melanoma cells) within a mammal (e.g., a human). In some cases, the combinations of antigens provided herein (e.g., a combination of a GNAQ antigen, a TYRP1 antigen, and an N-RAS antigen or a combination of a BRAF antigen, a TOPO-IIα antigen, and a YB-1 antigen) can be used to treat cancer a cancer that overexpresses TOPO-IIα, YB-1, TYRP-1, or BRAF.

In general, one aspect of this document features a composition comprising, or consisting essentially of, nucleic acid encoding a GNAQ antigen, a TYRP1 antigen, and an N-RAS antigen, wherein the composition comprises less than 100 separate nucleic acid molecules. The composition can comprise a nucleic acid molecule encoding the GNAQ antigen, a nucleic acid molecule encoding the TYRP1 antigen, and a nucleic acid molecule encoding the N-RAS antigen. The composition can comprise a VSV vector comprising nucleic acid encoding the GNAQ antigen. The composition can comprise a VSV vector comprising nucleic acid encoding the TYRP1 antigen. The composition can comprise a VSV vector comprising nucleic acid encoding the N-RAS antigen. The composition can comprise less than 50 separate nucleic acid molecules. The composition can comprise less than 10 separate nucleic acid molecules. The composition can comprise less than 5 separate nucleic acid molecules.

In another aspect, this document features a method of treating cancer within a mammal. The method comprises, or consists essentially of, administering to the mammal a composition comprising, or consisting essentially of, nucleic acid encoding a GNAQ antigen, a TYRP1 antigen, and an N-RAS antigen, wherein the composition comprises less than 100 separate nucleic acid molecules. The cancer can be a melanoma. The mammal can be a human. The composition can comprise a nucleic acid molecule encoding the GNAQ antigen, a nucleic acid molecule encoding the TYRP1 antigen, and a nucleic acid molecule encoding the N-RAS antigen. The composition can comprise a VSV vector comprising nucleic acid encoding the GNAQ antigen. The composition can comprise a VSV vector comprising nucleic acid encoding the TYRP1 antigen. The composition can comprise a VSV vector comprising nucleic acid encoding the N-RAS antigen. The composition can comprise less than 50 separate nucleic acid molecules. The composition can comprise less than 10 separate nucleic acid molecules. The composition can comprise less than 5 separate nucleic acid molecules.

In another aspect, this document features a composition comprising, or consisting essentially of, nucleic acid encoding a BRAF antigen, a TOPO-IIα antigen, and a YB-1 antigen, wherein the composition comprises less than 100 separate nucleic acid molecules. The composition can comprise a nucleic acid molecule encoding the BRAF antigen, a nucleic acid molecule encoding the TOPO-IIα antigen, and a nucleic acid molecule encoding the YB-1 antigen. The composition can comprise a VSV vector comprising nucleic acid encoding the BRAF antigen. The composition can comprise a VSV vector comprising nucleic acid encoding the TOPO-IIα antigen. The composition can comprise a VSV vector comprising nucleic acid encoding the YB-1 antigen. The composition can comprise less than 50 separate nucleic acid molecules. The composition can comprise less than 10 separate nucleic acid molecules. The composition can comprise less than 5 separate nucleic acid molecules.

In another aspect, this document features a method of treating cancer within a mammal. The method comprises, or consists essentially of, administering to the mammal a composition comprising, or consisting essentially of, nucleic acid encoding a BRAF antigen, a TOPO-IIα antigen, and a YB-1 antigen, wherein the composition comprises less than 100 separate nucleic acid molecules. The cancer can be a melanoma. The mammal can be a human. The composition can comprise a nucleic acid molecule encoding the BRAF antigen, a nucleic acid molecule encoding the TOPO-IIα antigen, and a nucleic acid molecule encoding the YB-1 antigen. The composition can comprise a VSV vector comprising nucleic acid encoding the BRAF antigen. The composition can comprise a VSV vector comprising nucleic acid encoding the TOPO-IIα antigen. The composition can comprise a VSV vector comprising nucleic acid encoding the YB-1 antigen. The composition can comprise less than 50 separate nucleic acid molecules. The composition can comprise less than 10 separate nucleic acid molecules. The composition can comprise less than 5 separate nucleic acid molecules.

In another aspect, this document features a composition comprising, or consisting essentially of, nucleic acid encoding: (a) a TGF-β antigen, a MDR1 antigen, a TYRP-1 antigen, and a KDR2 antigen, (b) a TOPOIIα antigen, a YB-1 antigen, a CDC7 kinase antigen, and a BRAF antigen, (c) a TOPOIIα antigen, a YB-1 antigen, a CDC7 kinase antigen, and a CD44 antigen, (d) a TOPOIIα antigen and an ABCB5α antigen, or (e) an ABCB5α antigen, a CYT-C antigen, a N-RAS antigen, and a TYRP-1 antigen, wherein the composition comprises less than 100 separate nucleic acid molecules. The composition can comprise: (a) a nucleic acid molecule encoding a TGF-β antigen, a nucleic acid molecule encoding a MDR1 antigen, a nucleic acid molecule encoding a TYRP-1 antigen, and a nucleic acid molecule encoding a KDR2 antigen, (b) a nucleic acid molecule encoding a TOPOIIα antigen, a nucleic acid molecule encoding a YB-1 antigen, a nucleic acid molecule encoding a CDC7 kinase antigen, and a nucleic acid molecule encoding a BRAF antigen, (c) a nucleic acid molecule encoding a TOPOIIα antigen, a nucleic acid molecule encoding a YB-1 antigen, a nucleic acid molecule encoding a CDC7 kinase antigen, and a nucleic acid molecule encoding a CD44 antigen, (d) a nucleic acid molecule encoding a TOPOIIα antigen and a nucleic acid molecule encoding an ABCB5α antigen, or (e) a nucleic acid molecule encoding an ABCB5α antigen, a nucleic acid molecule encoding a CYT-C antigen, a nucleic acid molecule encoding a N-RAS antigen, and a nucleic acid molecule encoding a TYRP-1 antigen. The composition can comprise a VSV vector comprising nucleic acid encoding the TGF-β antigen, the MDR1 antigen, the TYRP-1 antigen, the KDR2 antigen, the TOPOIIα antigen, the YB-1 antigen, the CDC7 kinase antigen, the BRAF antigen, the CD44 antigen, the ABCB5α antigen, the CYT-C antigen, or the N-RAS antigen. The composition can comprise less than 50 separate nucleic acid molecules. The composition can comprise less than 10 separate nucleic acid molecules. The composition can comprise less than 6 separate nucleic acid molecules.

In another aspect, this document features a method of treating cancer within a mammal. The method comprises, or consists essentially of, administering to the mammal a composition of the preceding paragraph. The cancer can be a melanoma. The mammal can be a human.

In another aspect, this document features a composition comprising, or consisting essentially of, nucleic acid encoding a TGF-β antigen, a KDR2 antigen, a P Glyc antigen, and a TYRP-1 antigen, wherein the composition comprises less than 100 separate nucleic acid molecules. The composition can comprise a nucleic acid molecule encoding the TGF-β antigen, a nucleic acid molecule encoding the KDR2 antigen, a nucleic acid molecule encoding the P Glyc antigen, and a nucleic acid molecule encoding the TYRP-1 antigen. The composition can comprise a VSV vector comprising nucleic acid encoding the TGF-β antigen. The composition can comprise a VSV vector comprising nucleic acid encoding the KDR2 antigen. The composition can comprise a VSV vector comprising nucleic acid encoding the P Glyc antigen. The composition can comprise a VSV vector comprising nucleic acid encoding the TYRP1 antigen. The composition can comprise less than 50 separate nucleic acid molecules. The composition can comprise less than 10 separate nucleic acid molecules. The composition can comprise less than 5 separate nucleic acid molecules.

In another aspect, this document features a method of treating cancer within a mammal, wherein the method comprises administering to the mammal a composition comprising nucleic acid encoding a TGF-β antigen, a KDR2 antigen, a P Glyc antigen, and a TYRP-1 antigen, wherein the composition comprises less than 100 separate nucleic acid molecules. The cancer can be a melanoma. The mammal can be a human.

In another aspect, this document features a composition of any one of the above recited paragraphs, wherein the composition comprises an immune checkpoint inhibitor. The immune checkpoint inhibitor can be an anti-PD-1 antibody or an anti-CTLA4 antibody.

In another aspect, this document features a method of any one of the above recited paragraphs, wherein the method comprises administering an immune checkpoint inhibitor to the mammal. The immune checkpoint inhibitor can be an anti-PD-1 antibody or an anti-CTLA4 antibody.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 5. VSV-TAA therapy of intracranial GL261 tumors. C57BL/6 mice bearing 5 day established i.c. GL261 tumors were treated intravenously with a total of $5\times10^6$ pfu of (VSV-HIF-2α, VSV-SOX-10, and VSV-c-MYC); (VSV-HIF-2α, VSV-SOX-10, and VSV-GFP); (VSV-N-RAS, VSV-CYT-C, and VSV-TYRP-1), or (VSV-GFP) on days 6, 8, 10, 13, 15, 17, 20, 22, 24, 27, 29, and 31. Survival with time is shown.

FIG. 7. Anti-PD1 checkpoint inhibition uncovers a Th1 IFN-γ anti-tumor response. A. Splenocytes and lymph nodes were pooled from 3 C57BL/6 mice per group bearing 5 day established i.c. GL261 tumors treated with either (VSV-HIF-2α, VSV-SOX-10, and VSV-c-MYC+IgG) or (VSV-HIF-2α, VSV-SOX-10, and VSV-c-MYC+anti-PD1 antibody). Cells were plated at $1\times10^6$ cells per well and re-stimulated in vitro 3 times at 24 hour intervals with $1\times10^5$ cells of freeze thaw lysates of GL261 tumors recovered from mice bearing i.c. GL261 tumors (lanes 1 and 2, and 3 and 4). The same experiment also was carried out with splenocytes and lymph node cells depleted of Treg cells (lanes 5 and 6, and 7 and 8). Following 48 hours of culture, supernatants were assayed for IFN-γ (A) or IL-17 (B) by ELISA. Results are representative of 3 separate measurements. Error bars are expressed as standard deviation (SD).

FIG. 14 is contains sequence information for a truncated VSV-N-RAS virus recovered from an ASMEL.

FIG. 15 is contains sequence information for a truncated VSV-CYT-C virus recovered from an ASMEL.

FIG. 17 is a graph plotting the percent survival of mice having s.c. B16 tumors and treated with the indicated VSV vectors.

FIG. 21 is a graph plotting the percent survival of mice having B16 tumors and treated with the indicated VSV vectors.

DETAILED DESCRIPTION

Figure 1:
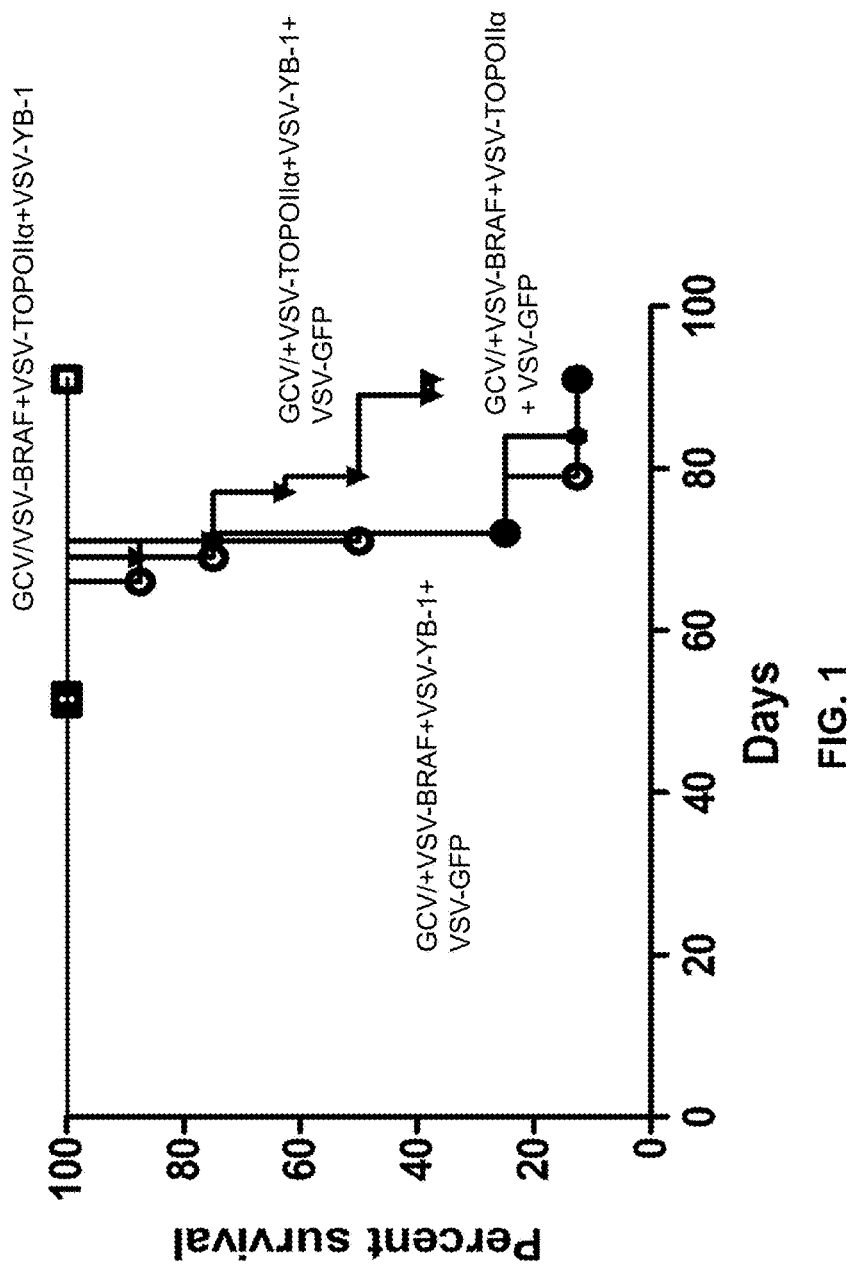
FIG. 1 is a graph plotting the percent survival of mice from B16 recurrences that escaped frontline ganciclovir (GCV) treatment. The mice were treated with the indicated combinations of VSV vectors.

This document provides methods and materials for treating cancer. For example, this document provides combinations of antigens having the ability to reduce the number of cancer cells within a mammal (e.g., a human). As described herein, combinations of antigens that include a GNAQ antigen, a TYRP1 antigen, and an N-RAS antigen, that include a BRAF antigen, a TOPO-IIα antigen, and a YB-1 antigen, that include a TGF-β antigen, a MDR1 antigen, a TYRP-1 antigen, and a KDR2 antigen, that include a TOPOIIα antigen, a YB-1 antigen, a CDC7 kinase antigen, and a BRAF antigen, that include a TOPOIIα antigen, a YB-1 antigen, a CDC7 kinase antigen, and a CD44 antigen, that include a TOPOIIα antigen and an ABCB5α antigen, that include an ABCB5α antigen, a CYT-C antigen, a N-RAS antigen, and a TYRP-1 antigen, or that include a TGF-β antigen, a KDR2 antigen, a P glycoprotein (P Glyc) antigen, and a TYRP-1 antigen can be used to treat cancer. In some cases, combinations of antigens that include a GNAQ antigen, a TYRP1 antigen, and an N-RAS antigen, that include a BRAF antigen, a TOPO-IIα antigen, and a YB-1 antigen, that include a TGF-β antigen, a MDR1 antigen, a TYRP-1 antigen, and a KDR2 antigen, that include a TOPOIIα antigen, a YB-1 antigen, a CDC7 kinase antigen, and a BRAF antigen, that include a TOPOIIα antigen, a YB-1 antigen, a CDC7 kinase antigen, and a CD44 antigen, that include a TOPOIIα antigen and an ABCB5α antigen, that include an ABCB5α antigen, a CYT-C antigen, a N-RAS antigen, and a TYRP-1 antigen, or that include a TGF-β antigen, a KDR2 antigen, a P Glyc antigen, and a TYRP-1 antigen can be used to reduce the number of cancer cells present within a mammal.

The methods and materials provided herein can be used to treat cancer or to reduce the number of cancer cells present within any appropriate mammal such as humans, monkeys, horses, cows, sheep, dogs, cats, mice, or rats. In addition, the methods and materials provided herein can be used to treat any appropriate cancer or to reduce the number of appropriate type of cancer cells present within a mammal. For example, the methods and materials provided herein can be used to treat melanoma (e.g., skin melanoma or uveal melanoma), non-Hodgkin lymphoma, colorectal cancer, brain tumors, papillary thyroid carcinoma, non-small-cell lung carcinoma, or adenocarcinoma of the lung or can be used to reduce the number of melanoma (e.g., skin melanoma or uveal melanoma), non-Hodgkin lymphoma, colorectal cancer, brain tumor, papillary thyroid carcinoma, non-small-cell lung carcinoma, or adenocarcinoma of the lung cancer cells present within a mammal.

In some cases, a combination of a GNAQ antigen, a TYRP1 antigen, and an N-RAS antigen can be used to treat cancer (e.g., melanoma such as uveal melanoma). In some cases, one or more viral vectors (e.g., vesicular stomatitis virus (VSV) vectors) designed to express a GNAQ antigen, a TYRP1 antigen, and an N-RAS antigen can be used to treat cancer (e.g., melanoma such as uveal melanoma). For example, VSV vectors designed to express a GNAQ antigen, a TYRP1 antigen, and an N-RAS antigen can be administered to a mammal (e.g., a human) with uveal melanoma to reduce the size or to prevent the additional growth of that melanoma.

In some cases, a combination of a BRAF antigen, a TOPO-IIα antigen, and a YB-1 antigen can be used to treat cancer (e.g., melanoma such as skin melanoma). In some cases, one or more viral vectors (e.g., VSV vectors) designed to express a BRAF antigen, a TOPO-IIα antigen, and a YB-1 antigen can be used to treat cancer (e.g., melanoma such as skin melanoma). For example, VSV vectors designed to express a BRAF antigen, a TOPO-IIα antigen, and a YB-1 antigen can be administered to a mammal (e.g., a human) with skin melanoma to reduce the size or to prevent the additional growth of that melanoma.

In some cases, a combination of a TGF-β antigen, a MDR1 antigen, a TYRP-1 antigen, and a KDR2 antigen can be used to treat cancer (e.g., melanoma). In some cases, one or more viral vectors (e.g., VSV vectors) designed to express a TGF-β antigen, a MDR1 antigen, a TYRP-1 antigen, and a KDR2 antigen can be used to treat cancer (e.g., melanoma).

In some cases, a combination of a TOPOIIα antigen, a YB-1 antigen, a CDC7 kinase antigen, and a BRAF antigen can be used to treat cancer (e.g., melanoma, colorectal cancer, prostate cancer, ovarian cancer, or breast cancer). In some cases, one or more viral vectors (e.g., VSV vectors) designed to express a TOPOIIα antigen, a YB-1 antigen, a CDC7 kinase antigen, and a BRAF antigen can be used to treat cancer (e.g., melanoma, colorectal cancer, prostate cancer, ovarian cancer, or breast cancer).

In some cases, a combination of a TOPOIIα antigen, a YB-1 antigen, a CDC7 kinase antigen, and a CD44 antigen can be used to treat cancer (e.g., melanoma or prostate cancer). In some cases, one or more viral vectors (e.g., VSV vectors) designed to express a TOPOIIα antigen, a YB-1 antigen, a CDC7 kinase antigen, and a CD44 antigen can be used to treat cancer (e.g., melanoma or prostate cancer).

In some cases, a combination of a TOPOIIα antigen and an ABCB5α antigen can be used to treat cancer (e.g., melanoma). In some cases, one or more viral vectors (e.g., VSV vectors) designed to express a TOPOIIα antigen and an ABCB5α antigen can be used to treat cancer (e.g., melanoma).

In some cases, a combination of an ABCB5α antigen, a CYT-C antigen, an N-RAS antigen, and a TYRP-1 antigen can be used to treat cancer (e.g., melanoma). In some cases, one or more viral vectors (e.g., VSV vectors) designed to express an ABCB5α antigen, a CYT-C antigen, a NRAS antigen, and a TYRP-1 antigen can be used to treat cancer (e.g., melanoma).

In some cases, a combination of a TGF-β antigen, a KDR2 antigen, a P glycoprotein (P Glyc) antigen, and a TYRP-1 antigen can be used to treat cancer (e.g., melanoma). In some cases, one or more viral vectors (e.g., VSV vectors) designed to express a TGF-β antigen, a KDR2 antigen, a P glycoprotein (P Glyc) antigen, and a TYRP-1 antigen can be used to treat cancer (e.g., melanoma).

A GNAQ (guanine nucleotide binding protein, q polypeptide) antigen can have the amino acid sequence set forth in GenBank® Accession No. AF493896.1 (GI No. 20147684) or U40038.1 (GI No. 1181670), or a fragment of such an amino acid sequence that is between about 7 and 150 amino acid residues (e.g., between about 10 and 100 amino acid residues, between about 15 and 50 amino acid residues, between about 20 and 75 amino acid residues, between about 25 and 50 amino acid residues, between about 30 and 60 amino acid residues, or between about 30 and 50 amino acid residues) in length.

A TYRP1 (tyrosinase-related protein 1) antigen can have the amino acid sequence set forth in GenBank® Accession No. CAG28611 (GI No. 47115303), NM_000550.2 (GI No. 169881242), CR407683.1 (GI No. 47115302), XM_005251574.1 (GI No. 530390132), or X51420.1 (GI No. 37512), or a fragment of such an amino acid sequence that is between about 7 and 527 amino acid residues (e.g., between about 10 and 527 amino acid residues, between about 15 and 527 amino acid residues, between about 20 and 527 amino acid residues, between about 25 and 527 amino acid residues, between about 30 and 527 amino acid residues, or between about 30 and 200 amino acid residues) in length.

An N-RAS (neuroblastoma RAS viral oncogene homolog) antigen can have the amino acid sequence set forth in GenBank® Accession No. AAB29640 (GI No. 544859), or a fragment of such an amino acid sequence that is between about 7 and 400 amino acid residues (e.g., between about 10 and 400 amino acid residues, between about 15 and 400 amino acid residues, between about 20 and 400 amino acid residues, between about 25 and 400 amino acid residues, between about 30 and 400 amino acid residues, or between about 30 and 200 amino acid residues) in length. In some cases, an N-RAS antigen can have the amino acid sequence set forth in GenBank® Accession No. NM_002524.4 (GI No. 334688826) or AF493919.1 (GI No. 20147730), or a fragment of such an amino acid sequence that is between about 7 and 400 amino acid residues (e.g., between about 10 and 400 amino acid residues, between about 15 and 400 amino acid residues, between about 20 and 400 amino acid residues, between about 25 and 400 amino acid residues, between about 30 and 400 amino acid residues, or between about 30 and 200 amino acid residues) in length.

A BRAF (v-raf murine sarcoma viral oncogene homolog B) antigen can have the amino acid sequence set forth in GenBank® Accession No. NM_004333.4 (GI No. 187608632), or a fragment of such an amino acid sequence that is between about 7 and 150 amino acid residues (e.g., between about 10 and 100 amino acid residues, between about 15 and 50 amino acid residues, between about 20 and 75 amino acid residues, between about 25 and 50 amino acid residues, between about 30 and 60 amino acid residues, or between about 30 and 50 amino acid residues) in length. In some cases, a GNAQ antigen can have the amino acid sequence set forth in GenBank® Accession No. XM_005250045.1 (GI No. 530387105), XM_005250046.1 (GI No. 530387107), or XM_005250047.1 (GI No. 530387109), or a fragment of such an amino acid sequence that is between about 7 and 150 amino acid residues (e.g., between about 10 and 100 amino acid residues, between about 15 and 50 amino acid residues, between about 20 and 75 amino acid residues, between about 25 and 50 amino acid residues, between about 30 and 60 amino acid residues, or between about 30 and 50 amino acid residues) in length.

A TOPO-IIα (DNA topoisomerase 2-alpha) antigen can have the amino acid sequence set forth in GenBank® Accession No. NM_001067.3 (GI No. 300193028), or a fragment of such an amino acid sequence that is between about 7 and 150 amino acid residues (e.g., between about 10 and 100 amino acid residues, between about 15 and 50 amino acid residues, between about 20 and 75 amino acid residues, between about 25 and 50 amino acid residues, between about 30 and 60 amino acid residues, or between about 30 and 50 amino acid residues) in length.

A YB-1 (Y box binding protein 1) antigen can have the amino acid sequence set forth in GenBank® Accession No. NM_004559.3 (GI No. 109134359), or a fragment of such an amino acid sequence that is between about 7 and 150 amino acid residues (e.g., between about 10 and 100 amino acid residues, between about 15 and 50 amino acid residues, between about 20 and 75 amino acid residues, between about 25 and 50 amino acid residues, between about 30 and 60 amino acid residues, or between about 30 and 50 amino acid residues) in length. In some cases, a GNAQ antigen can have the amino acid sequence set forth in GenBank® Accession No. BC071708.1 (GI No. 47940505) or XM_005270904.1 (GI No. 530362706), or a fragment of such an amino acid sequence that is between about 7 and 150 amino acid residues (e.g., between about 10 and 100 amino acid residues, between about 15 and 50 amino acid residues, between about 20 and 75 amino acid residues, between about 25 and 50 amino acid residues, between about 30 and 60 amino acid residues, or between about 30 and 50 amino acid residues) in length.

A TGF-β antigen can have the amino acid sequence set forth in GenBank® Accession No. X02812 or J05114 (GI No. 37092), or a fragment of such an amino acid sequence that is between about 7 and 150 amino acid residues (e.g., between about 10 and 100 amino acid residues, between about 15 and 50 amino acid residues, between about 20 and 75 amino acid residues, between about 25 and 50 amino acid residues, between about 30 and 60 amino acid residues, or between about 30 and 50 amino acid residues) in length.

A MDR1 antigen can have the amino acid sequence set forth in GenBank® Accession No. X58723 or X59732 (GI No. 34522), or a fragment of such an amino acid sequence that is between about 7 and 150 amino acid residues (e.g., between about 10 and 100 amino acid residues, between about 15 and 50 amino acid residues, between about 20 and 75 amino acid residues, between about 25 and 50 amino acid residues, between about 30 and 60 amino acid residues, or between about 30 and 50 amino acid residues) in length.

A KDR2 antigen can have the amino acid sequence set forth in GenBank® Accession No. AF063658 (GI No. 3132832), or a fragment of such an amino acid sequence that is between about 7 and 150 amino acid residues (e.g., between about 10 and 100 amino acid residues, between about 15 and 50 amino acid residues, between about 20 and 75 amino acid residues, between about 25 and 50 amino acid residues, between about 30 and 60 amino acid residues, or between about 30 and 50 amino acid residues) in length.

A CYT-C antigen can have the amino acid sequence set forth in GenBank® Accession No. NP_061820 (GI No. 11128019), or a fragment of such an amino acid sequence that is between about 7 and 150 amino acid residues (e.g., between about 10 and 100 amino acid residues, between about 15 and 50 amino acid residues, between about 20 and 75 amino acid residues, between about 25 and 50 amino acid residues, between about 30 and 60 amino acid residues, or between about 30 and 50 amino acid residues) in length.

An ABCB5α antigen can have the amino acid sequence set forth in GenBank® Accession Nos. NM_029961, XM_001002680, or XM_906632 (GI No. 255708374), NM_001163941.1 (GI No. 255708476), NM_178559.5 (GI No. 255708475), NM_001163942.1 (GI No. 255708370), or NM_001163993.2 (GI No. 574957217), or a fragment of such an amino acid sequence that is between about 7 and 150 amino acid residues (e.g., between about 10 and 100 amino acid residues, between about 15 and 50 amino acid residues, between about 20 and 75 amino acid residues, between about 25 and 50 amino acid residues, between about 30 and 60 amino acid residues, or between about 30 and 50 amino acid residues) in length.

A CDC7 kinase antigen can have the amino acid sequence set forth in GenBank® Accession No. NM_009863 (GI No. 409168309), NM_001134420.1 (GI No. 197313666), NM_003503.3 (GI No. 197313663), or NM_001134419.1 (GI No. 197313664), or a fragment of such an amino acid sequence that is between about 7 and 150 amino acid residues (e.g., between about 10 and 100 amino acid residues, between about 15 and 50 amino acid residues, between about 20 and 75 amino acid residues, between about 25 and 50 amino acid residues, between about 30 and 60 amino acid residues, or between about 30 and 50 amino acid residues) in length.

A CD44 antigen can have the amino acid sequence set forth in GenBank® Accession No. NM_001177787 (GI No. 295293147), AY101193.1 (GI No. 21429240), or AY101192.1 (GI No. 21429238), or a fragment of such an amino acid sequence that is between about 7 and 150 amino acid residues (e.g., between about 10 and 100 amino acid residues, between about 15 and 50 amino acid residues, between about 20 and 75 amino acid residues, between about 25 and 50 amino acid residues, between about 30 and 60 amino acid residues, or between about 30 and 50 amino acid residues) in length.

A P Glyc (P glycoprotein) antigen can have the amino acid sequence set forth in GenBank® Accession No. M23234.1 (GI No. 187501), AY234788.1 (GI No. 34539754), AY425006.1 (GI No. 40795902), AF399931.1 (GI No. 33307711), or EU854148.1 (GI No. 194740429), or a fragment of such an amino acid sequence that is between about 7 and 150 amino acid residues (e.g., between about 10 and 100 amino acid residues, between about 15 and 50 amino acid residues, between about 20 and 75 amino acid residues, between about 25 and 50 amino acid residues, between about 30 and 60 amino acid residues, or between about 30 and 50 amino acid residues) in length.

In some cases, a GNAQ, TYRP1, N-RAS, BRAF, TOPO-IIα, YB-1, MDR1, KDR2, CYT-C, ABCB5α, P Glyc, CDC7 kinase, CD44, or TGF-β antigen can have the amino acid sequence set forth in one of the GenBank® Accession numbers indicated above or a fragment of such an amino acid sequence that is immunogenic and induces a robust IL-17 response. In some cases, such an antigen can include one or more mutations within the sequence provided in GenBank® provided that the mutant antigen induces a robust IL-17 response. In some cases, a GNAQ, TYRP1, N-RAS, BRAF, TOPO-IIα, YB-1, MDR1, KDR2, CYT-C, ABCB5α, P Glyc, CDC7 kinase, CD44, or TGF-β antigen can have the amino acid sequence (or a fragment thereof) as found in a naturally-occurring mutated form. For example, a GNAQ antigen having the amino acid sequence (or a fragment thereof) as found in a naturally-occurring mutated form can have one or more of the following mutations: GNAQ (209) or GNAQ (R183). A TYRP1 antigen having the amino acid sequence (or a fragment thereof) as found in a naturally-occurring mutated form can have one or more of the following mutations: 1-BP DEL of 368A (condition: albinism, oculocutaneous, type III), SER166TER (dbSNP: rs104894130), ARG373TER, ARG356GLU, 1-BP DEL of 106T, 4-BP DEL of 1057AACA, or ARG93CYS (condition: albinism, oculocutaneous, type III). An N-RAS antigen having the amino acid sequence (or a fragment thereof) as found in a naturally-occurring mutated form can have one or more of the following mutations: Q61 (dbSNP: rs11554290), GLY13ASP (dbSNP: rs121434596), GLY13ARG (dbSNP: rs121434595), THRSOILE, GLY60GLU (condition: Noonen syndrome 6), PRO34LEU, or GLY12ASP (condition: epidermal nevus, somatic). A BRAF antigen having the amino acid sequence (or a fragment thereof) as found in a naturally-occurring mutated form can have the following mutation: V600 (dbSNP: rs113488022). A TOPO-IIα antigen having the amino acid sequence (or a fragment thereof) as found in a naturally-occurring mutated form can have the following mutation: ARG486LYS (condition: resistance to inhibition of or by amsacrine). A YB-1 antigen having the amino acid sequence (or a fragment thereof) as found in a naturally-occurring mutated form can have the following mutation: YB-1 (S102). A MDR1 antigen having the amino acid sequence (or a fragment thereof) as found in a naturally-occurring mutated form can have one or more of the following mutations: G2677T, C3435T (dbSNP: rs1045642), GLY185VAL (dbSNP: rs1128501; condition: colchicine resistance), or ALA893SER/THR (condition: inflammatory bowel disease). A KDR2 antigen having the amino acid sequence (or a fragment thereof) as found in a naturally-occurring mutated form can have one or more of the following mutations: D717V, T771R, PRO1147SER (condition: hemangioma, capillary infantile, somatic), or CYS482ARG (dbSNP: rs34231037; condition susceptibility to hemangioma or capillary infantile). An ABCB5α antigen having the amino acid sequence (or a fragment thereof) as found in a naturally-occurring mutated form can have one or more of the following mutations: G347R, M521L, P580S, or A687S. A CDC7 kinase antigen having the amino acid sequence (or a fragment thereof) as found in a naturally-occurring mutated form can have the following mutation:

L2101. A CD44 antigen having the amino acid sequence (or a fragment thereof) as found in a naturally-occurring mutated form can have the following mutation: ARG46PRO (dbSNP: rs121909545; condition: Indian blood group system polymorphism). A TGF-β antigen having the amino acid sequence (or a fragment thereof) as found in a naturally-occurring mutated form can have one or more of the following mutations: CYS225ARG (dbSNP: rs104894719), ARG218HIS (dbSNP: rs104894720), ARG218CYS (dbSNP: rs104894721), TYR81HIS (dbSNP: rs111033611), CYS223ARG (dbSNP: rs104894722), CYS223GLY (dbSNP: rs104894722; condition: camurati-engelmann disease), or LEU10PRO (conditions: cystic fibrosis lung disease, modifier of invasive breast cancer, or susceptibilities thereto).

In some cases, a GNAQ, TYRP1, N-RAS, BRAF, TOPO-IIα, YB-1, MDR1, KDR2, CYT-C, ABCB5α, P Glyc, CDC7 kinase, CD44, or TGF-β antigen can have an amino acid sequence that is truncated at the C terminus. For example, a GNAQ antigen can include the N-terminal sequence of a full length GNAQ polypeptide, while lacking a portion of the C-terminal sequence of a full length GNAQ polypeptide. In some cases, the length of the missing C-terminal sequence of a truncated antigen (e.g., a truncated GNAQ, TYRP1, N-RAS, BRAF, TOPO-IIα, YB-1, MDR1, KDR2, CYT-C, ABCB5α, P Glyc, CDC7 kinase, CD44, or TGF-β antigen) can be from 1 to about 300 (e.g., 1 to 275, 1 to 250, 1 to 225, 1 to 200, 1 to 175, 1 to 150, 1 to 125, 1 to 100, 1 to 75, 1 to 50, 1 to 25, 1 to 20, 1 to 15, 1 to 10, 5 to 275, 5 to 250, 5 to 225, 5 to 200, 5 to 175, 5 to 150, 5 to 125, 5 to 100, 5 to 75, 5 to 50, 5 to 25, 5 to 20, 5 to 15, 5 to 10, 10 to 275, 10 to 250, 10 to 225, 10 to 200, 10 to 175, 10 to 150, 10 to 125, 10 to 100, 10 to 75, 10 to 50, 10 to 25, 10 to 20, or 10 to 15) amino acid residues. In some cases, the length of the missing C-terminal sequence of a truncated antigen (e.g., a truncated GNAQ, TYRP1, N-RAS, BRAF, TOPO-IIα, YB-1, MDR1, KDR2, CYT-C, ABCB5α, P Glyc, CDC7 kinase, CD44, or TGF-β antigen) can be between about 0.01 percent to about 85 percent (e.g., about 0.01 percent to about 85 percent, about 0.01 percent to about 75 percent, about 0.01 percent to about 65 percent, about 0.01 percent to about 55 percent, about 0.01 percent to about 45 percent, about 0.01 percent to about 35 percent, about 0.01 percent to about 25 percent, about 0.01 percent to about 15 percent, about 0.01 percent to about 10 percent, about 0.01 percent to about 5 percent, about 0.1 percent to about 85 percent, about 1 percent to about 85 percent, about 5 percent to about 85 percent, about 5 percent to about 85 percent, about 5 percent to about 75 percent, about 5 percent to about 65 percent, about 5 percent to about 55 percent, about 5 percent to about 45 percent, about 5 percent to about 35 percent, about 5 percent to about 25 percent, about 5 percent to about 15 percent, about 5 percent to about 10 percent) of the length of the full length polypeptide.

In some cases, the combination of antigens used to treat cancer or reduce the number of cancer cells within a mammal (e.g., a human) can be antigens of another species (e.g., mouse, rat, pig, monkey, sheep, cow, dog, or cat). For example, a combination of mouse, rat, or monkey antigens can be used to treat cancer or reduce the number of cancer cells within a human. Examples of GNAQ sequences from mouse are set forth in GenBank® Accession Nos. NM_008139.5 (GI No. 145966786) and BC057583.1 (GI No. 34785834). Examples of TYRP-1 sequences from mouse are set forth in GenBank® Accession Nos. NM_001282014.1 (GI No. 530537243), NM_031202.3 (GI No. 530537240), and NM_001282015.1 (GI No. 530537245). Examples of N-RAS sequences from mouse are set forth in GenBank® Accession Nos. NM_010937.2, NC_000069.6 (GI No. 372099107), and AC_000025.1 (GI No. 83280973). An example of a BRAF sequence from mouse is set forth in GenBank® Accession No. NM_139294.5 (GI No. 153791903). An example of a TOPO-IIα sequence from mouse is set forth in GenBank® Accession No. NM011623. An example of a YB-1 sequence from mouse is set forth in GenBank® Accession No. M62867 (GI No. 199820). An example of a TGF-β sequence from mouse is set forth in GenBank® Accession No. M13177.1 (GI No. 201952). An example of a MDR1 sequence from mouse is set forth in GenBank® Accession No. NM_011075 (GI No. 161169006). An example of a KDR2 sequence from mouse is set forth in GenBank® Accession No. EU884114.1 (GI No. 215400615). An example of a YB-1 sequence from mouse is set forth in GenBank® Accession No. X57621.1 (GI No. 55450), C061634.1 (GI No. 38197294), or NM_011732.2 (GI No. 113205058). An example of a P Glyc sequence from mouse is set forth in GenBank® Accession No. M33581.1 (GI No. 199104), JQ655148.1 (GI No. 406817019), M24417.1 (GI No. 2000329), or AY864315.1 (GI No. 57791235).

Any appropriate vector (e.g. a viral vector) can be used to deliver nucleic acid encoding a GNAQ, TYRP1, N-RAS, BRAF, TOPO-IIα, YB-1, MDR1, KDR2, CYT-C, ABCB5α, P Glyc, CDC7 kinase, CD44, or TGF-β antigen (or combination thereof) to cells of a mammal to treat cancer as described herein. For example, viral vectors for administering nucleic acids (e.g., a nucleic acid encoding a GNAQ, TYRP1, N-RAS, BRAF, TOPO-IIα, YB-1, MDR1, KDR2, CYT-C, ABCB5α, P Glyc, CDC7 kinase, CD44, or TGF-β antigen (or combination thereof)) to a mammal can be prepared using standard materials (e.g., packaging cell lines, helper viruses, and vector constructs). See, for example, *Gene Therapy Protocols* (*Methods in Molecular Medicine*), edited by Jeffrey R. Morgan, Humana Press, Totowa, N.J. (2002) and *Viral Vectors for Gene Therapy: Methods and Protocols*, edited by Curtis A. Machida, Humana Press, Totowa, N.J. (2003). A viral vector for delivering nucleic acid encoding a GNAQ, TYRP1, N-RAS, BRAF, TOPO-IIα, YB-1, MDR1, KDR2, CYT-C, ABCB5α, P Glyc, CDC7 kinase, CD44, or TGF-β antigen (or combination thereof) can be derived from, for example, animal viruses such as adenoviruses, adeno-associated viruses, retroviruses, lentiviruses, vaccinia viruses, vesicular stomatitis virus, herpes viruses, maraba virus, or papilloma viruses. In some cases, lentiviral vectors, vesicular stomatitis viral vectors, adenoviral vectors, adeno-associated viral vectors, or maraba viral vectors can be used to deliver nucleic acid encoding a GNAQ, TYRP1, N-RAS, BRAF, TOPO-IIα, YB-1, MDR1, KDR2, CYT-C, ABCB5α, P Glyc, CDC7 kinase, CD44, or TGF-β antigen (or combination thereof) to cells of a mammal to treat cancer as described herein. In some cases, VSV-IFNβ (e.g., human interferon) viral vectors such as those described elsewhere (Obuchi et al., *J. Virol.*, 77(16): 8843-56 (2003) and Jenks et al., *Hum. Gene Ther.*, 21(4): 451-62 (2010)) can be used to deliver nucleic acid encoding a GNAQ, TYRP1, N-RAS, BRAF, TOPO-IIα, YB-1, MDR1, KDR2, CYT-C, ABCB5α, P Glyc, CDC7 kinase, CD44, or TGF-β antigen (or combination thereof) to cells of a mammal to treat cancer.

Any appropriate method can be used to insert nucleic acid encoding a GNAQ, TYRP1, N-RAS, BRAF, TOPO-IIα, YB-1, MDR1, KDR2, CYT-C, ABCB5α, P Glyc, CDC7 kinase, CD44, or TGF-β antigen into a viral vector (e.g., a VSV vector). For example, the methods and materials described elsewhere (Kottke et al., *Nature Med.*, 17:854-9 (2011); and Pulido et al., *Nat. Biotechnol.*, 30:337-43 (2012)) can be used to insert nucleic acid encoding a GNAQ, TYRP1, N-RAS, BRAF, TOPO-IIα, YB-1, MDR1, KDR2, CYT-C, ABCB5α, P Glyc, CDC7 kinase, CD44, or TGF-β antigen into a VSV vector such that the antigen (e.g., the GNAQ, TYRP1, N-RAS, BRAF, TOPO-IIα, YB-1, MDR1, KDR2, CYT-C, ABCB5α, P Glyc, CDC7 kinase, CD44, or TGF-β antigen) is expressed in mammalian cells. Once obtained, a combination of VSV vectors having the ability to express a GNAQ antigen, a TYRP1 antigen, and an N-RAS antigen, a BRAF antigen, a TOPO-IIα antigen, and a YB-1 antigen, a TGF-β antigen, a MDR1 antigen, a TYRP-1 antigen, and a KDR2 antigen, a TOPOIIα antigen, a YB-1 antigen, a CDC7 kinase antigen, and a BRAF antigen, a TOPOIIα antigen, a YB-1 antigen, a CDC7 kinase antigen, and a CD44 antigen, a TOPOIIα antigen and an ABCB5α antigen, a TGF-β antigen, a KDR2 antigen, a P Glyc antigen, and a TYRP-1 antigen, or an ABCB5α antigen, a CYT-C antigen, a N-RAS antigen, and a TYRP-1 antigen (e.g., a combination of VSV-GNAQ, VSV-TYRP1, and VSV-N-RAS vectors, a combination of VSV-BRAF, VSV-TOPO-IIα, and VSV-YB-1 vectors, a combination of VSV-TGF-β, VSV-MDR1, VSV-TYRP-1, and VSV-KDR2 vectors, a combination of VSV-TOPOIIα, VSV-YB-1, VSV-CDC7 kinase, and VSV-BRAF vectors, a combination of VSV-TOPOIIα, VSV-YB-1, VSV-CDC7 kinase, and VSV-CD44 vectors, a combination of VSV-TOPOIIα and VSV-ABCB5α vectors, a combination of VSV-TGF-β, VSV-KDR2, VSV-PGlyc, and VSV-TYRP-1 vectors, or a combination of VSV-ABCB5α, VSV-CYT-C, VSV-N-RAS, and VSV-TYRP-1 vectors) can be administered to a mammal to treat cancer (e.g., melanoma such as uveal melanoma) or to reduce the number of cancer cells (e.g., melanoma cells such as uveal melanoma cells) present within a mammal. For example, once obtained, a combination of VSV vectors having the ability to express a BRAF antigen, a TOPO-IIα antigen, and a YB-1 antigen (e.g., a combination of VSV-BRAF, VSV-TOPO-IIα, and VSV-YB-1 vectors) can be administered to a mammal to treat cancer (e.g., melanoma such as skin melanoma) or to reduce the number of cancer cells (e.g., melanoma cells such as skin melanoma cells) present within a mammal.

Any appropriate method can be used to administer viral vectors (e.g., VSV vectors) designed to express a GNAQ antigen, a TYRP1 antigen, and an N-RAS antigen, a BRAF antigen, a TOPO-IIα antigen, and a YB-1 antigen, a TGF-β antigen, a MDR1 antigen, a TYRP-1 antigen, and a KDR2 antigen, a TOPOIIα antigen, a YB-1 antigen, a CDC7 kinase antigen, and a BRAF antigen, a TOPOIIα antigen, a YB-1 antigen, a CDC7 kinase antigen, and a CD44 antigen, a TOPOIIα antigen and an ABCB5α antigen, a TGF-β antigen, a KDR2 antigen, a P Glyc antigen, and a TYRP-1 antigen, or an ABCB5α antigen, a CYT-C antigen, a N-RAS antigen, and a TYRP-1 antigen to a mammal having cancer. For example, intratumoral, subcutaneous, intravenous, intraperitoneal, and intradermal administrations can be used to administer viral vectors (e.g., VSV vectors) designed to express a GNAQ antigen, a TYRP1 antigen, and an N-RAS antigen to a mammal having cancer (e.g., uveal melanoma) or viral vectors (e.g., VSV vectors) designed to express a BRAF antigen, a TOPO-IIα antigen, and a YB-1 antigen to a mammal having cancer (e.g., skin melanoma). Once the viral vectors are administered to a mammal, the mammal can be monitored to confirm a reduction in the number of cancer cells present within the mammal. For example, imaging techniques such as MRI and CT scans can be used to confirm that the number of cancer cells present within the mammal is reduced following administration of the viral vectors. In some cases, the following examination criteria can be used. A non-nodal lesion is considered measurable if its longest diameter can be accurately measured as 2.0 cm with chest x-ray, or as =1.0 cm with CT scan or MRI. A superficial non-nodal lesion is measurable if its longest diameter is =1.0 cm in diameter as assessed using calipers (e.g., skin nodules) or imaging. In the case of skin lesions, documentation by color photography, including a ruler to estimate the size of the lesion, can be used. A malignant lymph node is considered measurable if its short axis is >1.5 cm when assessed by CT scan (CT scan slice thickness recommended to be no greater than 5 mm) In physical examinations for superficial non-nodal lesions, physical examination is acceptable, but imaging is preferable. In the case of skin lesions, documentation by color photography, including a ruler to estimate the size of the lesion, can be used.

In some cases, a GNAQ antigen, a TYRP1 antigen, and an N-RAS antigen, a BRAF antigen, a TOPO-IIα antigen, and a YB-1 antigen, a TGF-β antigen, a MDR1 antigen, a TYRP-1 antigen, and a KDR2 antigen, a TOPOIIα antigen, a YB-1 antigen, a CDC7 kinase antigen, and a BRAF antigen, a TOPOIIα antigen, a YB-1 antigen, a CDC7 kinase antigen, and a CD44 antigen, a TOPOIIα antigen and an ABCB5α antigen, a TGF-β antigen, a KDR2 antigen, a P Glyc antigen, and a TYRP-1 antigen, or an ABCB5α antigen, a CYT-C antigen, a N-RAS antigen, and a TYRP-1 antigen can be administered as a combination in the form of polypeptides. For example, a GNAQ antigen, a TYRP1 antigen, and an N-RAS antigen (each in the form of polypeptides) can be formulated with an adjuvant such as alum, monophosphoryl lipid A, liposomes, QS21, MF-59, or immunostimulating complexes (ISCOMS) and administered to a mammal having cancer (e.g., uveal melanoma). Following this administration, the number of cancer cells present within the mammal can be reduced. In some cases, a BRAF antigen, a TOPO-IIα antigen, and a YB-1 antigen can be administered as a combination in the form of polypeptides to a mammal having cancer (e.g., skin melanoma). Following this administration, the number of cancer cells present within the mammal can be reduced.

In some cases, therapy with a combination of antigens provided herein can include the use of radiation. For example, when treating cutaneous melanoma, a patient can be treated with both radiation and a combination of antigens provided herein.

In some cases, therapy with a combination of antigens provided herein can include the administration of one or more immune checkpoint inhibitors. For example, a combination of viral vectors (e.g., VSV vectors) designed to express a GNAQ antigen, a TYRP1 antigen, and an N-RAS antigen, a BRAF antigen, a TOPO-IIα antigen, and a YB-1 antigen, a TGF-β antigen, a MDR1 antigen, a TYRP-1 antigen, and a KDR2 antigen, a TOPOIIα antigen, a YB-1 antigen, a CDC7 kinase antigen, and a BRAF antigen, a TOPOIIα antigen, a YB-1 antigen, a CDC7 kinase antigen, and a CD44 antigen, a TOPOIIα antigen and an ABCB5α antigen, a TGF-β antigen, a KDR2 antigen, a P Glyc antigen, and a TYRP-1 antigen, or an ABCB5α antigen, a CYT-C antigen, a N-RAS antigen, and a TYRP-1 antigen can be administered in combination with one or more immune checkpoint inhibitors to treat a mammal having cancer. Examples of immune checkpoint inhibitors include, without limitation, anti-PD1 antibodies, anti-CTLA4 antibodies, anti-PDL1 antibodies, anti-PDL2 antibodies, anti-CD40 ligand antibodies, and anti-KIR antibodies.

The invention will be further described in the following examples, which do not limit the scope of the invention described in the claims.

EXAMPLES

Example 1—Treating Melanoma Using VSV Vectors Designed to Express BRAF, TOPO-IIα, and YB-1 Antigens C57BL/6 mice seeded with B16tk tumors 5 days previously were treated with GCV i.p. at 50 mg/mL for 5 consecutive days, followed by 2 days' rest, followed by 5 further consecutive injections of GCV (days 6-10 and days 13-17). Mice were injected i.v. with combinations of VSV expressing different cDNAs starting on day 20, by which time primary tumors had regressed. Subsequent i.v. injections were given on days 22, 24, 27, 29, and 31. Survival of mice (n=7/8 per group) treated sequentially with GCV, then with combinations of VSV-cDNA with i.v. injections of VSV-BRAF+VSV-YB-1+VSV-GFP; VSV-TOPOIIα+VSV-BRAF+VSV-GFP; VSV-TOPOIIα+VSV-YB-1+VSV-GFP; or VSV-BRAF+VSV-TOPOIIα+VSV-YB-1 ($3 \times 10^6$ pfu/virus/injection).

The combination of VSV expressing BRAF, TOPOIIα, and YB-1 generated significant survival benefit over any of the other combinations (FIG. 1).

Example 2—Treating Uveal Melanoma Patients Using VSV Vectors Designed to Express GNAQ, TYRP1, and N-RAS Antigens Human uveal melanoma patients are administered a combination of three VSV vectors: (a) a VSV vector designed to express a GNAQ antigen, (b) a VSV vector designed to express a TYRP1 antigen, and (c) a VSV vector designed to express a N-RAS antigen. VSV-IFN-β with N-RAS, GNAQ, or TYRP1 is administered in one single tumor location using a 21- or 22-gauge needle, whose length may range between 15 to 20 cm under CT or ultrasound guidance. Volume of injection $(Vi)=(a^2)(b)(0.5)$ [where a=the shorter diameter and b=the longer diameter] of injectable product. A maximum volume of 15 cc is used to prepare the investigational product. The three forms of VSV-hIFN-β (i.e., VSV-IFN-N-RAS, VSV-IFN-GNAQ, and VVS-IFN-TYRP1) are mixed together in a 1:1:1 dilution. The combination of three VSV vectors is administered as a mixture via a single intratumoral injection. The injection occurs slowly. If the tumor size is over 2 cm, this may require multiple injections. These injection sites are at least 2 cm apart from one another. Depending on the size and location of the tumor, it is estimated that the procedure will take anywhere from 30 to 60 minutes in duration.

The concentration (pfus) for each of the three VSV vectors in the mixture is between $10^5$ and $10^9$. The injection is given on day 1, and the length of the study is 28 days.

Follow-up tumor measurements are repeated every 8 weeks, or as deemed appropriate by the investigator, through the observation period. Tissue specimens are collected and submitted on days 1, 2, and 8 on patients that allow for another biopsy.

Example 3—Treating Skin Melanoma Patients Using VSV Vectors Designed to Express BRAF, TOPO-IIα, and YB-1 Antigens Human skin melanoma patients with stage II and III melanoma are administered adjuvantly and stage IV melanoma patients with oligometastatic melanoma (1-5 metastatic deposits) are administered a combination of three VSV vectors: (a) a VSV vector designed to express a BRAF antigen, (b) a VSV vector designed to express a TOPO-IIα antigen, and (c) a VSV vector designed to express a YB-1 antigen. Patients with stage IV melanoma receive VSV (i.e., VSV-BRAF, VSV YB-1, and VSV-TOPO-IIα) in combination with ablative radiation. VSV-BRAF, VSV-YB-1, and VSV-TOPO-IIα are administered intratumorly or intravenously or subcutaneously using a 21- or 22-gauge needle, whose length may range between 15 to 20 cm under CT or ultrasound guidance. Volume of injection $(Vi)=(a^2)(b)(0.5)$ [where a=the shorter diameter and b=the longer diameter] of injectable product. The three forms of VSV (i.e., VSV-BRAF, VSV-YB-1, and VSV-TOPO-IIα) are mixed together in a 1:1:1 dilution. The combination of three VSV vectors is administered as a mixture via a single injection.

Example 4—Combination Viroimmunotherapy with Checkpoint Inhibition to Treat Glioma Cell Lines Murine B16 cells (American Type Culture Collection, Manassas, Va.) were grown in Dulbecco's modified Eagle's medium (DMEM; Life Technologies, Carlsbad, Calif.) supplemented with 10% fetal calf serum (FCS; Life technologies) and L-glutamine (Life technologies). Murine GL261 cells (American Type Culture Collection, Manassas, Va.) were grown in DMEM supplemented with 10% FCS. TRAMP-C2 (TC2) cells, derived from a prostate tumor that arose in a TRAMP mouse, were characterized as described elsewhere (Kottke et al., *Cancer Res.*, 67:11970-9 (2007)) and were routinely grown as tumors in C57BL/6 mice in an androgen-independent manner. The K1735 melanoma cell line (Chong et al., *Hum. Gene Ther.*, 7:1771-9 (1996)) was derived from H-2k C3H/He mice.

Mice

C57BL/6 and C3H mice were purchased from The Jackson Laboratory (Bar Harbor, Me.) at 6-8 weeks of age.

Virus

The ASMEL VSV-cDNA library was generated as described elsewhere (Kottke et al., *Nature Med.*, 2011:854-9 (2011); Pulido et al., *Nat. Biotechnol.*, 30:337-43 (2012); and Alonso-Camino et al., *Mol. Ther.*, 22:1936-48 (2014)). Individual viral clones (VSV expressing N-RAS, CYT-C, TYRP-1, HIF-2α, SOX-10, or c-MYC) were isolated by limiting dilution as described elsewhere (Pulido et al., *Nat. Biotechnol.*, 30:337-43 (2012); and Alonso-Camino et al., *Mol. Ther.*, 22:1936-48 (2014)). These were expanded in BHK cells and purified by sucrose gradient centrifugation. VSV-GFP was manufactured by cloning the cDNA for GFP into the plasmid pVSV-XN2 as described elsewhere (Fernandez et al., *J. Virol.*, 76:895-904 (2002)). Monoclonal VSV-GFP was obtained by plaque purification on BHK-21 cells and concentrated by sucrose-gradient centrifugation.

Measurement of HIF-2α Polypeptide in i.c. Explants and In Vitro Cultures

To establish i.c. tumors, $1 \times 10^4$ cells in 2 µL, PBS were stereotactically injected into the brain (1 mm anterior, and 2 mm lateral to the bregma) of C57Bl/6 (B16, GL261, or TC2 cells) or C3H (K1735 cells) mice. Mice were sacrificed upon sign of distress, and single-cell suspensions of brain tumor explants or in vitro cultured cells (B16, GL261, TC2 or K1735) were plated at $1 \times 10^5$ per well in DMEM+10% FCS and 1% penicillin-streptomycin. Cell-free supernatants were harvested, and HIF-2α polypeptide expression was measured by ELISA according to the manufacturer's instructions (USCN Life Sciences, Houston Tex.). 1×10⁵ cells of each cell line (B16, GL261, TC2, K1735) from in vitro cultures also were plated and measured for HIF-2α polypeptide expression.

Measurement of HIF-2α Polypeptide in Co-Cultures of GL261 and Splenic/Brain-Derived CD11b+ Cells CD11b+ cells were purified from brain-cell suspensions of multiple brains, or from the spleens of C57B1/6 mice (re-suspended in Iscove's modified Dulbecco's medium (IMDM; Gibco, Grand Island, N.Y.)+5% FCS+1% penicillin-streptomycin+40 µmol/12-ME) using CD11b microbeads according to the manufacturer's instructions (Miltenyi Biotech, Auburn, Calif.). 1×10⁶ CD11b+ cells were co-cultured in DMEM+10% FCS and 1% penicillin-streptomycin with (1×10⁵) GL261 cells. After 24 hours of co-culture, cell-free supernatants were harvested, and HIF-2α polypeptide levels were measured by ELISA. HIF-2α polypeptide also was evaluated following co-culture of GL261 cells with brain- or spleen-derived CD11b+ cells, in the presence of 10 ng/mL recombinant TGF-β RH Fc Chimera 341-BR (R&D systems, MN).

Human Tumor Explants

Human primary glioblastoma brain tumor tissue was obtained following surgery. Within three hours of surgical resection, explants were depleted of CD11b+ cells using CD11b microbeads. Tumor cells were then seeded at 1×10⁴ cells per well in DMEM+10% FCS+1% penicillin-streptomycin±isolated autologous CD11b+ cells (5×10³ per well). HIF-2α polypeptide levels in cell-free supernatants were evaluated at 24 hours and again following 2 week's culture. HIF-2α polypeptide also was evaluated in cell-free supernatants from 1×10³ isolated CD11b+ cells, 24 hours after explant.

In Vivo Studies

To establish i.c. tumors, 1×10⁴ GL261 cells in 2 µL PBS were stereotactically injected using a syringe bearing a 26G needle into the brain (1 mm anterior, and 2 mm lateral to the bregma) of C57BL/6 mice (7-9 mice per treatment group unless otherwise stated). Virus, drug, or PBS control (100 µL) was administered intravenously following 5 days tumor establishment and occurred as dictated by each specific study. Mice were examined daily for overall health and, survival with time was documented.

For the therapeutic study evaluating the effect of anti-PD1 antibody in combination with virus treatment, control ChromPure rat IgG antibody (Jackson Immunochemicals, West Grove, Pa.) or anti-PD1 antibody were injected intravenously at 225 µg/mouse/injection (Clone RMP 1-14, Bioxcell West Lebanon, N.H.). For therapy evaluating the use of two checkpoint inhibitors, intravenous anti-PD1 was administered at 225 µg/mouse/injection and anti-CTLA4 at 0.1 mg/mouse/injection (Bioxcell West Lebanon, N.H.).

In Vitro Splenic/Lymph Node T-Cell Reactivation and ELISA for IFN-γ/IL-17

Spleens and lymph nodes were harvested from euthanized mice and dissociated into single-cell suspensions by crushing through a 100 µm filter. Red blood cells were lysed with ACK lysis buffer (sterile distilled H₂O containing 0.15 M NH₄Cl, 1.0 mM KHCO₃ and 0.1 mM EDTA adjusted to pH 7.2-7.4) for 2 minutes. Cells were re-suspended at 1×10⁶ cells/mL in IMDM+5% FCS+1% penicillin-streptomycin+ 40 µmol/12-ME. Pooled cells (1×10⁶ per well) were stimulated with freeze thaw lysates (equivalent to 1×10⁵ cells) of either GL261 tumors recovered from mice bearing i.c. GL261 tumors or in vitro cultured GL261 cells, every 24 hours for 3 days. Following 48 hours of culture, cell-free supernatants were collected and assayed by ELISA for IFN-γ (BD Biosciences, San Jose, Calif.) or IL-17 (R&D systems, Minneapolis, Minn.). Re-stimulation also was carried out with splenocytes and lymph node cells depleted of Treg cells using Miltenyi CD4+/CD25+ beads (Miltenyi Biotech, Auburn, Calif.). Splenocyte and lymph node single cell isolates also were stimulated as described herein with the VSV-N protein derived epitope peptide (VSV-N52-59: RGYVYQG at 5 µg/mL) (synthesized at a core facility) and supernatants were evaluated for IFN-γ and IL-17 response by ELISA.

Statistics

Survival data from animal experiments were analyzed using the log rank test with Graph Pad Prism 6 (Graph Pad software, La Jolla, Calif.). A two-sample, unequal variance Students t-test was used to evaluate in vitro data. Statistical significance was determined at the level of $P<0.05$.

Results

Figure 2:
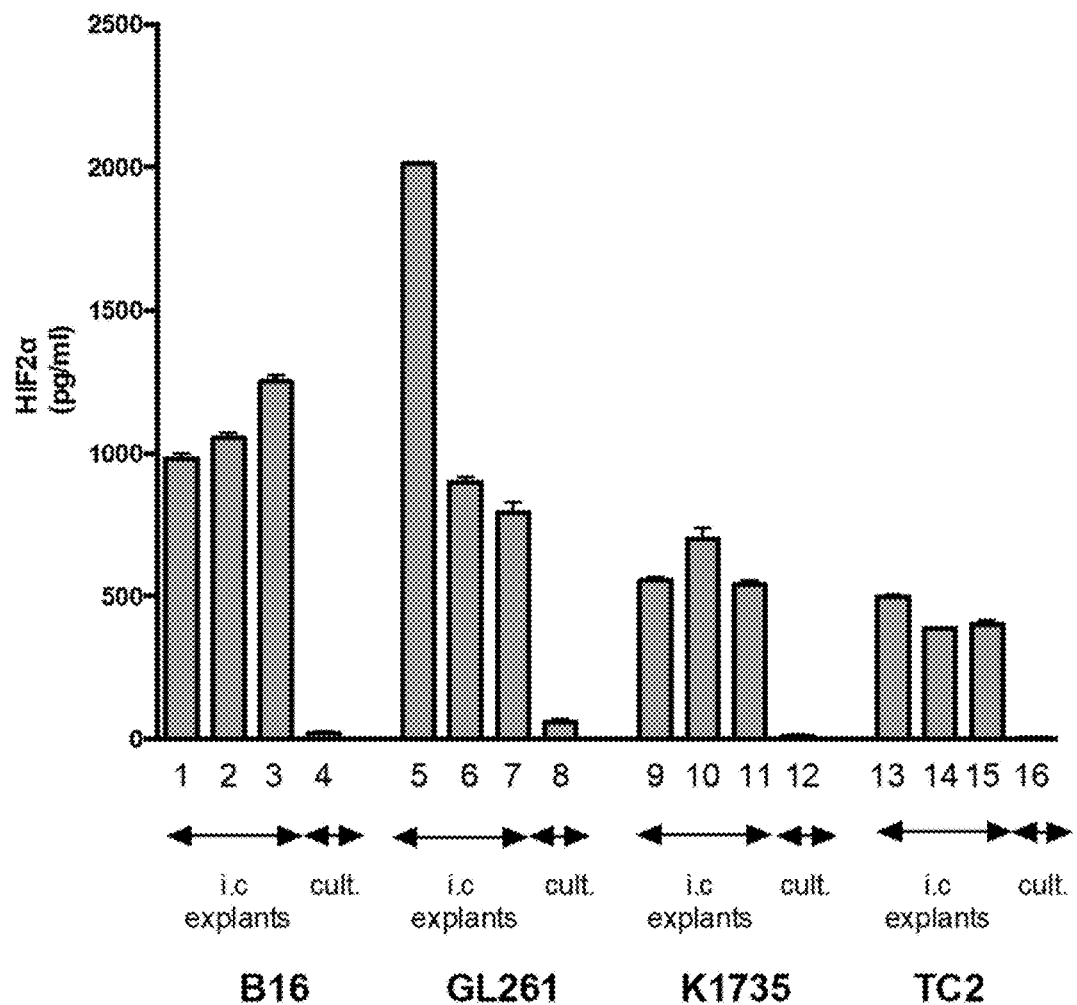
FIG. 2. Intracranial tumors of different histology express a HIF-2αHi phenotype. Tumors established in the brains of C57BL/6 (B16, GL261 or TC2 cells) or C3H (K1735) mice were dissected upon sacrifice (tumor explants), and tumor cells were seeded at $1 \times 10^5$ per well. $1 \times 10^5$ cells of each cell line cultured in vitro (cult.) were also plated. HIF-2α was measured by ELISA after 24 hours. Error bars are expressed as standard deviation (SD).

Intra-cranial tumors of different histologies express a similar HIF-2αHi phenotype. It was hypothesized that the intra-cranial microenvironment imposes a HIF-2αHi phenotype upon different types of tumors, which is distinct from that expressed by the same tumor cells growing in culture. Consistent with this hypothesis, freshly resected i.c. tumors of different histological types, including K1735 melanoma (in C3H mice), as well as B16 melanoma, GL261 glioma, and TC2 prostate cancer (C57B1/6 mice), all expressed a HIF-2αHi phenotype. In contrast, the same cell lines grown in culture, from which the tumors were initially derived by i.c. implantation, expressed low or undetectable levels of HIF-2α (FIG. 2).

Figure 3:
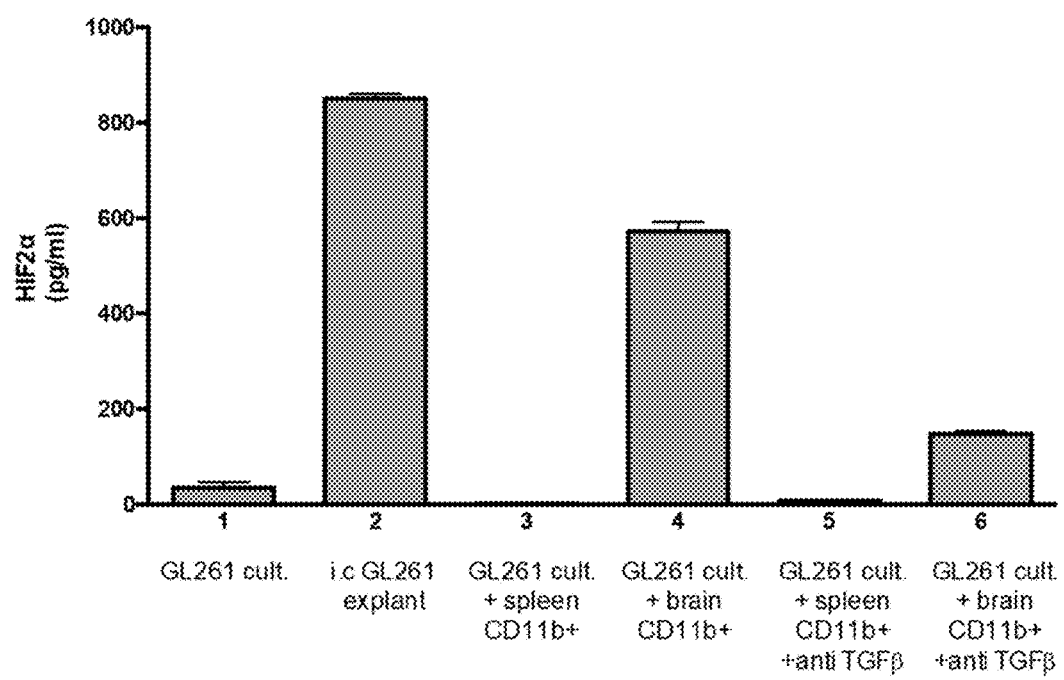
FIG. 3. Brain derived CD11b+ cells impose a HIF-2αHi phenotype on in vitro cultured GL261, in part through TGF-β. HIF-2α expression was measured by ELISA from: $1\times10^5$ GL261 cells cultured in vitro for 24 hours (lane 1); GL261 i.c. tumors, dissected from the brain upon sacrifice, and plated at $1\times10^5$ cells per well for 24 hours (lane 2); $1\times10^5$ GL261 cells co-cultured for 24 hours with $1\times10^6$ CD11b+ cells purified from normal splenocytes of C57B1/6 mice (lane 3); $1\times10^5$ GL261 cells co-cultured for 24 hours with $1\times10^6$ CD11b+ cells purified from normal brains of C57B1/6 mice (lane 4). Cultures of lanes 3 and 4 were repeated in the presence of recombinant TGF-β RII Fc chimera at 10 ng/mL (lane 5 and 6). Results are representative of three separate measurements. Error bars are expressed as standard deviation (SD).

CD11b+ cells in intact brain homogenate impose a HIF-2αHi phenotype on GL261 cells in vitro in part through TGF-β. The HIF-2αHi phenotype of i.c. B16-ova tumors was imposed by brain-associated, but not spleen-derived, CD11b+ cells. In vitro co-culture of GL261 cells with CD11b+ cells purified from intact brain homogenate, mediated a similar HIF-2αLo to HIF-2αHi phenotypic transition (FIG. 3). As for the B16 model, splenic CD11b+ cells were unable to impose a HIF-2αHi phenotype on in vitro cultured glioma cells (FIG. 3). Whilst neutralization of neither TNF-α, VEGF, nor interferon-γ prevented induction of the HIF-2αHi phenotype in GL261 and brain-associated CD11b+ cell co-cultures, blocking TGF-β significantly reduced HIF-2α expression (p=0.000173) (FIG. 3). These results demonstrate that CD11b+ cells of the brain micro-environment impose the HIF-2αHi phenotype upon tumors growing i.c., mediated, at least in part, through TGF-β.

Figure 4:
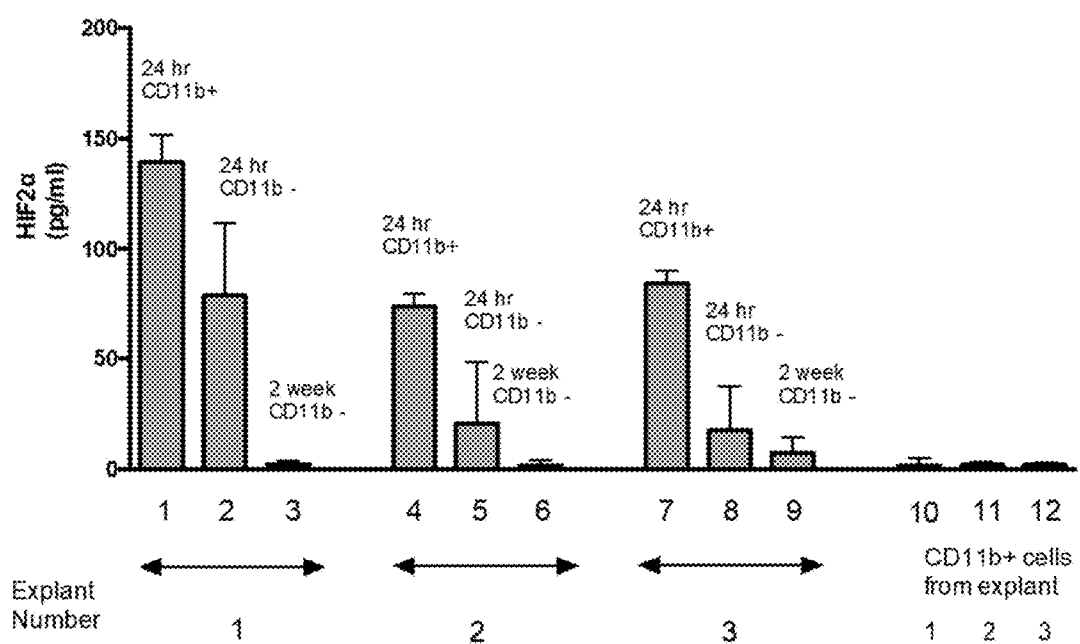
FIG. 4. Human brain tumor explants express a HIF-2αHi phenotype which diminishes with time. Human brain tumor explants were recovered from surgery and depleted of CD11b+ cells. Tumor cells were plated at $1\times10^4$ per well either alone (24 hours CD11b) or with $5\times10^3$ CD11b+ cells (24 hours CD11b+). HIF-2α expression was measured at 24 hours. In cultures from which tumor cells survived more than a week, HIF-2α was measured from $1\times10^4$ tumor cells after 2 weeks, by which time CD11b+ cells had been washed away/died (2 week CD11b−). HIF-2α also was measured from $1\times10^3$ separated CD11b+ cells 24 hours after explant. Results are representative of three separate measurements. Error bars are expressed as standard deviation (SD).

Human tumor explants express a HIF-2αHi phenotype, which is reduced over time. To investigate how the murine model might reflect the patient situation, the HIF-2α phenotype of primary human brain tumor samples was studied. Freshly resected tumors cultured with their own autologous CD11b+ cells exhibited a HIF-2αHi phenotype, although levels of HIF-2α were consistently lower than in resected murine tumors (FIG. 4). Brain tumor explants depleted of CD11b+ cells expressed lower levels of HIF-2α after 24 hours of culture, although this did not reach statistical significance (p=0.101) (FIG. 4). The CD11b+ cells themselves did not express significant levels of HIF-2α (FIG. 4). After 2 weeks, CD11b+ cells within these co-cultures were lost, and the level of tumor cell associated HIF-2α was significantly reduced compared to levels seen at 24 hours post explant (p=0.017) (FIG. 4). Therefore, human brain tumors also express a HIF-2αHi phenotype, which is maintained, at least in part, by immune cells within the brain microenvironment.

Intracranial GL261 can be Treated with VSV-Tumor-Associated Antigen Therapy and Enhanced by Addition of Checkpoint Inhibitors Although mice bearing s.c. B16 tumors were treated successfully with a combination of VSV-expressed N-RAS, CYT-C, and TYRP-1, i.c. B16 tumors were only successfully treated with a combination of VSV expressed HIF-2α, SOX-10, c-MYC, and TYRP-1. The hypothesis that effective immunotherapy of an i.c. tumor of a different histological type could be targeted against this common i.c. tumor phenotype imposed by the brain microenvironment was tested further. Consistent with this, systemic delivery of VSV expressed HIF-2α, SOX-10, and c-MYC generated significant therapy over control treatment (p=0.0001) (FIG. 4). Although a combination of just two of the VSV-antigen gave significant therapy compared to control treatment (p=0.0001), optimal therapy required the combination of all three (HIF-2α, SOX-10, c-MYC) antigens ((VSV-HIF-2α/SOX-10/c-MYC) versus (VSV-HIF-2α/SOX-10+VSV-GFP) p=0.0414). Unlike in the B16 i.c. model, addition of the VSV-TYRP-1 virus gave no added therapeutic benefit to treatment with VSV-expressed HIF-2α, SOX-10, and c-MYC (data not shown). Consistent with our previous data with B16 i.c., as opposed to s.c. tumors, the combination of VSV expressed N-RAS, CYT-C and TYRP-1 was ineffective against i.c. GL261 tumors and offered no significant therapeutic advantage over control therapy (p=0.1432) (FIG. 4).

Figure 5:
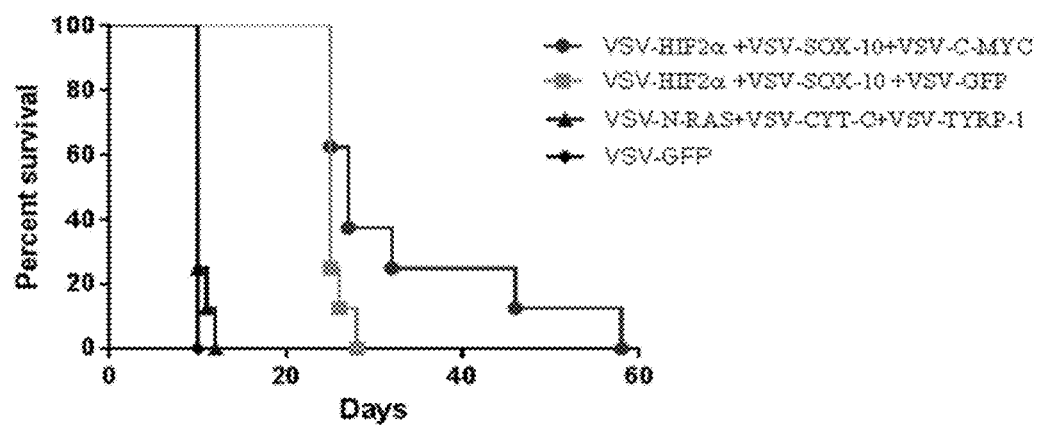
Figure 6A:
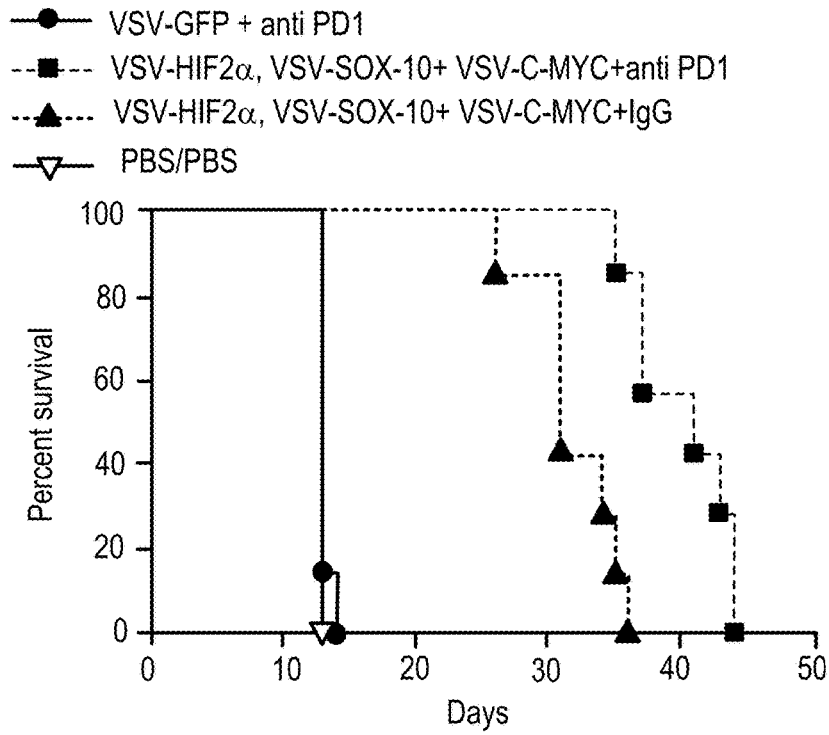
FIG. 6. Checkpoint inhibition uncovers a repressed anti-tumor Th1 IFN-γ response. A. C57BL/6 mice bearing 5 day established i.c. GL261 tumors were treated intravenously with a total of $5\times10^6$ pfu of (VSV-GFP); (VSV-HIF-2α, VSV-SOX-10, and VSV-c-MYC), or PBS on days 6, 8, 10, 13, 15, 17, 20, 22, and 24. On days 13, 15, 17, 20, 22, and 24, these groups were treated intravenously with either PBS, control IgG antibody, or anti-PD1 antibody at 10 mg/kg/mouse as shown. Survival with time is shown. B-D. Splenocytes and lymph nodes were pooled from 3 C57BL/6 mice per group bearing 5 day established i.c. GL261 tumors treated with either (PBS/PBS); (VSV-GFP+anti-PD1 antibody); (VSV-HIF-2α, VSV-SOX-10, and VSV-c-MYC+IgG), or (VSV-HIF-2α, VSV-SOX-10, and VSV-c-MYC+anti-PD1 antibody). Cells were plated at $1\times10^6$ cells per well and re-stimulated in vitro 3 times at 24 hour intervals with $1\times10^5$ cells of freeze thaw lysates of GL261 tumors recovered from mice bearing i.c. GL261 tumors (B and D) or with freeze thaw lysates of in vitro cultured GL261 (C and E). 48 hours later, supernatants were assayed for IFN-γ (B and C) or IL-17 (D and E) by ELISA. F. Splenocytes and lymph nodes also were re-stimulated with the VSV-N protein derived epitope at 5 μg/mL, 3 times for 24 hours. 48 hours later, supernatants were assayed for IFN-γ. Each result is representative of 3 separate measurements. Error bars are expressed as standard deviation (SD).

To investigate whether the viroimmunotherapy associated with VSV-antigen therapy of i.c. GL261 could be enhanced through combination with immune checkpoint inhibition, mice bearing i.c. GL261 tumors were treated with 9 (instead of the 12 of FIG. 5) systemic injections of VSV expressed HIF-2α, SOX-10, and c-MYC plus the checkpoint inhibitor antibody anti-PD1. Addition of anti-PD1 antibody significantly extended survival compared to the virus combination alone (p=0.0006) (FIG. 6A).

Taken together, these results demonstrate that the brain micro-environment-imposed antigenic signature of HIF-2α, SOX-10, and c-MYC can be immunologically targeted to treat i.c tumors of different histologies (glioma and melanoma) and that effective immunotherapy of tumors should take into account immunological profiles imposed upon tumors by their anatomical location.

Figure 6F:
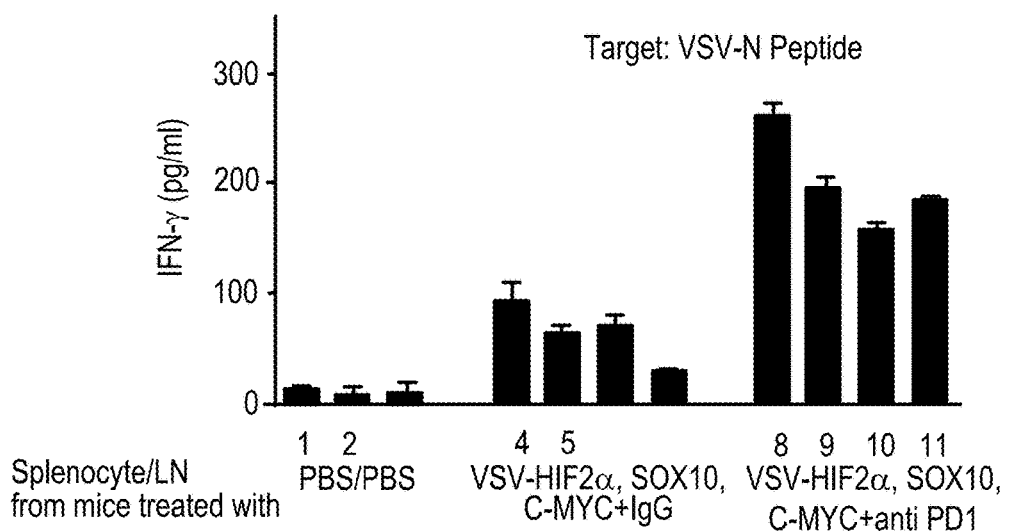
Figure 6B:
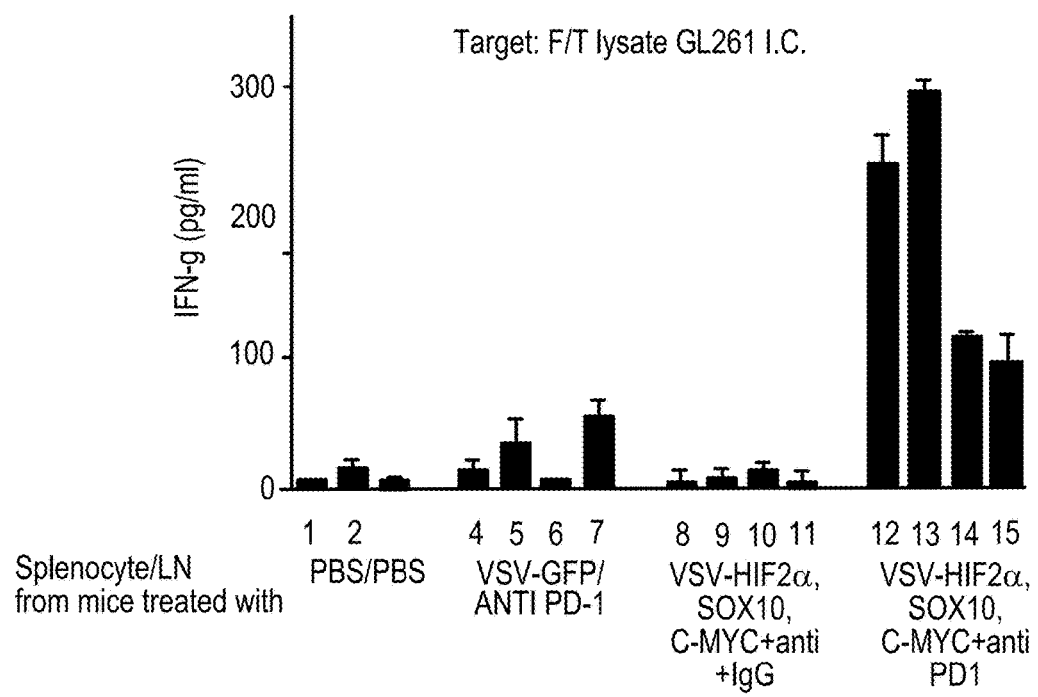
Figure 6C:
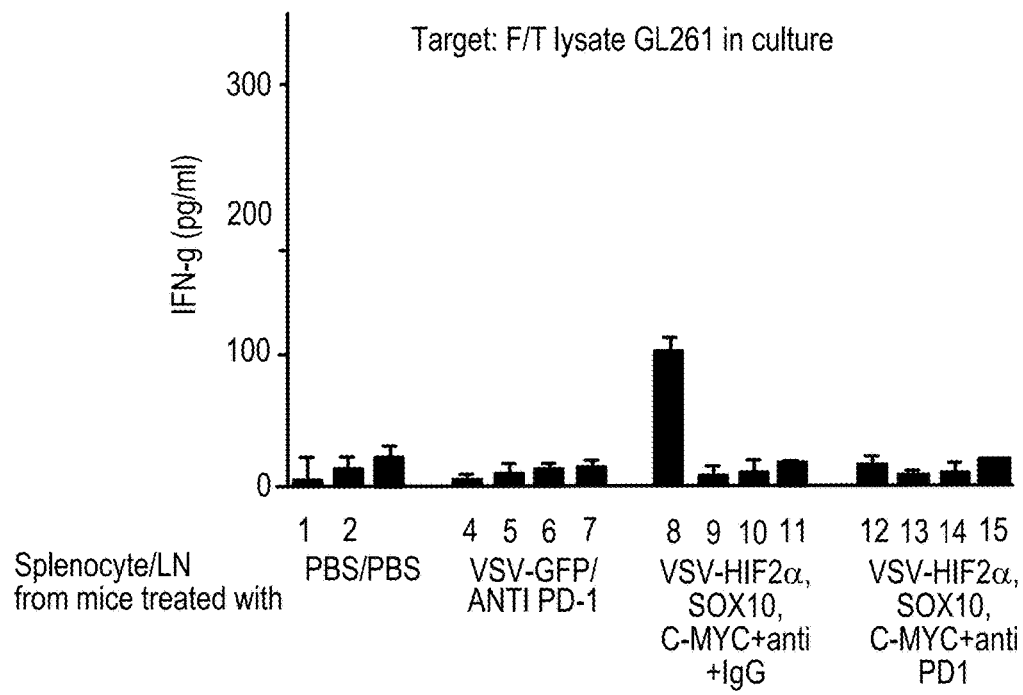

Anti-PD-1 antibody uncovers a Th1 response against intra-cranial GL261. The therapeutic anti-tumor response to self antigens induced by VSV-cDNA library treatment is Th17 CD4$^+$ T cell mediated and no Th1 IFN-γ T cell responses could be detected. Mixed splenocytes and lymph node cultures from mice bearing i.c. GL261 tumors following treatment with VSV-HIF-2α, VSV-SOX-10, and VSV-c-MYC did not secrete IFN-γ in response to challenge with freeze/thaw lysates of explanted i.c. GL261 tumors (FIG. 6B). In contrast, similar mixed cultures from mice treated with the same VSV-HIF-2α, VSV-SOX-10, and VSV-c-MYC plus anti-PD1 antibody, secreted significant levels of IFN-γ (p<0.05), suggesting that checkpoint inhibition through the PD1 axis uncovered a Th1 response to poorly immunogenic self antigens (FIG. 6B). Consistent with the distinct antigenic nature of GL261 cells growing in situ in the brain, compared to the same cells growing in culture (FIGS. 2 and 3), splenocyte and lymph node cultures from mice treated with VSV-HIF-2α/SOX-10/c-MYC+anti-PD1 did not secrete IFN-γ in response to challenge with freeze/thaw lysates derived from GL261 cells cultured in vitro (FIG. 6C). These results demonstrate that a Th1 response to a unique antigenic profile associated with i.c. GL261 tumors is generated following VSV-antigen viroimmunotherapy, but that it is suppressed in vivo and can be de-repressed upon checkpoint inhibition.

Figure 6D:
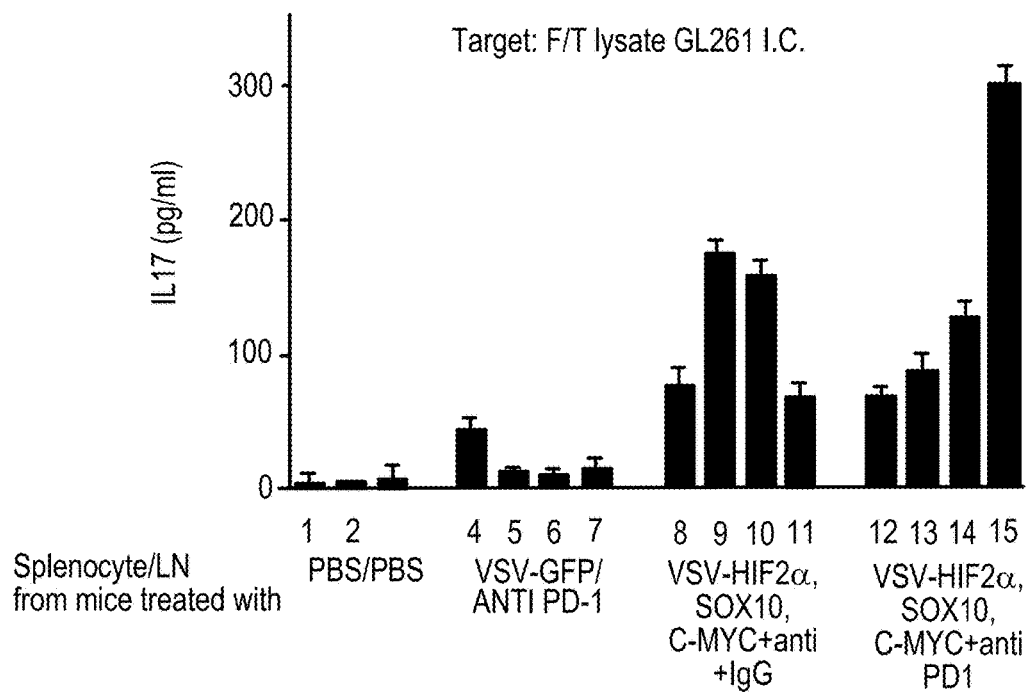
Figure 6E:
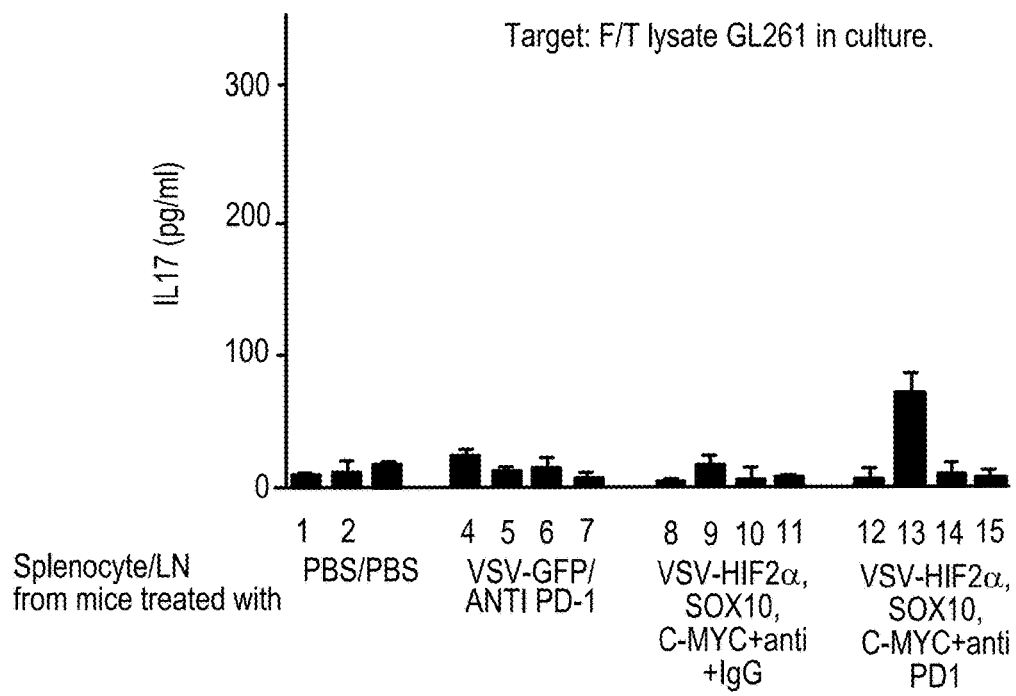

Anti-PD1 antibody therapy does not enhance the Th17 response against intra-cranial GL261. Interestingly, despite enhancing therapeutic efficacy in vivo (FIG. 6A), checkpoint inhibition with anti-PD1 did not significantly enhance the Th17 response generated by VSV-HIF-2α/SOX-10/c-MYC treatment (p=0.674) (against either i.c. explanted, or cultured, GL261 freeze thaw lysates), however, addition of anti-PD-1 enhanced a robust Th1, IFN-γ response (FIGS. 6D and 6E). A robust immune response of both Th1 IFN-γ, and Th17, anti-i.c. GL261 responses were only induced when VSV expressed tumor antigens VSV-HIF-2α/SOX-10/c-MYC, as opposed to VSV-GFP, (FIGS. 6B and 6D, respectively), indicating that virally-mediated expression of tumor antigens was required for an effective immune response.

Anti-PD1 antibody enhances the Th1 response against VSV. VSV-HIF-2α/SOX-10/c-MYC treatment reproducibly induced a Th1 response against VSV antigens (FIG. 6F). This anti-VSV Th1 response also was significantly enhanced in mice treated with checkpoint inhibition compared with VSV-antigen treatment alone (p=0.00375) (FIG. 6F).

Taken together, these results demonstrate that combination of VSV-HIF-2α/SOX-10/c-MYC viroimmunotherapy with anti-PD1 checkpoint inhibition de-represses an anti-tumor Th1 IFN-γ T cell response against both self antigens and against foreign viral antigens, but has no significant effect on the anti-tumor Th17 response.

Anti-PD1 Checkpoint Inhibition Mimics Depletion of Treg

As before (FIG. 6B), the addition of anti-PD1 to VSV-HIF-2α/SOX-10/c-MYC therapy uncovered an anti-tumor Th1 response (lane 1 and 2 compared to 3 and 4, FIG. 7A). In vitro depletion of Treg from the mixed splenocyte/LN cultures prior to re-stimulation with freeze/thaw lysates also de-repressed the Th1 IFN-γ T cell response against i.c. GL261, compared to Treg-intact cultures (lanes 1 and 2 compared to 5 and 6, FIG. 7A). However, Treg depletion from splenocyte/LN cultures of mice treated with VSV-HIF-2α/SOX-10/c-MYC+anti-PD1 did not further enhance the Th1 IFN-γ T cell response already uncovered by anti-PD1 therapy (lanes 3 and 4 compared to 7 and 8, FIG. 7A). Neither anti-PD1, nor in vitro Treg depletion, enhanced IL-17 responses generated by VSV-antigen therapy (FIG. 7B). These results demonstrate that anti-PD1 immune checkpoint inhibition may operate in vivo, to de-repress an anti-tumor Th1 IFN-γ T cell response and that this may be effected, at least in part, by affecting Treg function.

Combination Checkpoint Inhibition Further Improves VSV-Antigen Therapy

Figure 8A:
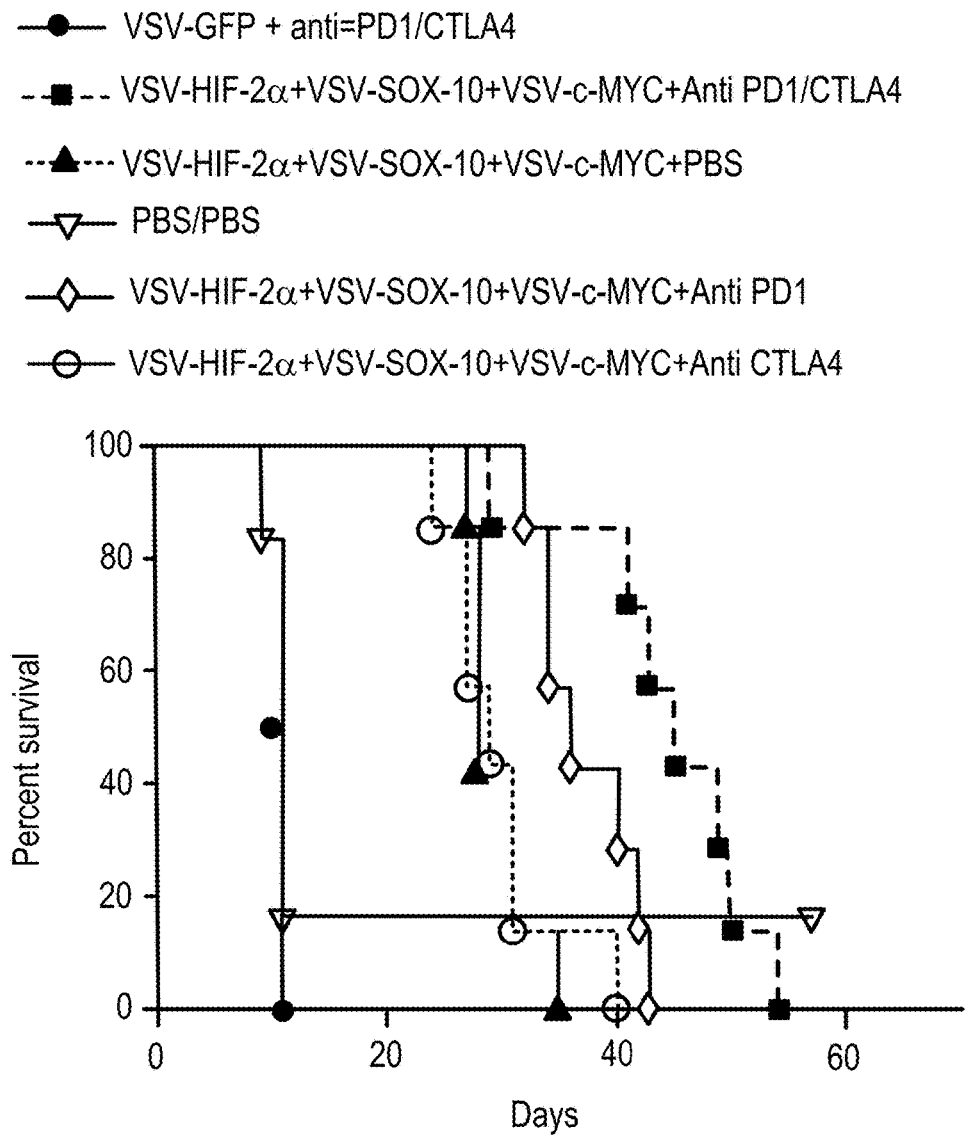
FIG. 8. Double checkpoint inhibition therapy enhances treatment with VSV-antigens. A. C57BL/6 mice bearing 5 day established i.c. GL261 tumors were treated intravenously with a total dose of $5\times10^6$ pfu of (VSV-GFP); (VSV-HIF-2α, VSV-SOX-10, and VSV-c-MYC) or PBS on days 6, 8, 10, 13, 15, and 17. On days 13, 15, and 17, these groups also were treated with either anti-PD1 antibody, anti-CTLA4 antibody, anti-PD1 antibody plus anti-CTLA4 antibody, or PBS as shown. Survival with time is shown. B-D. Splenocytes and lymph nodes were pooled from 3 C57BL/6 mice per group bearing 5 day established i.c. GL261 tumors treated with either (VSV-GFP+anti-PD1+anti-CTLA4); (VSV-HIF-2α, VSV-SOX-10, and VSV-c-MYC+anti-PD1 antibody+anti-CTLA4 antibody); (VSV-HIF-2α, VSV-SOX-10, and VSV-c-MYC+PBS); (PBS+PBS); (VSV-HIF-2α, VSV-SOX-10, and VSV-c-MYC+anti-PD1 antibody); or (VSV-HIF-2α, VSV-SOX-10, and VSV-c-MYC+anti-CTLA4 antibody). Cells were plated at $1\times10^6$ cells per well and re-stimulated in vitro 3 times at 24 hour intervals with $1\times10^5$ cells of freeze thaw lysates of GL261 tumors recovered from mice bearing i.c. GL261 tumors (B and D) or with freeze thaw lysates of in vitro cultured GL261 (C and E). 48 hours later, supernatants were assayed for IFN-γ (B and C) or IL-17 (D and E) by ELISA.

Given the success with enhancing VSV-antigen (e.g., VSV-HIF-2α/SOX-10/c-MYC) therapy with single checkpoint inhibitor therapy, a combination of anti-PD1 and anti-CTLA-4 checkpoint inhibition to target separate stages of the T cell activation/repression pathway was tested in combination with VSV-antigen (e.g., VSV-HIF-2α/SOX-10/c-MYC) therapy. As before, anti-PD1 treatment resulted in a significant improvement in survival in combination with VSV-HIF-2α/SOX-10/c-MYC therapy (FIG. 8A), in mice treated with a sub-optimal dose of 6 injections of VSV-VSV-HIF-2α/SOX-10/c-MYC (as opposed to the 12 of FIG. 5, and 9 of FIG. 6A). In contrast, anti-CTLA4 as a mono-supportive therapy for VSV-HIF-2α/SOX-10/c-MYC gave no added therapeutic benefit to VSV-HIF-2α/SOX-10/c-MYC alone (FIG. 8A). However, when used together, anti-PD1 and anti-CTLA4 significantly improved VSV-HIF-2α/SOX-10/c-MYC therapy alone (p=0.0015) and also was more effective than VSV-HIF-2α/SOX-10/c-MYC+anti-PD1 (p=0.0184) or anti-CTLA4 (p=0.0016) alone.

Figure 8B:
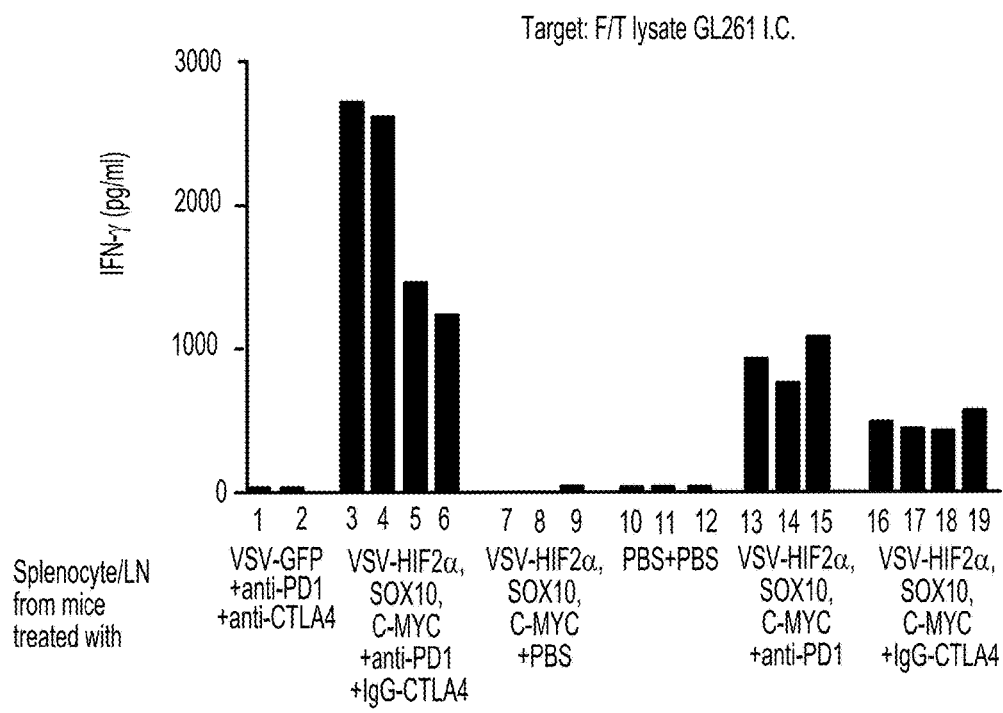
Figure 8C:
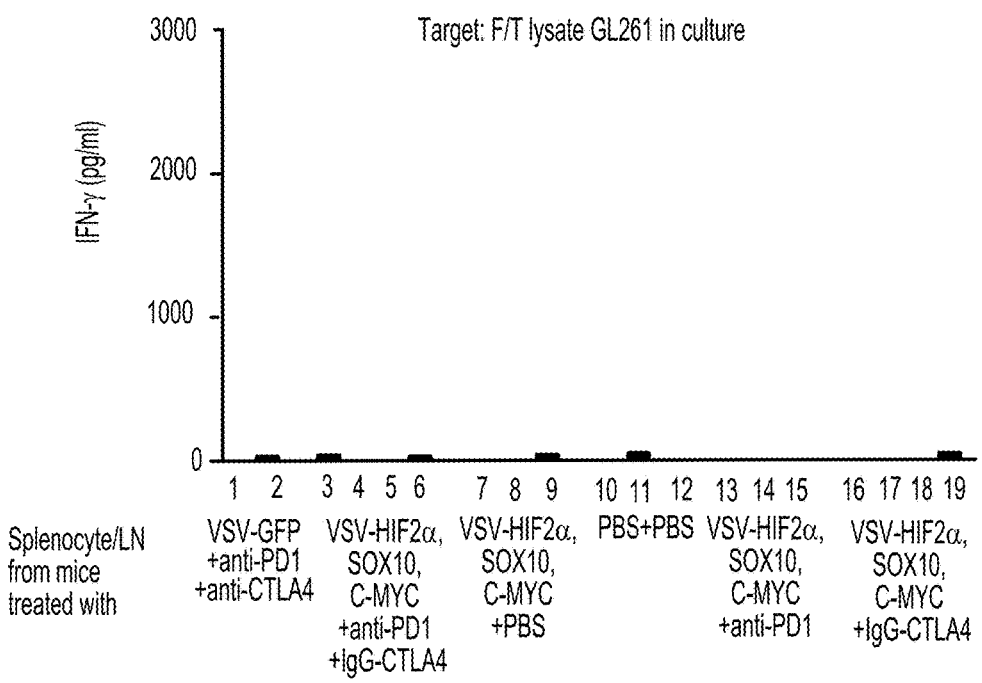

As before (FIG. 6), addition of anti-PD1 therapy to VSV-HIF-2α/SOX-10/c-MYC uncovered a Th1 IFN-γ T cell response to i.c. GL261 explants that was not detected from mice treated with VSV-HIF-2α/SOX-10/c-MYC alone (FIG. 8B). This also was true of anti-CTLA4 therapy in combination with VSV-HIF-2α/SOX-10/c-MYC, although to a lesser extent than with anti-PD1 (FIG. 8B). However, splenocyte/LN cultures from mice treated with VSV-HIF-2α/SOX-10/c-MYC and both anti-PD1 and anti-CTLA4 checkpoint inhibition displayed enhanced Th1 IFN-γ T cell response against i.c. GL261 compared to VSV-HIF-2α/SOX-10/c-MYC therapy in combination with either checkpoint inhibitor alone, although this only reached statistical significance when compared to the anti-CTLA4 treatment group (p=0.0282) (FIG. 8B).

Figure 8D:
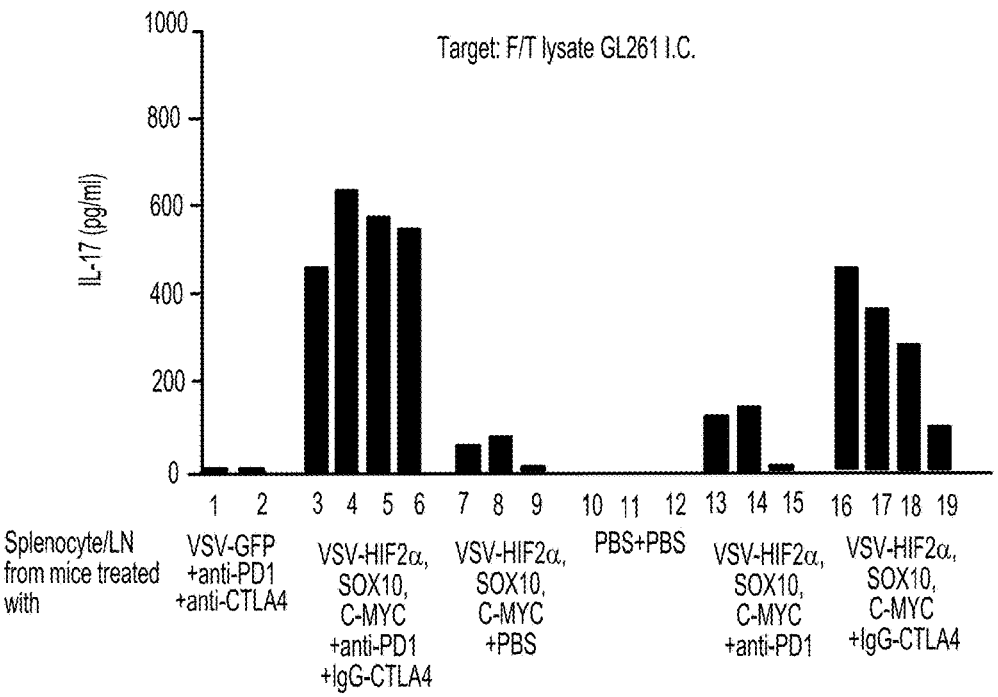
Figure 8E:
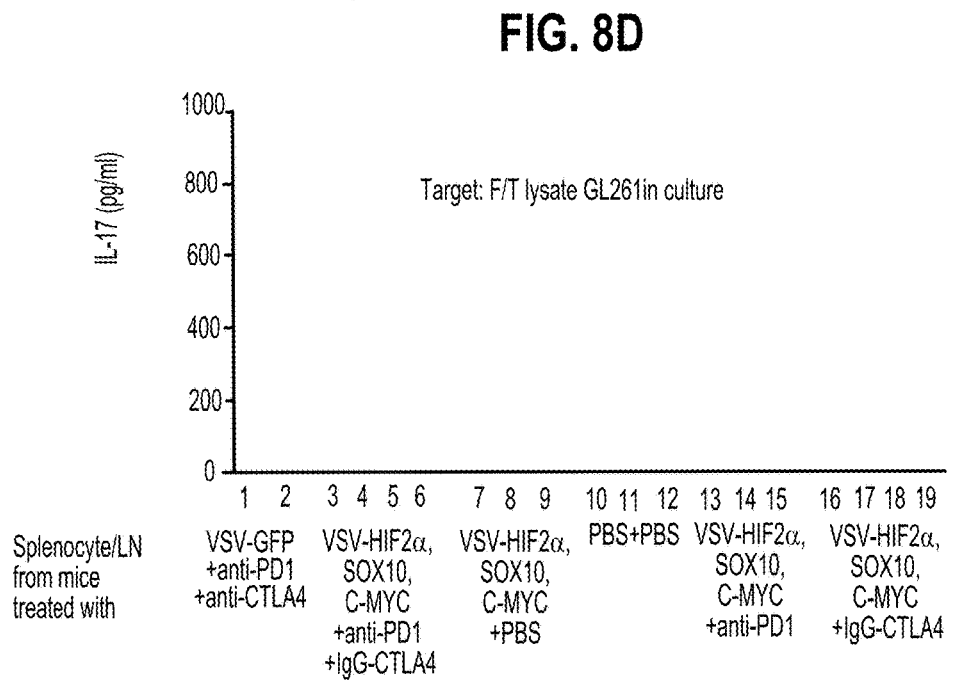

With respect to the Th-17 recall response, VSV-HIF-2α/SOX-10/c-MYC therapy in combination with anti-CTLA4 exhibited a strong trend to enhancing the Th17 response to i.c. GL261 responses (FIG. 8D) compared to VSV-HIF-2α/SOX-10/c-MYC therapy alone, or in combination with anti-PD1. Interestingly, splenocyte/LN cultures from mice treated with VSV-HIF-2α/SOX-10/c-MYC therapy combined with both anti-CTLA4 and anti-PD1 therapy generated the strongest Th17 recall responses against i.c GL261 (FIG. 8D).

Taken together, these results demonstrate that addition of checkpoint inhibitors, either singly or in combination, can enhance therapeutic responses to VSV-antigen (e.g., VSV-HIF-2α/SOX-10/c-MYC) treatment and that these increases in therapy are associated with the de-repression of an anti-tumor Th1 IFN-γ T cell response (anti-PD1, anti-CTLA4, or both) and of the anti-tumor Th17 response (anti-PD 1 plus anti-CTLA4).

Figure 9:
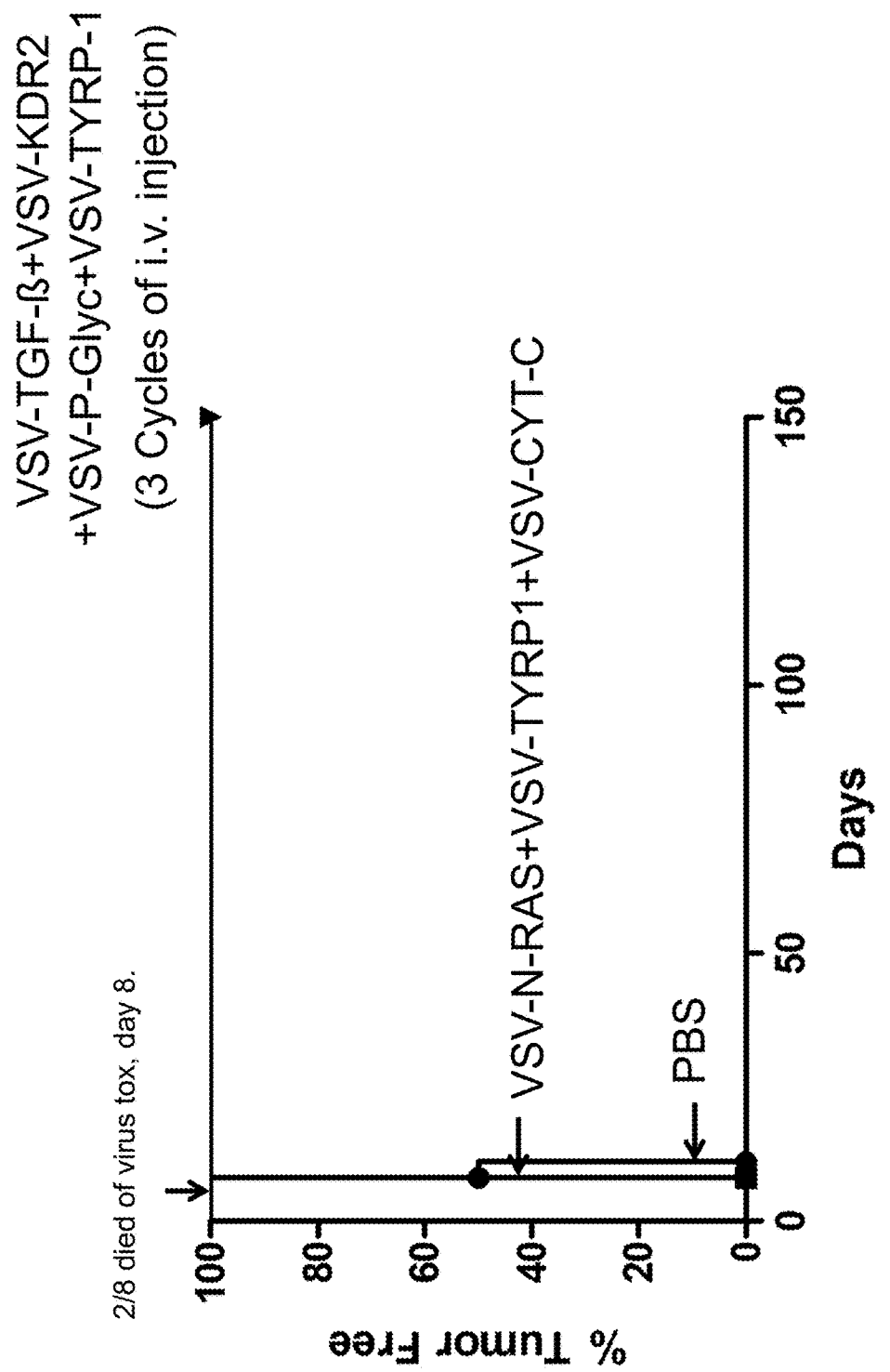
FIG. 9 is a graph plotting the percent survival of mice having s.c. B16 tumors and treated with PBS or the indicated combinations of VSV vectors.

Example 5—Treating Melanoma Using VSV Vectors Designed to Express TGF-β, KDR2, P-Glycoprotein, and TYRP-1 Antigens In a first experiment, C3H mice bearing 7 day established s.c. B16 tumors were treated i.v. with three cycles (9 doses total) of (1) VSV-TGF-β+VSV-KDR2+VSV-P Glyc+VSV TYRP-1 (5×10$^6$ pfu/100 μL), (2) VSV-NRAS+VSV-TYRP-1+VSV-CYT-C, or (3) PBS (days 7, 10, 12). Survival of tumor-bearing C3H mice (n=8 mice per group) was determined. The VSV-combination (VSV-TGF-β+VSV-KDR2+VSV-P Glyc+VSV TYRP-1) cured 6/6 mice which did not experience toxicities associated with i.v. VSV treatment (FIG. 9). Two of the 8 mice treated died of hind limb paralysis, associated with a high i.v. dose (2×10$^7$ pfu/injection; 9 injections) of the VSV combination.

In a repeat experiment, 3/5 mice were cured of K1735 tumors with a lower dose of VSV-combination (VSV-TGF-β+VSV-KDR2+VSV-P Glyc+VSV TYRP-1) (5×10$^6$ pfu/injection; 9 injections). 5/5 mice were cured with the same dose of the total library (ASMEL). In a control group (mice treated with VSV-GFP), 1 of 5 mice never developed a tumor and 1 mouse developed a tumor which never grew above 0.3 cm in diameter.

Figure 10:
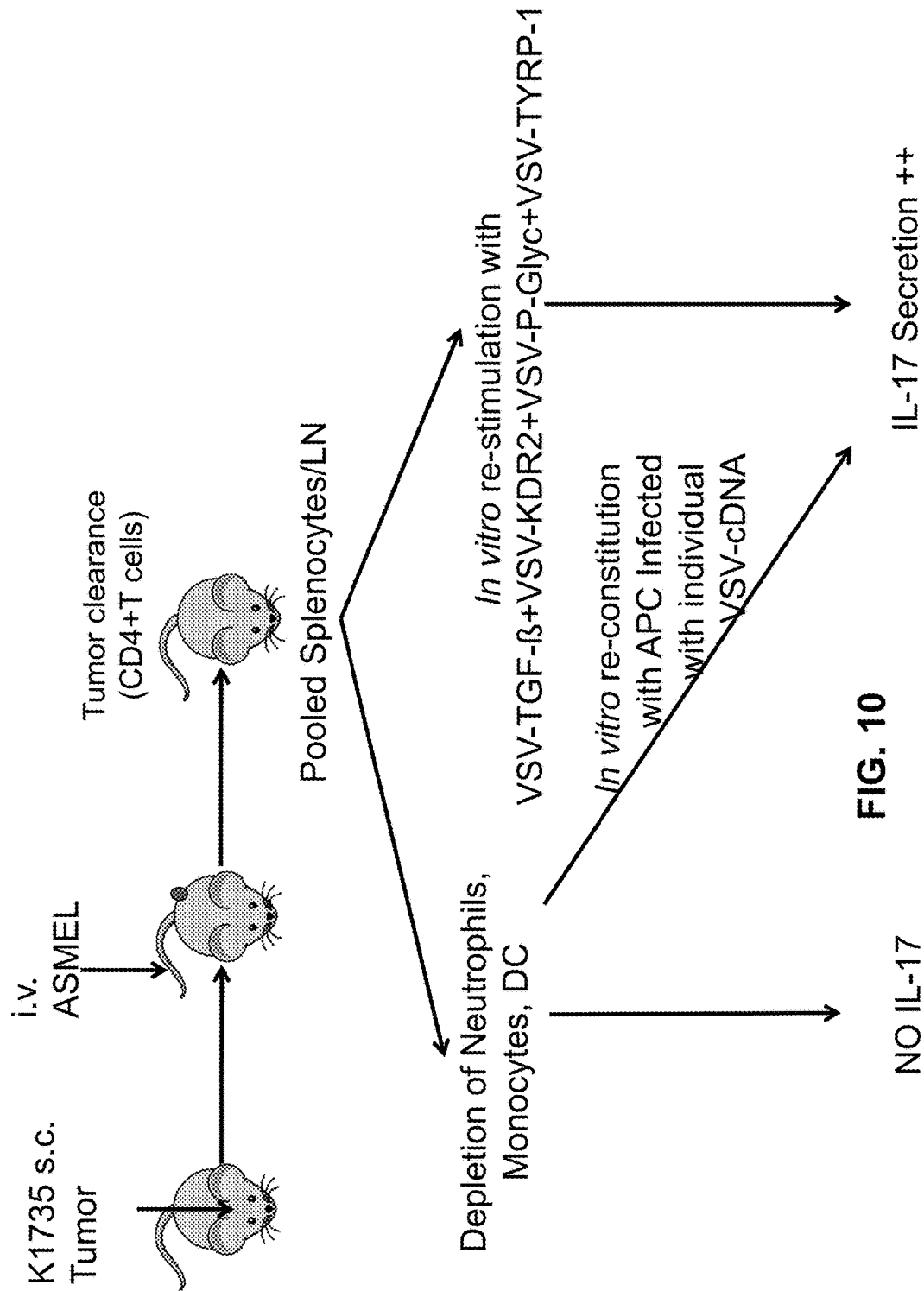
FIG. 10 is a schematic of an in vitro assay designed to determine which specific antigens are presented by which antigen presenting cell subtypes in order to reconstitute a Th17 response.
Figure 11:
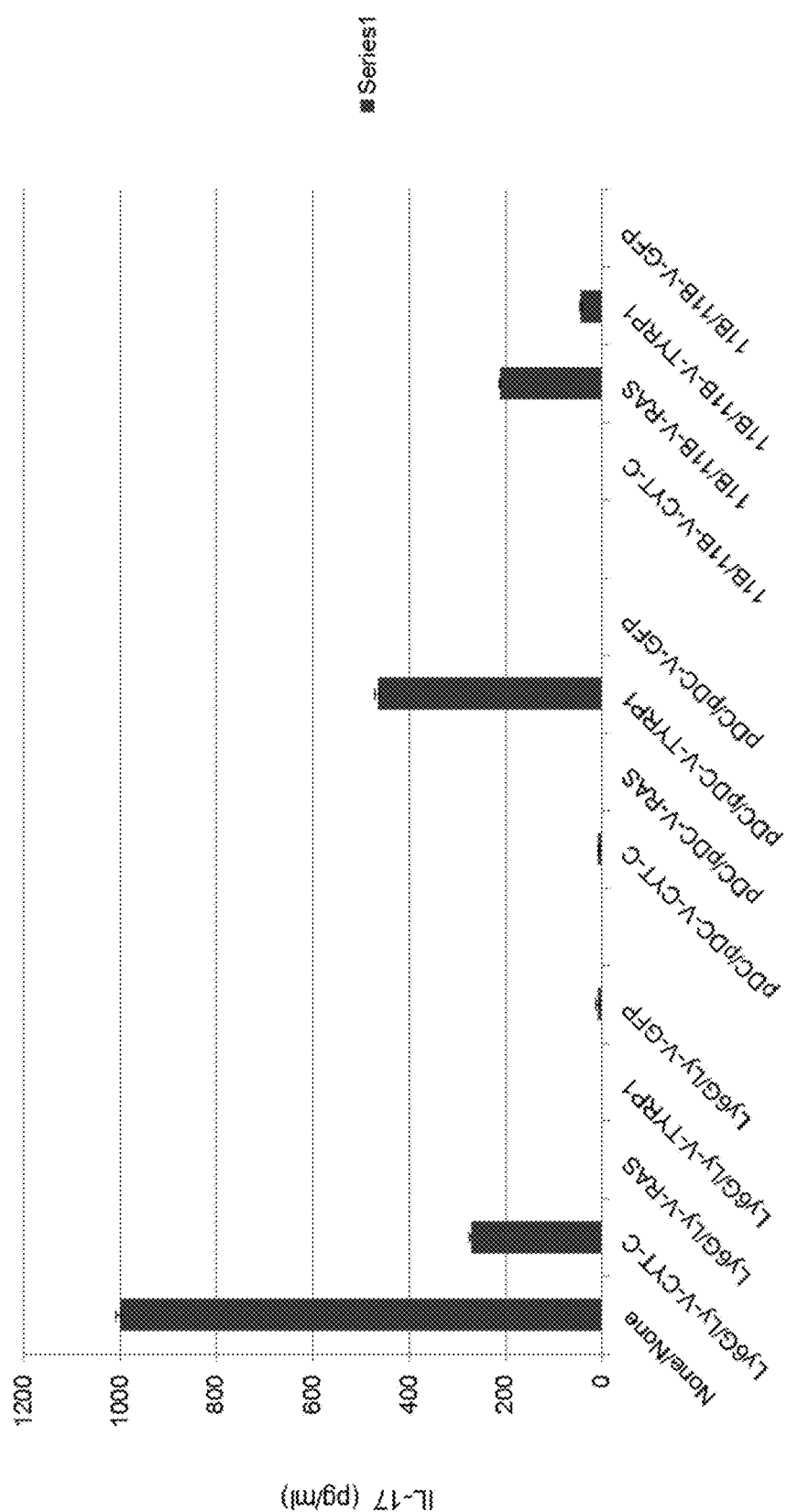
FIG. 11 is a bar graph plotting IL-17 levels (pg/mL) for the indicated conditions. None/none indicates no depletion of any cells; Ly6G/Ly-V-CYT-C indicates depletion of neutrophils and the reinfection with VSV-cytochrome C; Ly6G/Ly-V-N-RAS: indicates depletion of neutrophils and reinfection with VSV-N-RAS; Ly6G/Ly-V-TYRP-1 indicates depletion of neutrophils and reinfection with VSV-TYRP-1; Ly6G/Ly-VSVGFP indicates depletion of neutrophils and the reinfection with VSV-GFP; pDC/pDC-V-CYT-C indicates depletion of plasmacytoid dendritic cells and the reinfection with VSV-cytochrome C; pDC/pDC-V-N-RAS indicates depletion of plasmacytoid dendritic cells and the reinfection with VSV-N-RAS; pDC/pDC-V-TYRP-1 indicates depletion of plasmacytoid dendritic cells and reinfection with VSV-TYRP-1; pDC/pDC-V-GFP indicates depletion of plasmacytoid dendritic cells and reinfection with VSV-GFP; 11B/11B-V-CYTC indicates depletion of CD11b+ cells and reinfection with VSV-Cytochrome C; 11B/11B-V-N-RAS indicates depletion of CD11b+ cells and reinfection with VSV-N-RAS; 11B/11B-V-TYRP-1 indicates depletion of CD11b+ cells and reinfection with VSV- TYRP-1; and 11B/11B-V-GFP indicates depletion of CD11b+ and reinfection with VSV-GFP.
Figure 12:
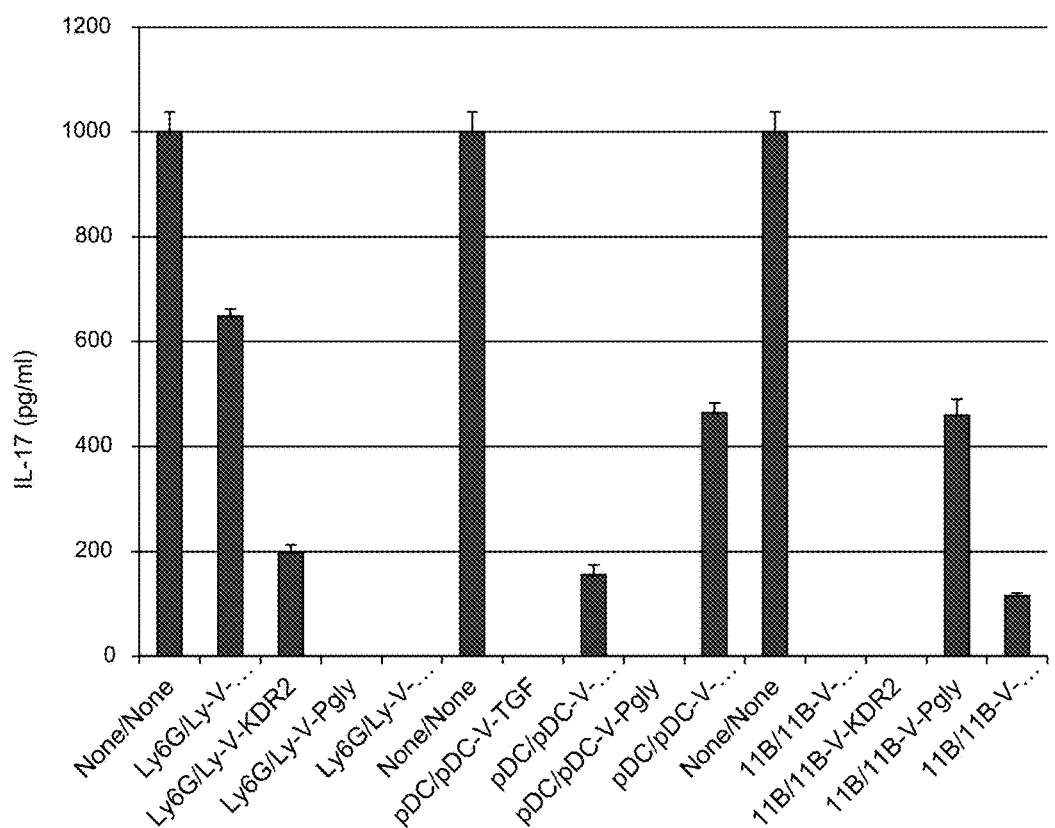
FIG. 12 is a bar graph plotting IL-17 levels (pg/mL) for the indicated conditions. None/none indicates no depletion of any cells; Ly6G/Ly-V-TGFβ indicates depletion of neutrophils and the reinfection with VSV-TGFβ; Ly6G/Ly-V-KDR2 indicates depletion of neutrophils and reinfection with VSV-KDR2; Ly6G/Ly-V-Pglyco indicates depletion of neutrophils and reinfection with VSV-P Glyc; Ly6G/Ly-VTYRP-1 indicates depletion of neutrophils and the reinfection with VSV-TYRP-1; pDC/pDC-V-TGFβ indicates depletion of plasmacytoid dendritic cells and the reinfection with VSV-TGFβ; pDC/pDC-V-KDR2 indicates depletion of plasmacytoid dendritic cells and the reinfection with VSV-KDR2; pDC/pDC-V P Glyc indicates depletion of plasmacytoid dendritic cells and reinfection with VSV-P Glyc; pDC/pDC-V-TYRP-1 indicates depletion of plasmacytoid dendritic cells and reinfection with VSV-TYRP-1; 11B/11B-V-TGFβ indicates depletion of CD11b+ cells and reinfection with VSV-TGFβ; 11B/11B-V-KDR2 indicates depletion of CD11b+ cells and reinfection with VSV-KDR2; 11B/11B-V-Pglyc indicates depletion of CD11b+ cells and reinfection with VSV-P Glyc; and 11B/11B-V-TYRP-1 indicates depletion of CD11b+ and reinfection with VSV-TYRP-1.
Figure 13:
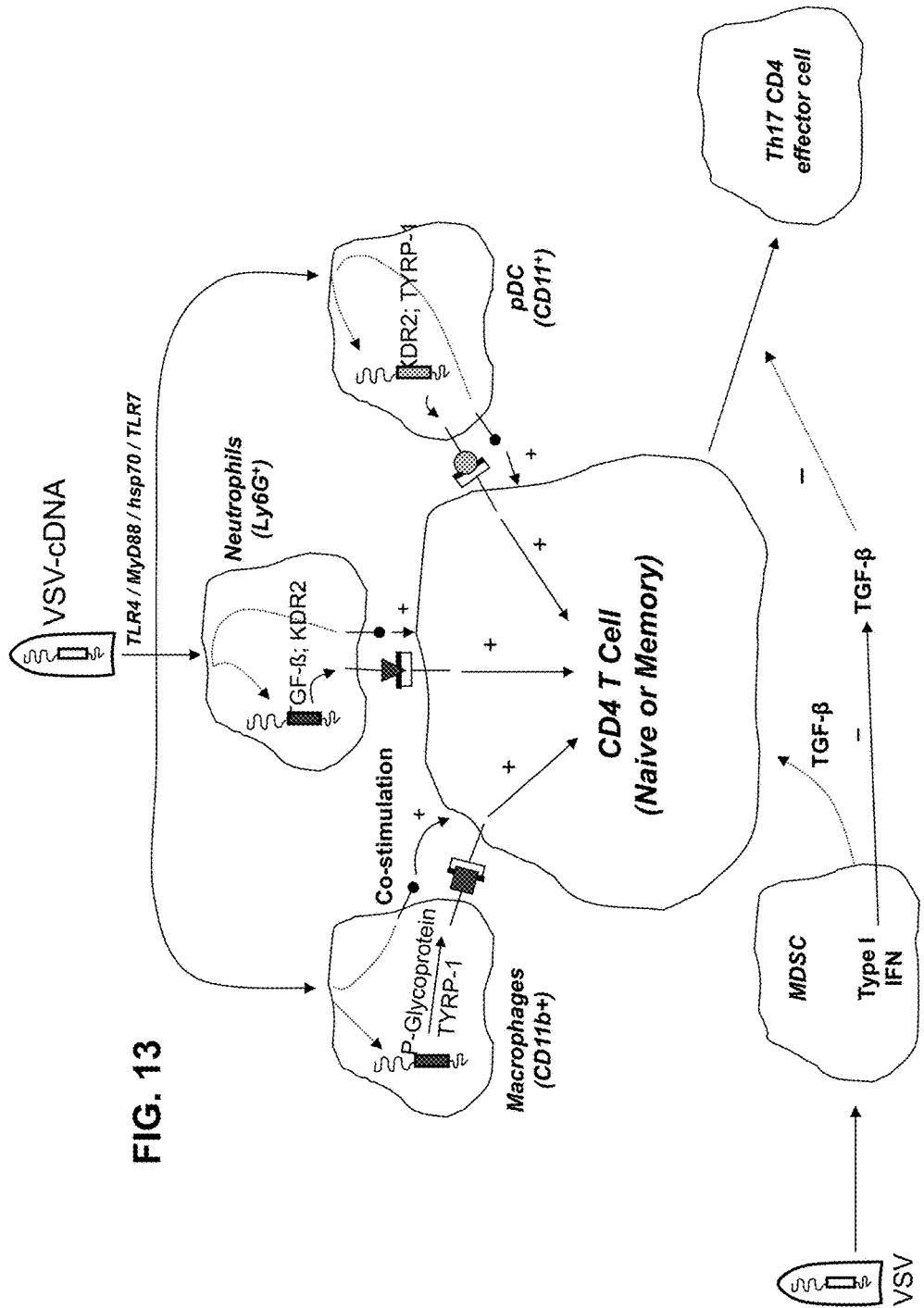
FIG. 13 is a proposed model of antigen presentation.

In another experiment, an in vitro assay (FIG. 10) was performed where splenocytes were depleted of different types of antigen presenting cells by Miltenyi beads. When re-stimulated with the VSV-combination (VSV-TGF-β+VSV-KDR2+VSV-P Glyc+VSV TYRP-1), depletion of certain subsets of APC abrogated IL-17 secretion. Those APC were then infected with a single VSV-TAA (VSV-TGF-β, VSV-KDR2, VSV-P Glyc, or VSV TYRP-1) and re-introduced into the antigen presentation assay. The results were used to determine which specific antigens were presented by which APC subtype in order to reconstitute the Th17 response. P-glycoprotein and N-RAS antigens were presented by macrophages; the TGF-β, KDR2, and CYT-C antigens were presented by neutrophils; and the KDR2 and TYRP1 antigens were presented by plasmacytoid DC (FIGS. 11-13).

Figure 16:
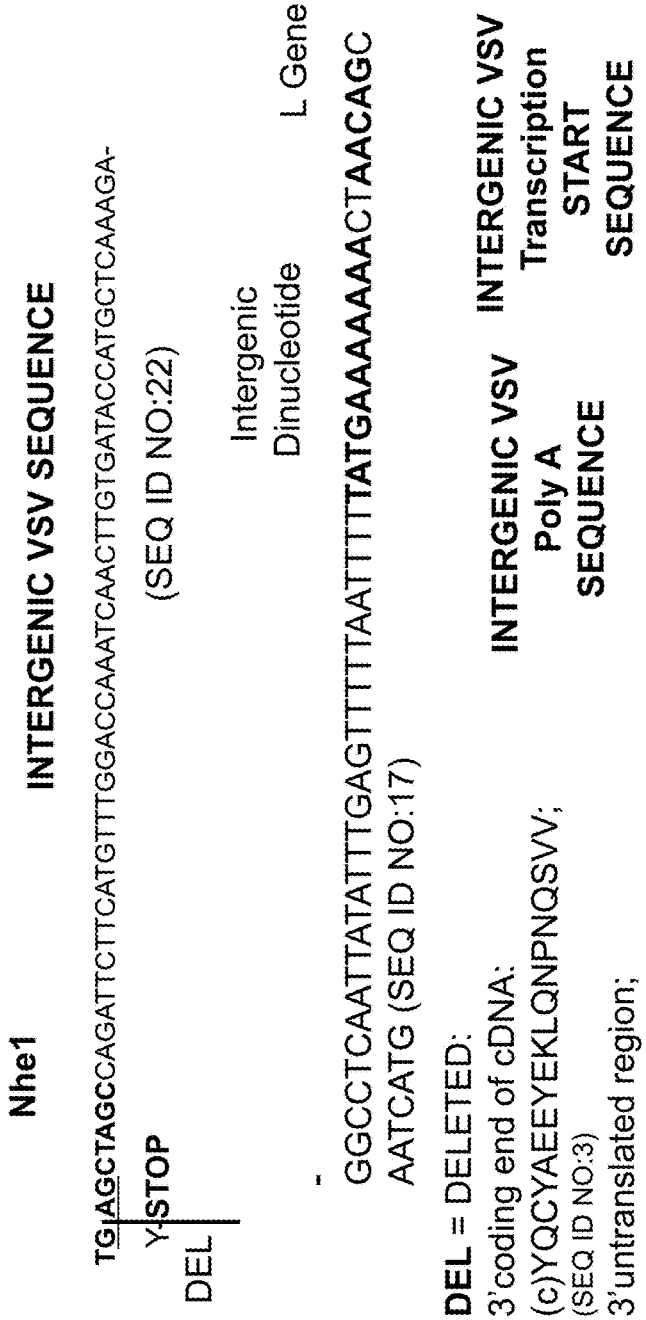
FIG. 16 is contains sequence information for a truncated VSV-TYRP-1 virus recovered from an ASMEL.

Example 6—Treating Melanoma Using VSV Vectors Designed to Express Truncated Antigens VSV vectors having nucleic acid that encodes truncated versions of antigens were recovered from the ASMEL cDNA library. The nucleic acids were sequenced to identify the location of the 3' truncations. For the truncated version of VSV-N-RAS, the VSV vector contained an N-RAS cDNA that encodes an N-RAS polypeptide lacking the following C-terminus: YRMKKLNSSDDGTQGCMGLP-CVVM (SEQ ID NO:1). See, also, FIG. 14. For the truncated version of VSV-CYT-C, the VSV vector contained a CYT-C cDNA that encodes a CYT-C polypeptide lacking the following C-terminus: YTIKRHKWSVLKSRKLAYR-PPK (SEQ ID NO:2). See, also, FIG. 15. For the truncated version of VSV-TYRP-1, the VSV vector contained a TYRP-1 cDNA that encodes a TYRP-1 polypeptide lacking the following C-terminus: YQCYAEEYEKLQNPNQSVV (SEQ ID NO:3). See, also, FIG. 16.

For the truncated version of VSV-TGF-β, the VSV vector contained a TGF-β cDNA that encodes a TGF-β polypeptide lacking the following C-terminus: YYV-GRKPKVEQLSN-MIVRSCKCS (SEQ ID NO:4). For the truncated version of VSV-KDR2, the VSV vector contained a KDR2 cDNA that encodes a KDR2 polypeptide lacking the following C-terminus: YSSEEAELLKLIEIGVQTGSTAQILQPD-SGT-TLSSPPV (SEQ ID NO:5). For the truncated version of VSV-P-glycoprotein, the VSV vector contained a P-glycoprotein cDNA that encodes a P-glycoprotein polypeptide lacking the following C-terminus: YFSMVSVQAGTKRQ (SEQ ID NO:6).

C57BL/6 mice bearing 7 day established s.c. B16 tumors were treated i.v. with 9 doses of (1) VSV encoding library derived, truncated VSV-N-RAS+VSV-CYT-C+VSV TYRP-1 (5×10$^6$ pfu/100 μL), (2) VSV encoding full length polypeptides: VSV-NRAS+VSV-TYRP-1+VSV-CYT-C, or (3) VSV-GFP. Survival of tumor-bearing C57BL/6 (n=8 mice per group) was determined. The results were representative of two separate experiments.

Figure 17:
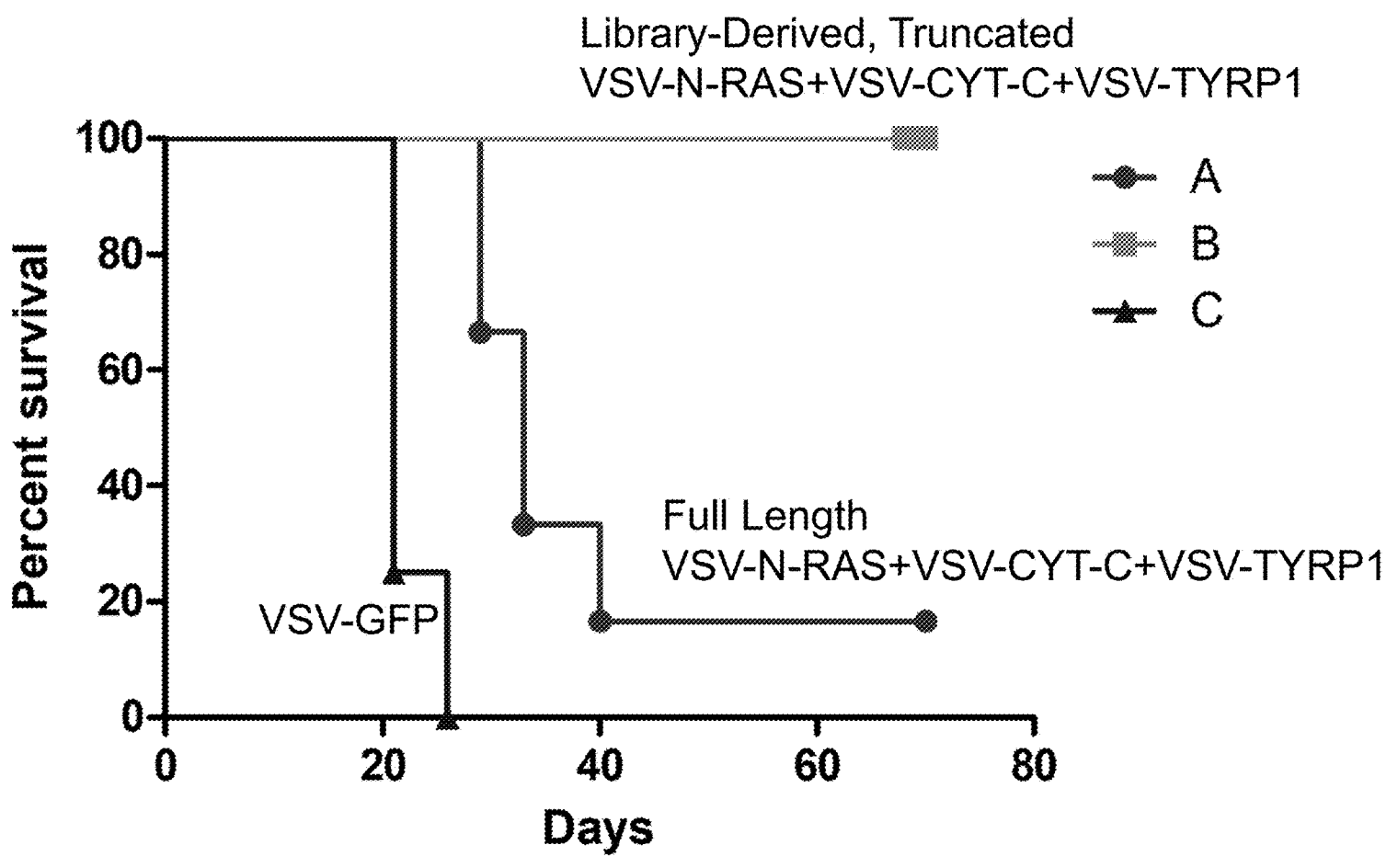

The combination of truncated cDNA for Cytochrome C (CYT-C), N-RAS, and TYRP-1 was more immunogenic against B16 tumors than the full length versions, when expressed from VSV (FIG. 17). The full Length VSV-cDNA combination improved survival of C57B1/6 mice with s.c. B16 tumors, and the truncated virus combination appeared to cure the mice.

These results demonstrate that truncated antigens (e.g., antigens lacking a portion of their C terminus) can be used to treat cancer.

Example 7—Treating Cancer in Dogs

Dogs (e.g., 5-10 dogs) with a solitary intracranial mass consistent with a gliomas based on MRI that is surgically accessible are recruited. The diagnosis is confirmed as a high-grade (III-IV) glioma by histopathology. The dogs are otherwise in good health and able to undergo anesthesia for surgical excision and virus delivery.

The dogs are treated by surgical removal of the tumor and administration of either single VSV vectors (e.g., VSV-HIF-2α only) or a combination of different VSV vectors (e.g., VSV-HIF-2α+VSV-SOX-10+VSV-cMYC). For example, any particular combination of VSV vectors provided herein is administered to a dog having cancer. In some cases, a VSV-cDNA library such as an ASMEL is administered to a dog having cancer.

Toxicities are assessed using a standard veterinary scale of grade I-V events based on owner diaries, serial blood tests, and neurological examinations. Surgical resection of the tumor is performed using the appropriate approach based on MRI. Each dog is administered a standard drug regimen before craniotomy to minimize cerebral edema. After surgical debulking, each dog is administered $5 \times 10^8$ pfu of Reolysin (reovirus) injected in 5-4, aliquots around the resection cavity. A postoperative MRI is performed to assess the extent of resection, and then each dog is allowed to recover from anesthesia and is monitored in an intensive care unit. After surgery, each dog is administered prednisone (1 mg/kg body weight) PO every 12 hours for 2 days, and then the dose is tapered and discontinued over 7 days. Adjustments are made to the dose of steroids depending on the clinical signs, such as changes in mentation or neurological function (i.e., hemiparesis), of each individual dog. The dogs are examined by MRI of the brain performed immediately after surgery and then 4, 8, and 12 months after therapy. The scans are evaluated, and the surgical resection of the tumor is defined as gross total resection (GTR) if there is complete resection of the preoperative fluid-attenuated inversion recovery signal abnormality, near total resection (NTR) if a thin (<3 mm) residual fluid-attenuated inversion recovery signal abnormality remains around the rim of the resection cavity, or subtotal resection (STR) if there is residual nodular fluid-attenuated inversion recovery signal abnormality. The sequential MRI scans are evaluated for volume of tumor in individual dogs to measure response to treatment. Clinical response is considered as complete response (CR) if there is no evidence of the target lesion, partial response (PR) if the tumor is <25% of the original longest diameter of the tumor, progressive disease if there is >25% increase in the original longest diameter of the tumor, or stable disease (SD) if there are small changes that do not meet the previously defined criteria. If a dog develops recurrent or worsening neurologic signs before a scheduled MRI, an unscheduled MRI is performed at that time.

As the immunological boost, each dog is treated with intravenous injections of $5 \times 10^6$ pfu of VSV-TAA (e.g., a single VSV vector such as VSV-HIF-2α only or a combination of different VSV vectors such as VSV-HIF-2α+VSV-SOX-10+VSV-cMYC) on days 10, 30, 60, 90, 120, 150, 180, 210, 240, 270, 300, 330, and 360 after surgery, or until tumor recurrence. For example, any particular combination of VSV vectors provided herein is administered to a dog having cancer as an immunological boost. In some cases, a VSV-cDNA library such as an ASMEL is administered to a dog having cancer as an immunological boost.

Dogs are monitored for 30 minutes following each injection for any immediate adverse reactions, such as severe wheals, dyspnea, or other signs of anaphylaxis. Dogs suffering from an acute severe reaction are given dexamethasone (0.01 mg/kg SC) and diphenhydramine (0.5 mg/kg IM). Dogs are followed over a 12-month period by imaging or until euthanasia. Dogs are assessed with complete physical and neurological examinations and quality of life assessments at suture removal and each VSV-TAA injection.

Peripheral blood mononuclear cells (PBMC) are collected prior to surgery and on days 10, 60, 120, 180, 240, 300, and 360 after surgery to determine immunological response by re-stimulating the PBMC in vitro to measure T cell responses against autologous tumor cells by flow cytometry. In some cases, CTL assays and Western blots on serum are performed.

Example 8—Treating Cancer Using VSV Designed to Express IFN-β

Figure 18:
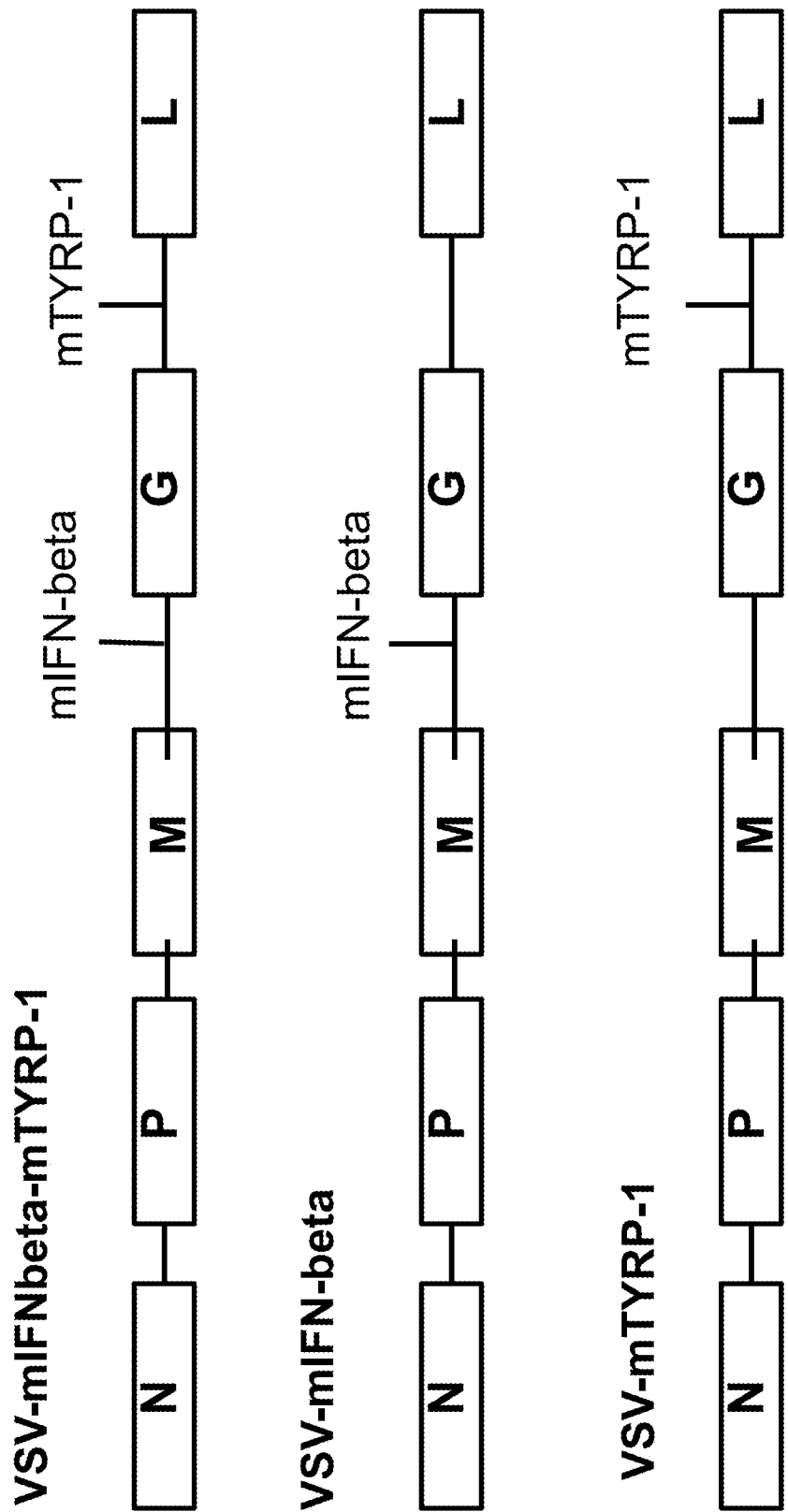
FIG. 18 is a schematic of the indicated VSV vectors.

VSV encoding TYRP-1 (full length) and IFN-β (VSV-mIFN-mTYRP-1) was generated by inserting mTYRP-1 in the vector backbone containing IFN-β (IFN-β) located between the M and G genes of VSV (FIG. 18). PCR amplification of mTYRP-1 cDNA was prepared from B16 cells using forward (5'-CTCGAGATG-AAATCTTA-CAACGTCC-3'; SEQ ID NO:7) and reverse (5'-CTAGCTAGCTCA-GACCATGGAGTGGTTA-3'; SEQ ID NO:8) primers. The PCR product was then digested and inserted into the XhoI and NheI site (between genes G and L of VSV) of the VSV-IFN-β vector. VSV-mTYRP-1 was generated by inserting TYRP-1 between the G and L genes. Viruses were generated from BHK cells by co-transfection of pVSV-XN2-cDNA library DNA along with plasmids encoding viral genes as described elsewhere (Fernandez et al., *J. Virol.*, 76:895-904 (2002)). Virus was expanded by a single round of infection of BHK cells and purified by sucrose gradient centrifugation.

IFN Gamma Assay

Figure 19:
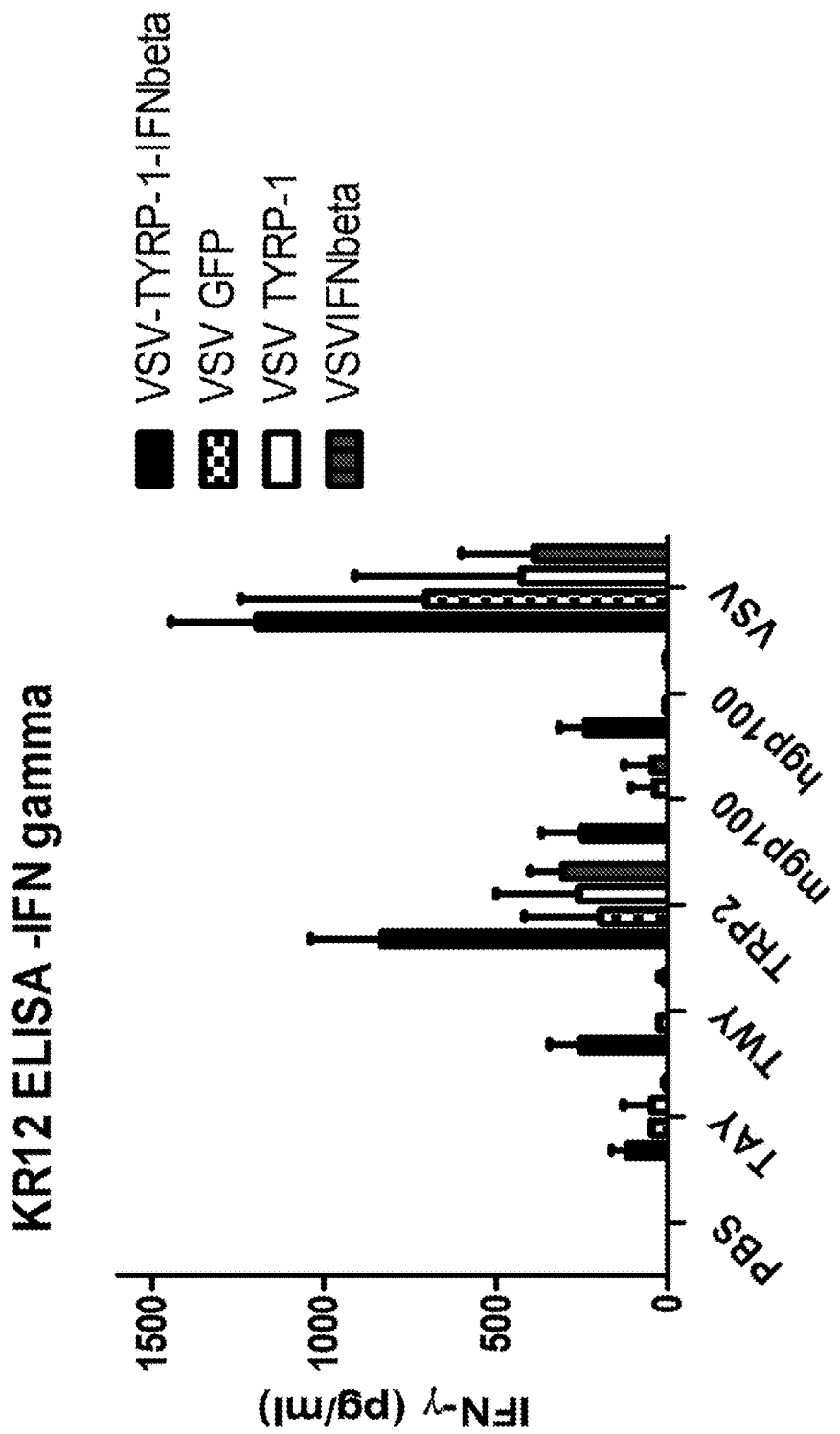
FIG. 19 is a bar graph plotting IFN-γ levels (pg/mL) for cells obtained from mice treated as indicated and stimulated with the indicated polypeptides.

Splenocytes/LN from C57BL/6 mice bearing s.c. B16 tumors and treated with PBS alone or with either VSV-GFP, VSV-mTYRP-1, VSV-mIFN-β-TYRP-1, or VSV-mIFN-β were harvested. Splenocytes were re-stimulated in vitro with PBS, VSV N peptide VSV-N52-59 (RGYVYQGL; SEQ ID NO:9) or with synthetic H-2Kb-restricted melanoma peptides: murine TRP-1222-229 (TAYRYHLL, SEQ ID NO:10; or TWYRYHLL SEQ ID NO:11; TAY, TWY, respectively), TRP-2180-188 (SVYDFFVWL, SEQ ID NO:12; TRP2), murine gp100 (EGSRNQDWL, SEQ ID NO:13; mgp100), or human gp10025-33 (KVPRNQDWL, SEQ ID NO:14; hgp100). Forty eight hours later, supernatants were assayed for IFN-γ by ELISA (FIG. 19).

Figure 20:
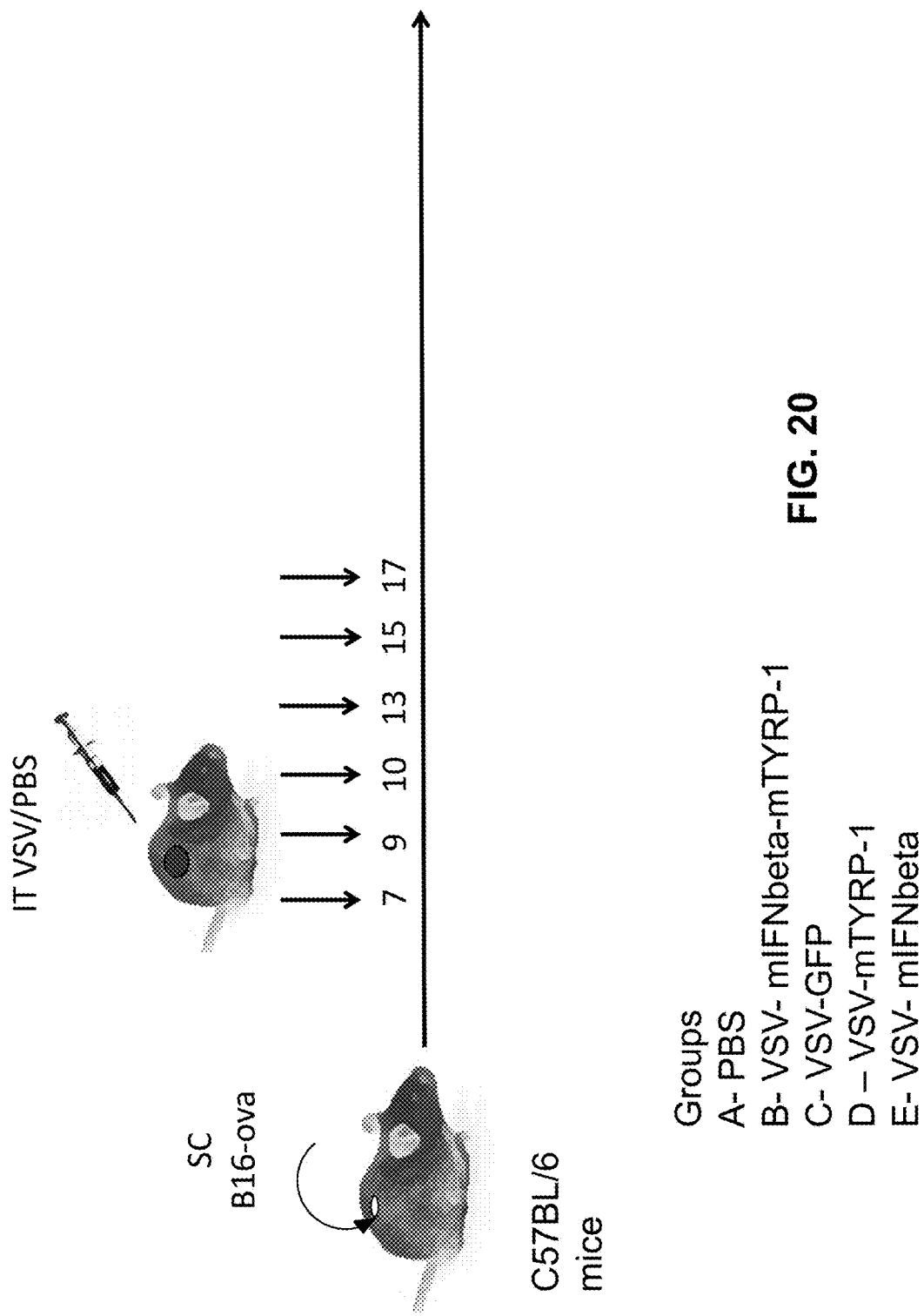
FIG. 20 is a schematic of an in vivo assay for assessing VSV vectors expressing IFN-β polypeptides.

In Vivo Results $5 \times 10^5$ B16-ova tumor cells in 100 μL of PBS were injected into the flanks of C57BL/6 mice (7 mice per treatment group). Seven days later, mice were treated intratumorally (IT) with PBS, VSV encoding antigens, or VSV-GFP at $7 \times 10^8/50$ μL for three days every other day (FIG. 20). Survival times were determined (FIG. 21).

These results demonstrate that the combined use of a VSV vector encoding an antigen (e.g., TYRP-1) with IFN-β results in prolonged cancer survival and also an enhanced IFN-γ response.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising one or more viral vectors comprising nucleic acid, wherein the nucleic acid of said composition encodes a combination of tumor antigens, wherein said combination of tumor antigens consists of a GNAQ antigen, a TYRP1 antigen, and an N-RAS antigen, and wherein said GNAQ antigen, said TYRP1 antigen, and said N-RAS antigen are expressed from said viral vectors.

2. The composition of claim 1, wherein said composition comprises a first viral vector encoding said GNAQ antigen, a second viral vector encoding said TYRP1 antigen, and a third viral vector encoding said N-RAS antigen.

3. A method of treating cancer within a mammal, wherein said method comprises administering to said mammal a composition comprising one or more viral vectors comprising nucleic acid, wherein the nucleic acid of said composition encodes a combination of tumor antigens, wherein said combination of tumor antigens consists of a GNAQ antigen, a TYRP1 antigen, and an N-RAS antigen, and wherein said GNAQ antigen, said TYRP1 antigen, and said N-RAS antigen are expressed from said viral vectors.

4. The method of claim 3, wherein said cancer is a melanoma.

5. The method of claim 3, wherein said mammal is a human.

6. The method of claim 3, wherein said composition comprises a first viral vector encoding said GNAQ antigen, a second viral vector encoding said TYRP1 antigen, and a third viral vector encoding said N-RAS antigen.

* * * * *

SEQUENCE LISTING

<160> NUMBER OF SEQ ID NOS: 23

<210> SEQ ID NO 1
<211> LENGTH: 24
<212> TYPE: PRT
<213> ORGANISM: Homo sapiens

<400> SEQUENCE: 1

Tyr Arg Met Lys Lys Leu Asn Ser Ser Asp Asp Gly Thr Gln Gly Cys
1               5                   10                  15

Met Gly Leu Pro Cys Val Val Met
            20

<210> SEQ ID NO 2
<211> LENGTH: 22
<212> TYPE: PRT
<213> ORGANISM: Homo sapiens

<400> SEQUENCE: 2

Tyr Thr Ile Lys Arg His Lys Trp Ser Val Leu Lys Ser Arg Lys Leu
1               5                   10                  15

Ala Tyr Arg Pro Pro Lys
            20

<210> SEQ ID NO 3
<211> LENGTH: 19
<212> TYPE: PRT
<213> ORGANISM: Homo sapiens

<400> SEQUENCE: 3

Tyr Gln Cys Tyr Ala Glu Glu Tyr Glu Lys Leu Gln Asn Pro Asn Gln
1               5                   10                  15

Ser Val Val

<210> SEQ ID NO 4
<211> LENGTH: 23
<212> TYPE: PRT
<213> ORGANISM: Homo sapiens

<400> SEQUENCE: 4

Tyr Tyr Val Gly Arg Lys Pro Lys Val Glu Gln Leu Ser Asn Met Ile
1               5                   10                  15

Val Arg Ser Cys Lys Cys Ser
            20

<210> SEQ ID NO 5
<211> LENGTH: 38
<212> TYPE: PRT
<213> ORGANISM: Homo sapiens

<400> SEQUENCE: 5

Tyr Ser Ser Glu Glu Ala Glu Leu Leu Lys Leu Ile Glu Ile Gly Val
1               5                   10                  15

Gln Thr Gly Ser Thr Ala Gln Ile Leu Gln Pro Asp Ser Gly Thr Thr
            20                  25                  30

Leu Ser Ser Pro Pro Val
        35

<210> SEQ ID NO 6
<211> LENGTH: 14
<212> TYPE: PRT
<213> ORGANISM: Homo sapiens

<400> SEQUENCE: 6

Tyr Phe Ser Met Val Ser Val Gln Ala Gly Thr Lys Arg Gln
1               5                   10

<210> SEQ ID NO 7
<211> LENGTH: 25
<212> TYPE: DNA
<213> ORGANISM: Mus musculus

<400> SEQUENCE: 7
ctcgagatga aatcttacaa cgtcc                                              25

<210> SEQ ID NO 8
<211> LENGTH: 28
<212> TYPE: DNA
<213> ORGANISM: Mus musculus

<400> SEQUENCE: 8
ctagctagct cagaccatgg agtggtta                                           28

<210> SEQ ID NO 9
<211> LENGTH: 8
<212> TYPE: PRT
<213> ORGANISM: Vesicular stomatitis virus

<400> SEQUENCE: 9

Arg Gly Tyr Val Tyr Gln Gly Leu
1               5

<210> SEQ ID NO 10
<211> LENGTH: 8
<212> TYPE: PRT
<213> ORGANISM: Mus musculus

<400> SEQUENCE: 10

Thr Ala Tyr Arg Tyr His Leu Leu
1               5

<210> SEQ ID NO 11
<211> LENGTH: 8
<212> TYPE: PRT
<213> ORGANISM: Mus musculus

<400> SEQUENCE: 11

Thr Trp Tyr Arg Tyr His Leu Leu
1               5

<210> SEQ ID NO 12
<211> LENGTH: 8
<212> TYPE: PRT
<213> ORGANISM: Mus musculus

<400> SEQUENCE: 12

Ser Val Tyr Asp Phe Phe Val Trp
1               5

<210> SEQ ID NO 13
<211> LENGTH: 9
<212> TYPE: PRT
<213> ORGANISM: Mus musculus

<400> SEQUENCE: 13

Glu Gly Ser Arg Asn Gln Asp Trp Leu

<210> SEQ ID NO 14
<211> LENGTH: 9
<212> TYPE: PRT
<213> ORGANISM: Homo sapiens

<400> SEQUENCE: 14

Lys Val Pro Arg Asn Gln Asp Trp Leu
1               5

<210> SEQ ID NO 15
<211> LENGTH: 55
<212> TYPE: DNA
<213> ORGANISM: Mus musculus

<400> SEQUENCE: 15
gaccagacag ggtgttgaag atgcttttta cacactggta agagaaatac gccag       55

<210> SEQ ID NO 16
<211> LENGTH: 60
<212> TYPE: DNA
<213> ORGANISM: Vesicular stomatitis virus

<400> SEQUENCE: 16
tgagctagcc agattcttca tgtttggacc aaatcaactt gtgataccat gctcaaagay  60

<210> SEQ ID NO 17
<211> LENGTH: 56
<212> TYPE: DNA
<213> ORGANISM: Vesicular stomatitis virus

<400> SEQUENCE: 17
ggcctcaatt atatttgagt ttttaatttt tatgaaaaaa actaacagca atcatg 56

<210> SEQ ID NO 18
<211> LENGTH: 62
<212> TYPE: DNA
<213> ORGANISM: Mus musculus

<400> SEQUENCE: 18
accatcgaaa acgcatgggg ctcaagatgt tgatgatgat ggctctgctg gtgcccctgg 60
tc 62

<210> SEQ ID NO 19
<211> LENGTH: 60
<212> TYPE: DNA
<213> ORGANISM: Vesicular stomatitis virus

<400> SEQUENCE: 19
tgagctagcc agattcttca tgtttggacc aaatcaactt gtgataccat gctcaaagay 60

<210> SEQ ID NO 20
<211> LENGTH: 56
<212> TYPE: DNA
<213> ORGANISM: Vesicular stomatitis virus

<400> SEQUENCE: 20
ggcctcaatt atatttgagt ttttaatttt tatgaaaaaa actaacagca atcatg 56

<210> SEQ ID NO 21
<211> LENGTH: 66
<212> TYPE: DNA

```
<213> ORGANISM: Mus musculus

<400> SEQUENCE: 21
gcttcttatc tgattcgtgc cagacgcagt atggatgaag ctaaccagcc tctcctcact    60
gatcag                                                               66

<210> SEQ ID NO 22
<211> LENGTH: 60
<212> TYPE: DNA
<213> ORGANISM: Vesicular stomatitis virus

<400> SEQUENCE: 22
tgagctagcc agattcttca tgtttggacc aaatcaactt gtgataccat gctcaaagay    60

<210> SEQ ID NO 23
<211> LENGTH: 56
<212> TYPE: DNA
<213> ORGANISM: Vesicular stomatitis virus

<400> SEQUENCE: 23
ggcctcaatt atatttgagt ttttaattttt tatgaaaaaa actaacagca atcatg       56
```